(12) United States Patent
Chang et al.

(10) Patent No.: US 7,754,467 B2
(45) Date of Patent: *Jul. 13, 2010

(54) SURFACE EXPRESSION OF BIOLOGICALLY ACTIVE PROTEINS IN BACTERIA

(75) Inventors: Chia-Hwa Chang, Mountain View, CA (US); Xiaowen Liu, Cupertino, CA (US); John A. Lewicki, Los Gatos, CA (US); Qiang Xu, Cupertino, CA (US)

(73) Assignee: Osel, Inc., Santa Clara, CA (US)

( * ) Notice: Subject to any disclaimer, the term of this patent is extended or adjusted under 35 U.S.C. 154(b) by 1167 days.

This patent is subject to a terminal disclaimer.

(21) Appl. No.: 10/766,993

(22) Filed: Jan. 28, 2004

(65) Prior Publication Data

US 2005/0003510 A1 Jan. 6, 2005

Related U.S. Application Data

(60) Provisional application No. 60/443,619, filed on Jan. 29, 2003.

(51) Int. Cl.
*C12N 1/21* (2006.01)
*A61K 48/00* (2006.01)
*C07K 14/195* (2006.01)

(52) U.S. Cl. ............... 435/252.3; 424/93.2; 530/350

(58) Field of Classification Search ............ 435/252.3; 424/93.2; 530/350
See application file for complete search history.

(56) References Cited

U.S. PATENT DOCUMENTS

| 6,190,662 B1 * | 2/2001 | Steidler et al. ............ 424/184.1 |
| 7,179,458 B2 * | 2/2007 | Chang et al. ............... 424/93.2 |
| 2003/0228297 A1 | 12/2003 | Chang et al. |
| 2006/0073530 A1 * | 4/2006 | Schneewind et al. ....... 435/7.32 |
| 2007/0117197 A1 * | 5/2007 | Chang et al. ............. 435/252.3 |

FOREIGN PATENT DOCUMENTS

| WO | WO 96/11277 A1 | 4/1996 |
| WO | WO 2004/007695 A2 | 1/2004 |

OTHER PUBLICATIONS

Rudinger in Peptide Hormones, Parsons (ed.), University Park Press: Baltimore, MD, pp. 1-7, 1976.*
Ngo et al., 1994, The protein Folding Problem and Tertiary Structure Prediction, pp. 491-495.*
Davis, New Biologist, 1990, 2(5), 410-419.*
Skolnick et al Trends in Biotech, 2000,18, 34-39.*
Pancholi et al J. Bacteriol. 1988, 170:2618-2624.*
Strauss et al Mol. Microbiol. 1996, 21:491-500.*
Chang et al Proc Natl Acad Sci U S A. 2003; 100(20): 11672-11677.*
Baneyx et al Microbial Cell Fact., 2004,3 (6) 1-2.*
Villaverde Biotechnology Letters, 2003, 25: 1385-1395.*
Avall-Jaaskelainen, Silja et al.; "Surface Display of the Receptor-Binding Region of the *Lactobacillus brevis* S-Layer Protein in *Lactococcus lactis* Provides Nonadhesive Lactococci with the Ability to Adhere to Intestinal Epithelial Cells"; 2003, *Applied and Environmental Microbiology*, vol. 69, No. 4, pp. 2230-2236.
Giomarelli, Barbara et al.; "The microbicide cyanovirin-N expressed on the surface of commensal bacterium *Streptococcus gordonii* captures HIV-1"; 2002, *AIDS Concise Communication*, vol. 16, No. 10, pp. 1351-1356.
Liu, Janice J. et al.; "Activity of HIV entry and fusion inhibitors expressed by the human vaginal colonizing probiotic *Lactobacillus reuteri* RC-14"; 2006, *Cellular Microbiology*, pp. 1-11.
Maggi, Tiziana et al.; "Genetic engineering of *Streptococcus gordonii* for the simultaneous display of two heterologous proteins at the bacterial surface"; 2002, *FEMS Microbiology Letters*, vol. 210, pp. 135-141.
Navarre, William Wley et al.; "Surface Proteins of Gram-Positive Bacteria and Mechanisms of Their Targeting to the Cell Wall Envelope"; 1999, *Microbiology and Molecular Biology Reviews*, vol. 63, No. 1, pp. 174-229.
Pallen, Mark J. et al.; An embarrassment of sortases—a richness of substrates?; 2001, *Trends in Microbiology*, vol. 9, No. 3, pp. 97-100.
Samuelson, Patrik et al.; "Display of proteins on bacteria"; 2002, *Journal of Biotechnology*, vol. 96, pp. 129-154.
Schneewind, Olaf et al.; "Sorting of Protein A to the Staphlococcal Cell Wall"; 1992, *Cell*, vol. 70, pp. 267-281.
Strauss, Andreas et al.; "In vivo immobilization of enzymatically active polypeptides on the cell surface of *Staphylococcus carnosus*"; 1996, *Molecular Microbiology*, vol. 21, No. 3, pp. 491-5000.
That, Hung Ton et al.; "An embarrassment of sortases—a richness of substrates?"; 2001, *Trends in Microbiology*, vol. 9, No. 3, pp. 101.
Vallor, Ana C. et al.; "Factors Associated with Acquisition of, or Persistent Colonization by, Vaginal Lactobacilli: Role of Hydrogen Peroxide Production"; 2001, *Infec. Dis.*, vol. 184, pp. 1431-1436.
Gilbert, C. et al.; "A New Cell Surface Proteinase: Sequencing and Analysis of the PRTB Gene from *Lactobacillus delbruckii* Subsp. *bulgaricus*"; 1996, *Journal of Bacteriology, American Society of Microbiology*, vol. 178, No. 11, pp. 3059-3065.
Kruger, C. et al.; "In situ delivery of passive immunity by lactobacilli producing single-chain antibodies"; 2002, *Nature Biotechnology*, vol. 20, No. 7, pp. 702-706.
Martinez, Beatriz et al.; "Expression of cbsA encoding the collagen-binding S-protein of *Lactobacillus crispatus* JCM5810 in *Lactobacillus casei* ATCC 393T"; 2000, *Journal of Bacteriology*, vol. 182, No. 23, pp. 6857-6861.
Roos, S. et al.; "A high-molecular-mass cell-surface protein from *Lactobacillus reuteri* 1063 adheres to mucus components"; 2002, *Microbiology, Society for General Microbiology*, vol. 148, No. 2, pp. 433-442.
Scheppler, L. et al.; "Recombinant *Lactobacillus johnsonii* as a mucosal vaccine delivery vehicle"; 2002, *Vaccine*, vol. 20, No. 23-24, pp. 2913-2920.
Turner, Mark S. et al.; "Peptide surface display and secretion using two LPXTG-containing surface proteins from *Lactobacillus fermentum* BR11"; 2003, *Applied and Environmental Microbiology*, vol. 69, No. 10, pp. 5855-5863.

* cited by examiner

*Primary Examiner*—Deborah Crouch
*Assistant Examiner*—Anoop Singh
(74) *Attorney, Agent, or Firm*—Townsend and Townsend and Crew LLP

(57) ABSTRACT

Methods and compositions for targeting heterologous polypeptides to bacterial cell walls are provided.

21 Claims, 14 Drawing Sheets

Figure 2A

C14 SEQUENCE RESULTING FROM GENOMIC SEQUENCING OF L. JENSENII 1153 (CWA200 REGION ALONG WITH ANCHOR MOTIF UNDERLINED)

$^1$MNDSSIGTINITNDITITGKVNGLTTSGISDINKHFLYLQSEGSARDLTINGNGHRINFA
GYSIALQNKNYTNAANPWNITLKDMTIEGSKYDYSPISFYGRKSNTENSKLTFDGVT
ANLNDRPLVDKYGENLPVHFAGENNITLNNMSIGYNLVTGKTVKFDSGNTTFNVDG
KVTGNSINPDNWVIRSTENASNSENPSTLINEGATVTINAKSDDLRGIYAGRQLTAGQ
PIYGVTVINGTLNAKMAAGHSTAIWSHDLEIGKKGNVTIHTKQTNQADGVENGTSNS
VTNYNGTHYAPISLGVGPISSVASPLSKQTVSLINNGSLTIIRDTAKKTLVPLISMGDGS
LSSNTTLKFSVGAGATLDLQDKAGTFRYGIEPSTPLNGLVTLWGTSGTDLLEFLTPAY
VNLQRTGDIRGTLIRMEGVYNSTTVNGPTPVAQWDQGNKTTTPNDVWYVRYLISAN
QWGNNSGQFMGKDQHPNTVVAKKGVDTLYNSNATVLMSKNQGADKYENGTMPT
EVQQALHLNSFLNNFNFWRPQRMAMGSKLNDNPDVKIDDFDKYHAEAQTIDGTTR
QTLSDLDANKGLKDLIGPDEQPITDFKDIVKHVTWYNSATDKDEWNKIMIQPTDSKD
PSARVPYPEPQNPTGNLKTTDGFAWAKVTYADGSVDFVKIPLKVTEKKYSEELTPSY
PGVSVEQGKSDSVDPSFKDENDKAADAPAGTKYTAGENTPDWIKVDPDTGKVTVSP
TDDTSVGSHDISVTVTYPDSSTDQLTVPVTVTEKSNLAEKYPVSYDKLNVEKPSGDT
PATGAVDPKAAADMPEGAITGYEKGDFDAPAGVTIDVNHDTGKVTASVGKNATLG
SFEVPVKVTYSDGTYAEVKVPVSITGNKVDPGSGDVVYYGDQSMVVFNGNLTTVH
KTTDSHELSAKDSAFQTITYYSDWNKKGNIVSDYNKHVIYKLSADGTKYVNEADAT
DSFDASAISFNWQKGYEVNTGVDNFSNGSADTLYQLEKGAVNSEEQTDANDPSGLA
GNSKYRYDFSISDTNVLQKLGLSPAGYNAWANVYYNFLGATGKINIPVNYGSEVSTD
EAGIKNYLATNSISGKTFVNGNPTGIKWAENGMPGKDGKFAASNMTGIVEFTFDNGT
KLNVQVTFKTGSHVSTSGSKVNDDTNLYVERTIEYDVTGTGHSPINSVTQKVHYVRD
GYHKINADGTDAGEIIWNEWKLADGQTAEFPEYSVDQITGYDAYINGAKATQVDAA
KVAETNGTPQNGQNITVTYKKQNSTPVPYKPGKDGVNDAINRYVTRTIIVKEPGKEP
QTITQTVHFTNEDKDGNSGYKDPVTGEIKYNTDWHVASDLNAKTGSWEEYTAPSVT
GYTPSQAKVEAKTVTAETEAASVTISYTKNADIPVPYKPGKDGVNDAINRYVTRTIIV
KEPGKEPQTITQTVHFTNEDKDGNSGYKDPVTGEIKYNTDWHVASDLNAKTGSWEE
YTAPSVTGYTPSQAKVEAKTVTAETEAASVTISYTKNADIPVPFDPSNKDMYRE<u>VTR
TINVVDPITGKISTSVQTAKFTREDKNSNAGYTDPVTGKTTMNPWTPAKQGLRAVNV
EQIKGYVAKVDGNVDAVVVTPDSANMVVTITYQANKPEGQNITVKKDTVPDPADGI
KNKDDLPDGTKYTWKEVPDVNSVGEKTGIVTVTFPDGTSVDVKVTVYVDPVVESN
RDTLSKEANTGNTNVAKAATVTSSKVESKKTLPQTGSKTEQVGILGLAIATVGSLLG
LGVNRKKRQK</u>$^{1765}$

Figure 2B

C191 SEQUENCE RESULTING FROM GENOMIC SEQUENCING OF *L. JENSENII* 1153 (WITH CWA200 REGION ALONG WITH ANCHOR MOTIF UNDERLINED)

$^{1}$MPVANKPEGTVHTTYSWKDNIIPDTTKPGTKYGIVEVNFPDGSTKDVPVEVKVTSL
ASDYQNKIDTKQIIAKYKGNIPQASDGIANKDQATKEGDKDFPSLADVLAPNGIQWK
KNFEPDLSKPGLTSGEAILTFKDGSTAEVTIPVLVQTDADRNTPETQTIKTLPGQTVNP
EDGVINLHKPGENNPQLPDGTKVTFDNQSDVDDFTKHGMPGSDKSFDATVTYPDGT
TDKIKLPVHITADNEVNTPITQGIITPKDSVPDANKGIANLKKATTKEGKTYPALPENT
TVEWVNPGQMKTELENAKGGTTKNYDAVVIYPDKSTEIVSIPVTVATDADTYKVVT
QPIDLKDRNLPDNADDGITNLHKPADFKTPQLPDGTHAEWQDKDAAQEVVKNLKPG
ETVKLPATVVFPDGSKKGEGIDVSVHLHGQSDDYNIETQPVNTDKDGNLPENADSGI
KNLGKLPEGTHASWGDGAQDIAKNLKPGETKDVPATVVFPDGSKKEITIPVHREGQS
DGYDVEPQLVNTDKNGQLPNAKEGIKNLADLPEGTNPTWADRAQDKINKTKPGTDT
TAQVVVTFPDGSTKEVTVPVHKHGQSDDYGDKIVTQRVETDSHGQLPENADSGIKN
LGDLPEGTHAVWGQGAQTIVDGMKPGETKDVPATIEFPDGSTKDVTIPVYKTSTRDQ
GTLNPPTDKVSVDDTKHITDEDKGKVIDNVKKSNPDKDITDAHVDDDGTFHGKVDG
QDVVIPGTETVVEKQKESLNPPTDKVPVDDTKHITDEDKGKVIDNVKKSNPDKDITD
AHVDDDGTFHGKVDGQ<u>DVVIPGTETVVEKQKESLNPPTDKVPVDDTKHITDEDKGK
VIDNVKKSNPDKDITDAHVDDDGTFHGKVDGQDVVIPGIETVVEKSTNNQKSDTNK
GLISNDNSEKNSHMINANVNTKSRNSLSAKQNRL</u>LPQTGSETSGLSALGLAMLSLVGL
GFLIKKRKED$^{974}$

Figure 2C

**C370 SEQUENCE RESULTING FROM GENOMIC SEQUENCING OF *L. JENSENII* 1153 (WITH CWA200 REGION ALONG WITH ANCHOR MOTIF UNDERLINED)**

¹MFYQIDPALAPYIDKIVFSRALLSDGEATKDTSNEVPGATNVWTSGVLTTQNGPIRA
ALAGSTSSTYKIYLKADTPNSILSKPLSFTMWARYSSGHDMVSDFSKNLILNDNETTT
FSSNNFFKSLDIVNNDGPILDNMSVDYSNKTVNTRYRVNGSLLGDKSNLTLRIRGND
NLLKLIDKVKISNKTYTLANNTLKYRTGELYINDIGGSLGFLSSLSNRQDFNVTFYLK
NGKSFADALTSESQKFDFQFGIYDTTDYATAFHSLDTVTNSLSTKTYTTGDKYNNQT
YDLSTFKTILDKLIKQKQDNPTTYLSFEDKKISATENNPYEAVKLALESPTFTNISIAKS
LVNAADCKQLDNTAKWAWDNGARDDLLKYLDVATKVASYIHLEFPTKPTDFSGLL
LRYTRAGTFISAVDSDRDGVLDITEIDNSYGMNPSVYDTDGDGISDGQELREGRDPG
VAPFNWTDANGNQLSIDVDTTTISGQLGNHNYHNEVMQPRTVNLYKVDDTGKKTLI
AYTTSAVDQNGSFTLSKFTLNKGDKLVIGYVTPRTNKSLTDKDTILQQAFPTEQFSNE
IIVKGKQVTVTFNMNGVSDDENQDIKVEKDSSFNKDSLTLPTPTMKTGYSFKEWNTQ
ADGKGTVVTADTIFDTDTTVYAIGEKIKLPNPTNIKAETRTDDKTKSQETIITGKATPG
ATVTIKDNLGNEIGTGVANDAGNFEIKTTSPLAEATKVSVEATKGGESSDAVEATVE
QNNFQKGNPLIQPASPTAVTAVTIKASDGTNNSTTVTGKAAAGETVTVKDSSGNEIG
TGVVGEDGTFTITTNKPIAENERIQVVVTKDDAESEPTEAVVTAKTEPTNPTEVTAKT
LPDGNSDSTIVAGKGKAGE
VVTVKNDAGKVIGTGKVSDDGTFSIKTDEVIEPGKQVSVITTNDGMDSIPVPVTVSGE
TITSIKQSAKAAVDNLTYLNNAQKQSAKDAIDSANTVDEITTAKNNAVSTDTNMKDL
SEDTKLAADKTQDPYLNADLDKKQAYDKAVEEAQKLLNKETGTSVGADKDPAEVA
RIKQAVDDAYDALNGNSSLDDAKQKAKDAVDKNYTNLNDKQKETAKKRIDSAKSE
DEVNNADKINSGLNEKMGELKEVSNLSDKIETTSNYSNADSDKKQAYKETADKIHET
VAPSGDDLTTDDVNNLITDEATKRAALNGDAREKARQE
LENNYNSGKSLQDGSTLDPRYYNASEEKKQAFQKALDNAKKALDNSETTEAEYKSA
NDELQKAKADLDGQTTDKSKLDDAIKDANNAKGTDKYKNASDDTKSKFDEALKKA
EEVKNNSNATQKEVDDATNNLKQAQNNLNGQTTDKSKLDDAIKDANNAKGTDKY
KNASDDTKSKFDDALKKAEEVKNNSNATQKEVDDATNNLKQAQNDLDGQTTDKS
KLDEAITDANNTKLTDKYNNASDDTKSKFDEALKKAENVKNDSNATQKEVDDATN
NLKQAQNDLDGQTTDKSKLDEAITDANNTKSTDKYNNASDDTKSKFDEALKKAEE
VKNNSNATQKEVDDATNNLKQAQNNLDGQTTDKSKLDEAITDANNTKSTDKYKNA
SDDTKSKFDDALKKAEEVKNNSNATQKEVDDATNNLKQAQNDLDGQTTNKDTLND
AIKDANDAKGTDKYKNASDDTKSKLDETL<u>KKAEEVKNNSNATQKEVDDATNNLKQ
AQNDLDGQTTDKSKLDEAIKSADDTKSTDKYNNASDDTKSKFDEALKKAEEVKNNS
NATQKEVDDATKNLKQAQNDLDGQTTNKDAINDAIKDANNAKGTDKYNNASDDT
KSKFDDALKKAEDVKNDSNANQKEVDDATKNLKNTLNNLKGQPAKKANLIASKDN
AKIHKQTLLPQTGTETNPLTAIGIGLMALGAGIFAKKKRKDDEA</u>¹⁹⁰³

Figure 5
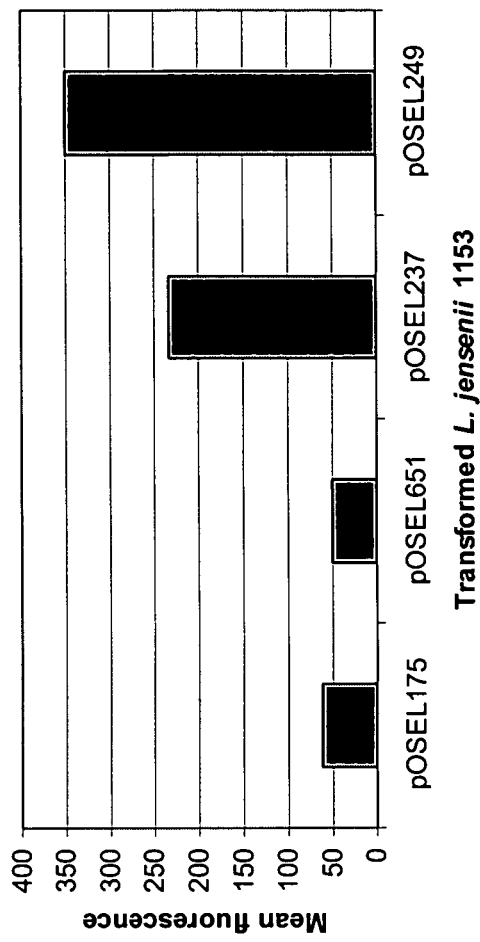
A.
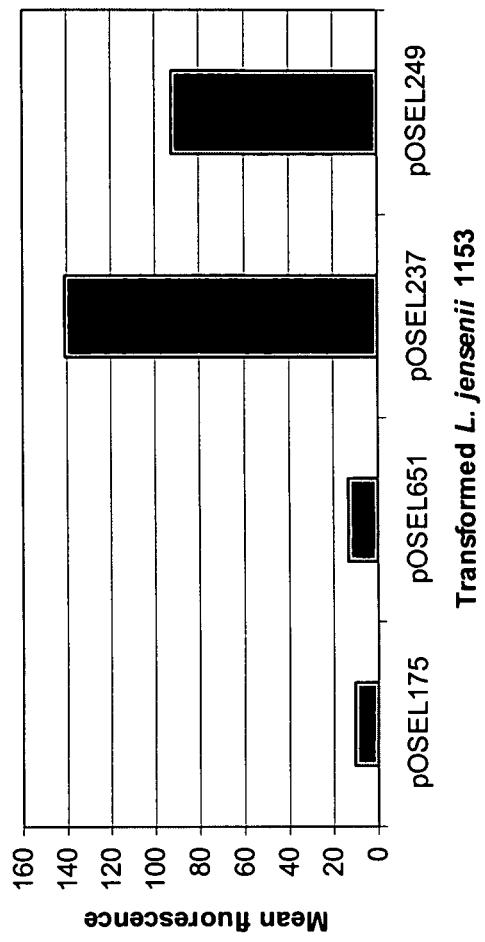
B.

Figure 6
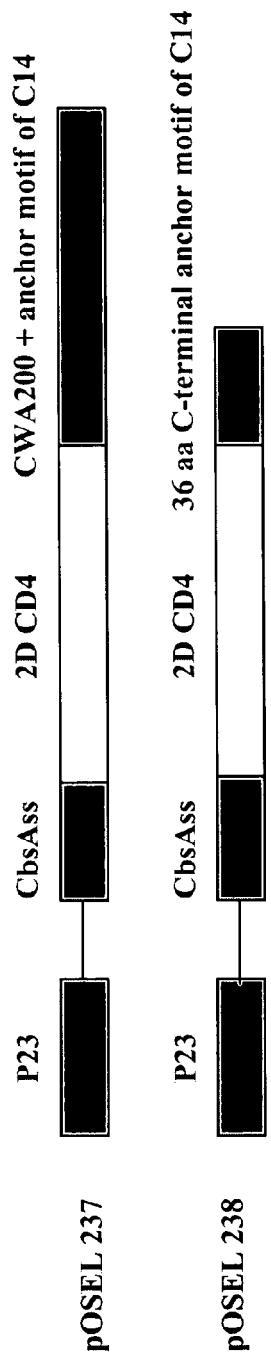
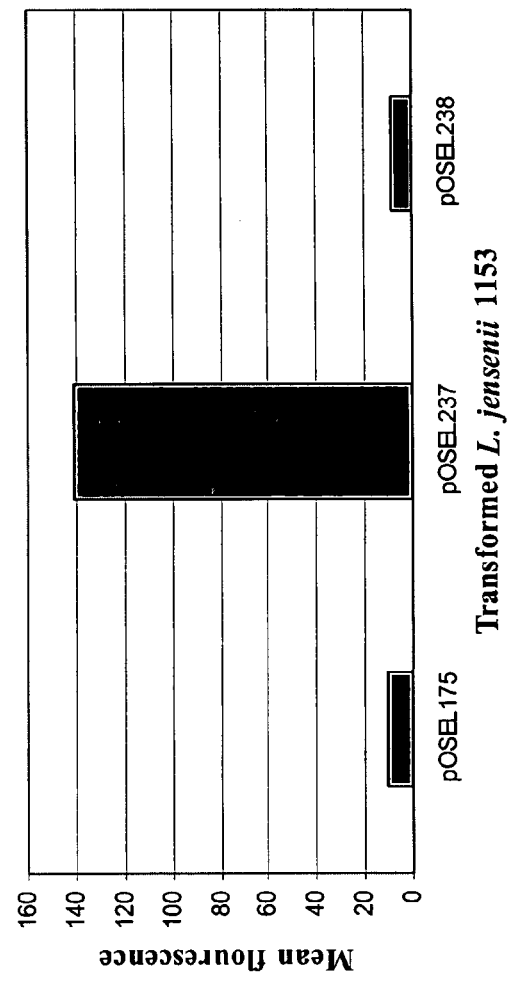

SURFACE EXPRESSION OF BIOLOGICALLY ACTIVE PROTEINS IN BACTERIA

CROSS REFERENCE TO RELATED APPLICATIONS

The present application claims benefit of priority to U.S. Provisional patent application No. 60/443,619, filed on Jan. 29, 2003, which is incorporated by reference in its entirety for all purposes.

STATEMENT AS TO RIGHTS TO INVENTIONS MADE UNDER FEDERALLY SPONSORED RESEARCH AND DEVELOPMENT

This invention was made with Government support under Grant No. 2 R44 AI46203-02, awarded by the National Institutes of Health. The government has certain rights in this invention.

BACKGROUND OF THE INVENTION

Surface expression of proteins via covalent linkage with peptidoglycans in Gram-positive bacteria involves unique sorting signals and Sortase-dependent machinery (Mazmanian et al., Science 285:760-763 (1999)). One of the best-studied systems is the emm6 gene of *Streptococcus pyogenes* that encodes the M6 structural protein (Fischetti et al., 1990. *Mol. Microbiol.* 4:1603-1605 (1990)). The M6 proteins have a signature cell wall sorting signal, the Leu-Pro-X-Thr-Gly (LPXTG; SEQ ID NO:9) motif, followed by a stretch of hydrophobic amino acids and finally a sequence containing charged residues (KRKEEN; SEQ ID NO:10), which serves as a cell surface retention signal. These cell wall sorting motifs have been identified in other Gram-positive bacteria including *Staphlyococcus*, *Enterococcus*, and *Listeria*, and *Lactobacillus* (Navarre and Schneewind, *Microbio. Mol. Biol. Rev.* 63:174-229 (1999)), but not in *Lactobacillus* species that colonize the human vagina.

The mucosal membranes of all humans are naturally colonized by bacteria (Tannock. *Clin. Rev. Allergy Immunol.* 22: 231-53 (2002)). Recent scientific evidence has documented the fact that these bacteria interact closely with cells and tissues of the body to regulate natural biological processes. It has become increasingly evident that this mucosal microflora also contributes substantially to numerous diseases affecting cells and tissues of humans.

Generally, domination of the microflora within the vagina and gastrointestinal tract, by lactobacilli and related bacteria, is associated with good health (Redondo-Lopez et al., *Rev. Infect. Dis.* 12: 856-72 (1990); Tannock. *Clin. Rev. Allergy Immunol.* 22: 231-53 (2002)). Natural strains of lactobacilli have been administered for many years as "probiotics" for the purpose of maintaining a healthy microflora within these locations and preventing infection. It is well established that these "healthy bacteria" compete with pathogenic organisms, such as bacteria, viruses and fungi to limit the development and progression of pathogen associated diseases. Nevertheless, this microflora is a fragile and dynamic environment with the natural turnover and disruption of the healthy microflora being associated with the establishment of opportunistic infections. Consequently, approaches to maintain, or even enhance, the integrity and natural properties of the microflora, as a means of preventing or treating disease, would be coveted by the biomedical community.

The mucosal microflora contributes to many local diseases affecting mucosal surfaces. For instance, HIV and other sexually transmitted pathogens must bypass the vaginal mucosa. In addition, the etiology of inflammatory bowel diseases, including ulcerative colitis and Crohn's disease may arise from inappropriate interactions between a disrupted mucosal microflora and cells and tissues of the host. A means of modulating the properties of bacteria within the mucosal flora could aid in the prevention or treatment of these diseases, as well as related conditions affecting mucosal surfaces. Targeting biologically active proteins to the cell wall of these and other organisms could help to treat such diseases.

The present invention addresses these and other problems.

BRIEF SUMMARY OF THE INVENTION

The present invention provides *Lactobacillus* bacteria comprising an expression cassette, the expression cassette comprising a promoter operably linked to polynucleotide encoding a signal sequence and a biologically-active polypeptide, wherein the biologically active polypeptide is linked to a heterologous carboxyl terminal cell wall targeting region and wherein the heterologous carboxyl terminal cell wall targeting region comprises in the following order: a cell wall associated sequence; LPQ(S/A/T)(G/A); and a hydrophobic sequence.

In some embodiments, the cell wall associated sequence comprises at least 50 amino acids. In some embodiments, the cell wall associated sequence comprises at least 200 amino acids. In some embodiments, the heterologous carboxyl terminal cell wall targeting region further comprises a charged sequence at the carboxyl terminus of region.

In some embodiments, the *Lactobacillus* bacterium is a vagina colonizing strain. In some embodiments, the bacterium is selected from the group consisting of *L. jensenii*, *L. gasseri*, *L. casei*, and *L. crispatus*.

In some embodiments, the cell wall targeting region comprises the amino acid sequence LPQSG (SEQ ID NO:11). In some embodiments, the cell wall targeting region comprises the amino acid sequence LPQAG (SEQ ID NO:12). In some embodiments, the cell wall targeting region comprises the amino acid sequence LPQTG (SEQ ID NO:13). In some embodiments, the cell wall targeting region comprises the amino acid sequence LPQTA (SEQ ID NO:14). In some embodiments, the cell wall targeting region comprises SEQ ID NO:7. In some embodiments, the cell wall targeting region comprises SEQ ID NO:8.

In some embodiments, the biologically active polypeptide is expressed in the cell wall of the bacterium. In some embodiments, the biologically-active polypeptide is between 10 and 600 amino acids. In some embodiments, the biologically active protein binds to a pathogen when the biologically active protein is contacted with the pathogen.

In some embodiments, the pathogen is a bacterial pathogen. In some embodiments, the pathogen is a fungal pathogen. In some embodiments, the pathogen is a viral pathogen.

In some embodiments, the viral pathogen is a human immunodeficiency virus (HIV). In some embodiments, the biologically active protein is CD4 or an HIV-binding fragment of CD4. In some embodiments, the biologically active protein is 2D-CD4. In some embodiments, the biologically active protein is cyanovirin-N (CV-N) or a virus-binding fragment of CV-N. In some embodiments, the viral pathogen is herpes simplex virus. In some embodiments, the biologically active protein is herpes simplex virus entry mediator C (HveC) or a virus-binding fragment of HveC.

In some embodiments, the biologically active polypeptide is released from the *Lactobacillus* bacterium. In some embodiments, the biologically active polypeptide is anchored to the cell wall of the *Lactobacillus* bacterium.

The present invention also provides methods of expressing a biologically active polypeptide in the cell wall of a *Lactobacillus* bacterium. In some embodiments, the method comprises providing a *Lactobacillus* bacterium comprising an expression cassette, the expression cassette comprising a promoter operably linked to a polynucleotide encoding a signal sequence and a biologically-active polypeptide, wherein the biologically active polypeptide is linked to a heterologous carboxyl terminal cell wall targeting region and wherein the heterologous carboxyl terminal cell wall targeting region comprises in the following order: a cell wall associated sequence; LPQ(S/A/T)(G/A); and a hydrophobic sequence; and culturing the bacterium under conditions to induce expression of the polypeptide, thereby expressing a biologically active polypeptide in the cell wall of the *Lactobacillus* bacterium.

In some embodiments, the cell wall associated sequence comprises at least 50 amino acids. In some embodiments, the cell wall associated sequence comprises at least 200 amino acids.

In some embodiments, the heterologous carboxyl terminal cell wall targeting region further comprises a charged sequence at the carboxyl terminus of region. In some embodiments, the providing step comprises transferring the expression cassette into the bacterium.

In some embodiments, the cell wall targeting region comprises the amino acid sequence LPQSG (SEQ ID NO:11). In some embodiments, the cell wall targeting region comprises the amino acid sequence LPQAG (SEQ ID NO:12). In some embodiments, the cell wall targeting region comprises the amino acid sequence LPQTG (SEQ ID NO:13). In some embodiments, the cell wall targeting region comprises the amino acid sequence LPQTA (SEQ ID NO:14). In some embodiments, the cell wall targeting region comprises SEQ ID NO:7. In some embodiments, the cell wall targeting region comprises SEQ ID NO:8.

In some embodiments, the cell wall targeting region comprises at least 200 amino acids.

In some embodiments, the bacterium is vagina-colonizing strain. In some embodiments, the bacterium is selected from the group consisting of *L. jensenii, L. gasseri, L. casei*, and *L. crispatus*. In some embodiments, the biologically-active polypeptide is between 10 and 600 amino acids. In some embodiments, the biologically active protein binds to a pathogen when the biologically active protein is contacted with the pathogen.

In some embodiments, the pathogen is a bacterial pathogen. In some embodiments, the pathogen is a fungal pathogen. In some embodiments, the pathogen is a viral pathogen.

In some embodiments, the viral pathogen is HIV. In some embodiments, the biologically active protein is CD4 or an HIV-binding fragment of CD4. In some embodiments, the biologically active protein is 2D-CD4. In some embodiments, the biologically active protein is cyanovirin-N or a virus-binding fragment of cyanovirin-N. In some embodiments, the biologically active protein is herpes simplex virus entry mediator C (HveC) or a virus-binding fragment of HveC.

In some embodiments, the biologically active polypeptide is released from the *Lactobacillus* bacterium. In some embodiments, the biologically active polypeptide is anchored in the cell wall of the *Lactobacillus* bacterium.

The present invention also provides methods of providing a biologically active protein to a mammalian mucosal surface. In some embodiments, the methods comprise contacting a mucosal surface with a *Lactobacillus* bacterium recombinantly altered to express a signal sequence linked to a biologically-active polypeptide linked to a heterologous carboxyl terminal cell wall targeting region, the heterologous carboxyl terminal cell wall targeting region comprising in the following order: a cell wall associated sequence; LPQ(S/A/T)(G/A); and a hydrophobic sequence, wherein the biologically active polypeptide is expressed in an amount able to be detected in a sample collected from the mucosal surface.

In some embodiments, the cell wall associated sequence comprises at least 50 amino acids. In some embodiments, the cell wall associated sequence comprises at least 200 amino acids. In some embodiments, the heterologous carboxyl terminal cell wall targeting region further comprises a charged sequence at the carboxyl terminus of region. In some embodiments, the *Lactobacillus* bacterium is selected from the group consisting of *L. jensenii, L. gasseri, L. casei* and *L. crispatus*.

In some embodiments, the mucosal surface resides within the vagina. In some embodiments, the mucosal surface resides within the gastrointestinal tract.

In some embodiments, the contacting step comprises orally administering the *Lactobacillus* bacteria. In some embodiments, the contacting step comprises vaginally administering the *Lactobacillus* bacteria. In some embodiments, the contacting step comprises rectally administering the *Lactobacillus* bacteria.

The present invention provides expression cassettes comprising a promoter operably linked to polynucleotide encoding a signal sequence and a biologically-active polypeptide, wherein the biologically active polypeptide is linked to a heterologous carboxyl terminal cell wall targeting region, the heterologous carboxyl terminal cell wall targeting region comprising in the following order: a cell wall associated sequence; LPQ(S/A/T)(G/A); and a hydrophobic sequence. In some embodiments, the cell wall associated sequence comprises at least 50 amino acids. In some embodiments, the cell wall associated sequence comprises at least 200 amino acids.

In some embodiments, the heterologous carboxyl terminal cell wall targeting region further comprises a charged sequence at the carboxyl terminus of region.

In some embodiments, the cell wall targeting region comprises the amino acid sequence LPQSG (SEQ ID NO:11). In some embodiments, the cell wall targeting region comprises the amino acid sequence LPQAG (SEQ ID NO:12). In some embodiments, the cell wall targeting region comprises the amino acid sequence LPQTG (SEQ ID NO:13). In some embodiments, the cell wall targeting region comprises the amino acid sequence LPQTA (SEQ ID NO:14). In some embodiments, the cell wall targeting region comprises SEQ ID NO:7. In some embodiments, the cell wall targeting region comprises SEQ ID NO:8. In some embodiments, the biologically-active polypeptide is between 10 and 600 amino acids.

In some embodiments, the biologically active protein binds to a pathogen when the biologically active protein is contacted with the pathogen. In some embodiments, the pathogen is a bacterial pathogen. In some embodiments, the pathogen is a fungal pathogen. In some embodiments, the pathogen is a viral pathogen. In some embodiments, the viral pathogen is HIV.

In some embodiments, the biologically active protein is CD4 or an HIV-binding fragment of CD4. In some embodiments, the biologically active protein is 2D-CD4. In some embodiments, the biologically active protein is cyanovirin-N or a virus-binding fragment of cyanovirin-N. In some embodiments, the biologically active protein is herpes simplex virus entry mediator C (HveC) or a virus-binding fragment of HveC. In some embodiments, the cell wall targeting region functions in *Lactobacillus*.

The present invention also provides vectors comprising an expression cassette comprising a promoter operably linked to polynucleotide encoding a biologically-active polypeptide linked to a heterologous carboxyl terminal cell wall targeting region, the heterologous carboxyl terminal cell wall targeting region comprising in the following order: a cell wall associated sequence; LPQ(S/A/T)(G/A); and a hydrophobic sequence.

DEFINITIONS

A "biologically active protein" refers to an amino acid sequence that has the biological activity (i.e., can participate in the molecular mechanisms) of the amino acid sequence within, or outside of, a native cell. Activity of a protein includes, e.g., its immunogenicity, catalytic activity, binding affinity, etc. Polypeptide vaccines are encompassed by the term "biologically active proteins." Typically, the amino acid sequence forms the three-dimensional structure formed by the amino acid sequence within or outside of the native cell.

"2 D CD4" refers to the first approximately 183 amino acids of human CD4 (Arthos et al., *Cell.* 1989. 57: 469-81 (1989)). CD4 is a cell-surface glycoprotein found on the mature helper T cells and immature thymocytes, as well as monocytes and macrophages. 2D-CD4 binds to HIV-1 gp120 with the same affinity as the intact protein, and contains the binding site for gp120. CD4 contains an amino-terminal extracellular domain (amino acid residues 1 to 371), a transmembrane region (372 to 395) and a cytoplasmic tail (396 to 433).

"Antibody" refers to a polypeptide substantially encoded by an immunoglobulin gene or immunoglobulin genes, or fragments thereof which specifically bind and recognize an analyte (antigen). The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well characterized fragments produced by digestion with various peptidases. Thus, for example, pepsin digests an antibody below the disulfide linkages in the hinge region to produce F(ab')2, a dimer of Fab which itself is a light chain joined to $V_H$-$C_H$1 by a disulfide bond. The F(ab')2 may be reduced under mild conditions to break the disulfide linkage in the hinge region, thereby converting the F(ab')2 dimer into an Fab' monomer. The Fab' monomer is essentially an Fab with part of the hinge region (see, Paul (Ed.) *Fundamental Immunology*, Third Edition, Raven Press, NY (1993)). While various antibody fragments are defined in terms of the digestion of an intact antibody, one of skill will appreciate that such fragments may be synthesized de novo either chemically or by utilizing recombinant DNA methodology. Thus, the term antibody, as used herein, also includes antibody fragments either produced by the modification of whole antibodies or those synthesized de novo using recombinant DNA methodologies (e.g., single chain Fv).

The term "isolated," when applied to a nucleic acid or protein, denotes that the nucleic acid or protein is essentially free of other cellular components with which it is associated in the natural state. It is preferably in a homogeneous state although it can be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified. In particular, an isolated gene is separated from open reading frames that flank the gene and encode a protein other than the gene of interest. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

The term "nucleic acid" or "polynucleotide" refers to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)). The term "nucleic acid" is used interchangeably with "polynucleotide."

The terms "polypeptide," "peptide," and "protein," are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins (i.e., antigens), wherein the amino acid residues are linked by covalent peptide bonds.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds that have a structure that is different from the general chemical structure of an amino acid, but which functions in a manner similar to a naturally occurring amino acid.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

Two nucleic acid sequences or polypeptides are said to be "identical" if the sequence of nucleotides or amino acid residues, respectively, in the two sequences is the same when aligned for maximum correspondence as described below. The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers & Miller, *Computer Applic. Biol. Sci.* 4:11-17 (1988) e.g., as implemented in the program PC/GENE (Intelligenetics, Mountain View, Calif., USA).

The phrase "substantially identical," in the context of two nucleic acids or polypeptides, refers to a sequence or subsequence that has at least 70% sequence identity with a reference sequence. Alternatively, percent identity can be any integer from 40% to 100%. More preferred embodiments include at least: 40%, 45%, 50%, 55%, 60%, 65%, 70%, 75%, 80%, 85%, 90%, 91%, 92%, 93%, 94%, 95%, 96%, 97%, 98 or 99% compared to a reference sequence (e.g., SEQ ID NO: 1, SEQ ID NO: 2, SEQ ID NO: 3, SEQ ID NO:4, SEQ ID NO:5, SEQ ID NO:6, SEQ ID NO:7, or SEQ ID NO:8 or fragments thereof) using the programs described herein, such as BLAST using standard parameters, as described below.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Natl. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

An example of an algorithm that is suitable for determining percent sequence identity and sequence similarity is the BLAST algorithm, which is described in Altschul et al., *J. Mol. Biol.* 215:403-410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Natl. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The term "recombinant" or "recombinantly altered" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (nonrecombinant) form of the cell or express native genes that are otherwise abnormally expressed, under-expressed or not expressed at all.

The term "heterologous" when used with reference to portions of a nucleic acid or a polypeptide indicates that the nucleic acid or polypeptide comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

An "expression cassette" is a nucleic acid, generated recombinantly or synthetically, with a series of specified nucleic acid elements that permit transcription of a particular nucleic acid in a host cell. The expression cassette can be part of a plasmid, virus, or nucleic acid fragment. Typically, the expression vector includes a nucleic acid to be transcribed operably linked to a promoter.

BRIEF DESCRIPTION OF THE DRAWINGS

FIGS. 2A-C illustrates cell wall anchor sequences (C14 (SEQ ID NO:1), C191 (SEQ ID NO:2), and C370 (SEQ ID NO:3)) resulting from genomic sequencing of L. jensenii 1153. The CWA200 region along with anchor motif is underlined. CWA200 represents putative cell wall associated or spanning regions of about 200 amino acids upstream of the LPQTG (SEQ ID NO:13) motif.

FIG. 5 illustrates results from flow cytometric analysis of L. jensenii 1153 harboring plasmids designed for secretion or surface anchoring of 2D CD4. The bacterial cells were probed with rabbit pAb against CD4 (T4-4), and then FITC-conjugated anti-rabbit antibodies (A). Alternatively, the bacterial cells were probed with mAb Sim.4, and then PE-conjugated anti-mouse IgG (B). Controls consisted of unstained cells or cells probed with fluorochrome-conjugated secondary antibodies. The fluorescence density as a measure of antibody binding to bacterial surface was calculated using FLOWJO software.

FIG. 6 illustrates that the C-terminal anchor motif of 36-amino acid in length is insufficient to drive surface expression of 2D CD4. (A). Constructs designed for surface expression of 2D CD4 using native anchor sequences in L. jensenii. (B). Flow cytometric analysis of L. jensenii 1153 harboring pOSEL238 or pOSEL237. The bacterial cells were probed with mAb Sim.4 against CD4, and then phycoerythrin (PE)-conjugated anti-mouse antibodies. Controls consisted of unstained cells or cells probed with PE-conjugated secondary antibodies.

DETAILED DESCRIPTION OF THE INVENTION

I. Introduction

Figure 1:
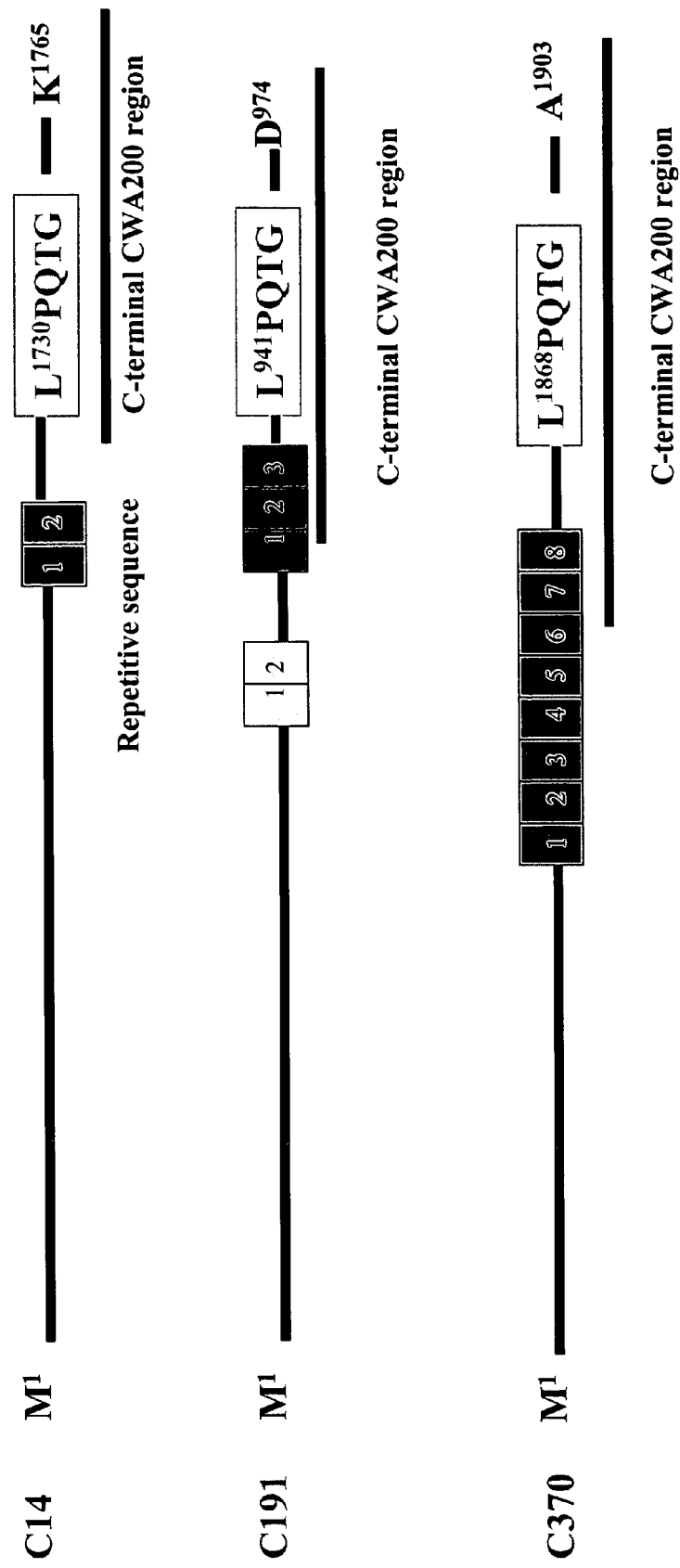
FIG. 1 illustrates the structures of three cell wall anchored proteins identified after genomic sequencing of L. jensenii 1153. All of the three proteins have LPQTG (SEQ ID NO:13) sorting signal preceding a hydrophobic region and a charged C-terminal tail and possess unique long repetitive sequences. CWA represents putative cell wall associated regions upstream of the LPQTG (SEQ ID NO:13) motif.
Figure 3:
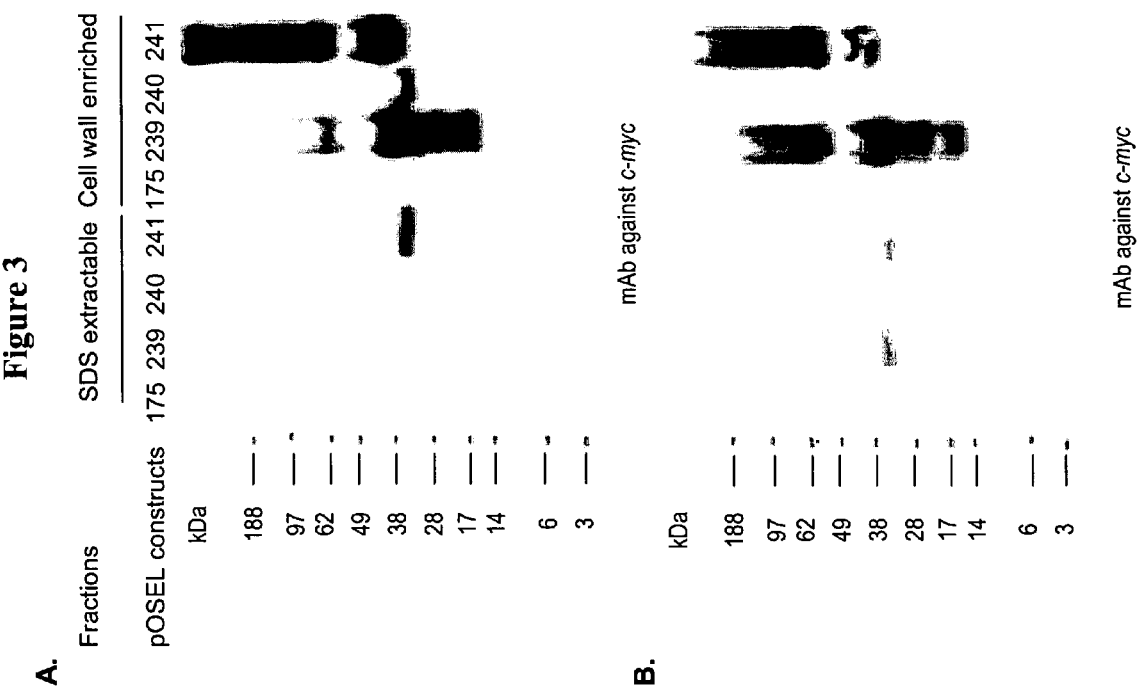
FIG. 3 illustrates results from western analysis of SDS extractable proteins and cell wall enriched fractions following mutanolysin digestion of transformed L. jensenii 1153 when cultured in MRS broth (A) or Rogosa SL broth (B) at 37° C. and 5% $CO_2$. After separation in reducing SDS-PAGE, the proteins were electroblotted to PVDF membranes for probing with monoclonal antibody (mAb) against c-Myc.

The present invention provides novel motifs and methods for expressing heterologous polypeptides on the cell wall of Gram-positive bacteria such as Lactobacillus. The motifs of the invention can be fused to a protein of interest and then expressed as a fusion protein in the bacteria, resulting in targeting, imbedding, and/or surface display of the fusion protein in the cell wall, or releasing the biologically active and stable fusion protein to the extracellular matrix.

The motifs are useful, for instance, for expression of proteins on the cell wall of Lactobacillus bacteria that colonize the human mucosa, including the vagina. Exemplary mucosal bacteria include Lactobacillus species, such as L. jensenii, L. gasseri, and L. casei.

II. Cell Wall Targeting Regions

To express and target a polypeptide of interest covalently anchored to a cell wall in Gram-positive bacteria such as Lactobacillus, the cell wall targeting region is C-terminally linked to a heterologous polypeptide of interest. The cell wall targeting region enabling surface display of heterologous proteins in vaginally-associated lactobacilli as well as other lactobacilli is comprised of four parts: a cell wall associated region, a LPQ(S/A/T)(G/A) sequence, and a hydrophobic sequence, typically in that order. Optionally, the cell wall targeting region will comprise a charged region at or near the carboxyl terminus. The charged region acts as a stop-transfer sequence in the cell membrane, thereby preventing release into the media. Of course, release into the media may still occur if the anchoring sequence is cleaved from the rest of the protein.

A. Cell Wall Associated Region

The cell wall associated region precedes the LPQ(S/A/T)(G/A) sorting signal. The length of the cell wall associated region may vary. The cell wall associated region is typically between 40 and 1,000 amino acids. In some embodiments, the cell wall associated region is at least about 30, 50, 80, 100, 150, 200 or more amino acids. In some embodiments, the cell wall associated region has about 500, 400, 300, 250, 200, 150, 100 or fewer amino acids. In Lactobacillus jensenii, a stretch of 95 amino acids containing one tandem repeat in fusion with the C-terminal cell wall sorting signal in pOSEL268 (described in the Examples) enables surface display of CD4. However, approximately 50 amino acids long in M6 protein of S. pyogenes was identified based on peptide mapping (Pancholi & Fischetti, J. Bacteriol. 170:2618-2624 (1988)), whereas about 90 amino acids of a fibronectin binding protein was postulated in S. carnosus (Strauss & Gotz, Mol. Microbiol. 21:491-500 (1996)). Thus, sequences about 50 amino acids or less can be functional in Lactobacillus.

In some embodiments, the cell wall associated region is hydrophilic. In some embodiments, the cell wall associated region contains imperfect tandem repeats that can vary in length and sequence. For example, the cell wall associated region of L. jensenii C370 contains two and a half tandem repeats. However, while tandem repeats may occur in the cell wall associated region, it is not required. For example, the cell wall associated region of C14 contains no repeats. Functionally, the cell wall associated region interacts with and spans the peptidoglycan layer. Accordingly, it is also called a cell wall spanning or attachment domain, acting as a spacer between the protein that is anchored by membrane-associated sortase and the cell wall sorting signal.

The present invention provides cell wall associated regions substantially identical to the C370 sequence KKAEEVKNNSNATQKEVDDATNNLKQAQNDLDGQ-TTDKSKLDEAIKSADDTKSTDKYNNASDDTKSKFD-EALKKAEEVKNNSNATQKEVDDATKNLKQAQNDL-DGQTTNKDAINDAIKDANNAKGTDKYNNASDDTKS-KFDDALKKAEDVKNDSNANQKEVDDATKNLKNTL-NNLKGQPAKKANLIASKDNAKIHKQTL (SEQ ID NO:4). In some cases, the cell wall associated region comprises at least about 40, 50, 75, 90, 100, 120, 150, 175, 200 amino acid fragments of the C370 sequence. For example, an active cell wall associated fragment can comprise the following sequence: GQTTNKDAINDAIKDANNAKGTDKYN-NASDDTKSKFDDALKKAEDVKNDSNANQKEVDD-ATKNLKNTLNNLKGQPAKKANLIASKDNAKIHKQTL (SEQ ID NO:5). The C370 sequence (SEQ ID NO:4) comprises 75 charged amino acid residues (K, R, D, E) and lacks Pro-Gly rich sequences.

In some embodiments, the cell wall associated regions is substantially identical to the C14 sequence: VTRTINVVD-PITGKISTSVQTAKFTREDKNSNAGYTDPVTGKTT-MNPWTPAKQGLRAVNVEQIKGYVAKVDGNVDA-VVVTPDSANMVVTITYQANKPEGQNITVKKDTVPDP ADGIKNKDDLPDGTKYTWKEVPDVNSVGEKTGIV-TVTFPDGTSVDVKVTVYVDPVVESNRDTLSKEANT-GNTNVAKAATVTSSKVESKKT (SEQ ID NO:6). In some cases, the cell wall associated region comprises at least about 40, 50, 75, 90, 100, 120, 150, 175, 200 amino acid fragments of the C370 sequence. SEQ ID NO:6 comprises 51 charged amino acid residues (K, R, D, E).

In some cases, the cell wall associated region is derived from bacteria other than Lactobacillus or from a Lactobacillus strain not associated with the vagina.

B. LPQ(S/A/T)(G/A)

The sequence LPQ(S/A/T)(G/A) acts as a cell wall sorting signal in vaginally associated strains of Lactobacillus. At least one copy of the motif LPQ(S/A/T)(G/A) is in the cell wall targeting region. The parentheses in the motif indicate alternative amino acids in that position (e.g., LPQAG, LPQAG, LPQTG, LPQSA, LPQAA, LPQTA (SEQ ID NOS: 11, 12, 13, 18, 19 and 14, respectively)).

C. Hydrophobic Sequences

The carboxyl terminus of a polypeptide to be anchored in the cell wall comprises a hydrophobic region that functions to span the bacterial membrane. The hydrophobic region comprises at least about 50%, and in some embodiments, at least 60%, 70%, 80% or 90% hydrophobic amino acids. Naturally occurring hydrophobic amino acids include alanine, isoleucine, leucine, methionine, phenylalanine, proline, tryptophan and valine. Some less hydrophobic amino acids, including glycine, threonine, and serine, can also constitute part of these sequences (see, e.g., Pallen et al., Trends Microbiol. 9:97-101 (2001)). Hydrophobic sequences generally are between about 10 and about 30 amino acids and sometimes 13 and 24 amino acids in length among available LPXTG (SEQ ID NO:9)-containing substrates for sortase-like proteins (Pallen et al., Trends Microbiol. 9:97-101 (2001)). Exemplary hydrophobic sequences include, e.g., $V^{1740}$GILGLAIATVGSLLGLGV$^{1758}$ (SEQ ID NO:20) in C14 and $P^{1877}$LTAIGIGLMALGAGIFA$^{1894}$ (SEQ ID NO:21) in C370.

Alternatively, the hydrophobic regions of any cell wall anchored protein from a Gram positive bacterium can be used. Alternate hydrophobic sequences include, e.g., those described in FIG. 1 of U.S. Pat. No. 5,821,088 or substantially identical sequences. Additional sequences are also depicted in Table 2 of Pallen et al, *Trends Microbiol.* 9: 97-100 (2001).

D. Charged Sequences

A charge region can be optionally present at the carboxyl terminus of a cell wall targeted protein, typically immediately following the hydrophobic membrane spanning region. The presence of a carboxyl terminal charged region anchors the polypeptide to the membrane, thereby greatly reducing the amount of protein that dissociates from the membrane and escapes into the media. The charged region comprises at least 40%, and in some embodiments, at least 50%, 60%, 70%, 80% or 90%, charged amino acids. Naturally occurring charged amino acids include arginine, histidine, lysine, aspartic acid and glutamic acid. Charged sequences can be between, e.g., 2 and 20 amino acid residues and in some embodiments are between 4 and 12 or between 5 and 11 amino acids in length. Exemplary charged sequences include, e.g., $K^{969}KRKED^{974}$ (SEQ ID NO:22) in C191, $R^{1760}KKRQ^{1765}$ (SEQ ID NO:23) in C14, and $K^{1895}KKRKDDEA^{1903}$ (SEQ ID NO:24) in C370.

Alternatively, the charged regions of any cell wall anchored protein from a Gram positive bacterium can be used. Alternate charged sequences include, e.g., those described in FIG. 1 of U.S. Pat. No. 5,821,088 or substantially identical sequences. Additional sequences are also depicted in Table 2 of Pallen et al, *Trends Microbiol.* 9: 97-100 (2001).

III. Recombinant Techniques

A. Molecular Biology Methods

This invention relies on routine techniques in the field of recombinant genetics. Basic texts disclosing the general methods of use in this invention include Sambrook et al., *Molecular Cloning, A Laboratory Manual* (3rd ed. 2001); Kriegler, *Gene Transfer and Expression: A Laboratory Manual* (1990); and *Current Protocols in Molecular Biology* (Ausubel et al., eds., 1994)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized according to the solid phase phosphoramidite triester method first described by Beaucage & Caruthers, *Tetrahedron Letts.* 22:1859-1862 (1981), using an automated synthesizer, as described in Van Devanter et al., *Nucleic Acids Res.* 12:6159-6168 (1984). Purification of oligonucleotides is by either native acrylamide gel electrophoresis or by anion-exchange HPLC as described in Pearson & Reanier, *J. Chrom.* 255:137-149 (1983).

The sequence of the cloned genes and synthetic oligonucleotides can be verified after cloning using, e.g., the chain termination method for sequencing double-stranded templates of Wallace et al., *Gene* 16:21-26 (1981).

B. Cloning Methods for the Isolation of Nucleotide Sequences Encoding Desired Proteins In general, the nucleic acids encoding the subject proteins are cloned from DNA libraries that are made from cDNA or genomic DNA. The particular sequences can be located by hybridizing with an oligonucleotide probe, the sequence of which can be derived from the sequences disclosed herein or are known in the art, which provide a reference for PCR primers and defines suitable regions for isolating gene-specific probes. Alternatively, where the sequence is cloned into an expression library, the expressed recombinant protein can be detected immunologically with antisera or purified antibodies made against a polypeptide of interest, including those disclosed herein.

Methods for making and screening genomic and cDNA libraries are well known to those of skill in the art (see, e.g., Gubler & Hoffman, *Gene* 25:263-269 (1983); Benton & Davis, *Science,* 196:180-182 (1977); and Sambrook, supra). Cells expressing a protein of interest are useful sources of RNA for production of a cDNA library.

Briefly, to make the cDNA library, one should choose a source that is rich in mRNA. The mRNA can then be made into cDNA, ligated into a recombinant vector, and transfected into a recombinant host for propagation, screening and cloning. For a genomic library, the DNA is extracted from a suitable tissue or cell and either mechanically sheared or enzymatically digested to yield fragments of preferably about 5-100 kb. The fragments are then separated by gradient centrifugation from undesired sizes and are constructed in bacteriophage lambda vectors. These vectors and phage are packaged in vitro, and the recombinant phages are analyzed by plaque hybridization. Colony hybridization is carried out as generally described in Grunstein et al., *Proc. Natl. Acad. Sci. USA.,* 72:3961-3965 (1975).

An alternative method combines the use of synthetic oligonucleotide primers with polymerase extension on an mRNA or DNA template. This polymerase chain reaction (PCR) method amplifies the nucleic acids encoding the protein of interest directly from mRNA, cDNA, genomic libraries or cDNA libraries. Restriction endonuclease sites can be incorporated into the primers. Polymerase chain reaction or other in vitro amplification methods may also be useful, for example, to clone nucleic acids encoding specific proteins and express said proteins, to synthesize nucleic acids that will be used as probes for detecting the presence of mRNA encoding a polypeptide of the invention in physiological samples, for nucleic acid sequencing, or for other purposes (see, U.S. Pat. Nos. 4,683,195 and 4,683,202). Genes amplified by a PCR reaction can be purified from agarose gels and cloned into an appropriate vector.

Appropriate primers and probes for identifying the genes encoding a polypeptide of the invention from tissues or cell samples can be derived from the sequences described in the art. For a general overview of PCR, see, Innis et al. *PCR Protocols: A Guide to Methods and Applications, Academic Press,* San Diego (1990).

A polynucleotide encoding a polypeptide of the invention can be cloned using intermediate vectors before transformation into *Lactobacillus.* These intermediate vectors are typically prokaryote vectors or shuttle vectors.

C. Transformation: Techniques

Appropriate bacterial host strains are selected for, e.g. their transformation ability, ability for heterologous protein expression, and/or ability to colonize on mucosal surfaces. The bacterial host will be rendered competent for transformation using standard techniques, such as the rubidium chloride method or electroporation (see, e.g., Wei, et al., *J. Microbiol. Meth.* 21:97-109 (1995).

Transformation of *L. jensenii* by electroporation can be performed by modifying standard methods as described in, e.g., Luchansky et al. (*J. Dairy Sci.* 74: 3293-3302 (1991); Chang et al., *Proc. Natl. Acad. Sci. USA.* 100:11672-11677

(2003)). Briefly, freshly inoculated *L. jensenii* are cultured in broth (e.g., to 0.6-0.7 at $OD_{600}$ at 37° C. and 5% $CO_2$). The bacterial cells are harvested, washed and re-suspended in a cold (e.g., 4° C.) solution of sucrose and $MgCl_2$. Competent cells are then mixed with DNA and placed in a chilled gap cuvette and electroporated. Afterward, cells are allowed to recover in prewarmed broth (e.g., for about two hours at 37° C.), prior to being plated on selective agar plate containing an antibiotic other selective agent.

D. Expression

Expression cassettes of the invention can include a variety of components to regulate expression and localization of the polypeptides of the invention. For example, expression cassettes can include promoter elements, sequences encoding signal sequences, a coding sequence for the polypeptide of interest and anchor sequences.

Expression of the heterologous polynucleotides or polypeptides can be constitutive (e.g., using P59 (Van der Vossen et al., *Appl. Environ. Microbiol.* 58:3142-3149 (1992)) or P23 (Elliot et al., *Cell* 36:211-219 (1984)) promoters, or *Lactobacillus*-derived native promoters of even higher strength). Alternatively, expression can be under the control of an inducible promoter. For example, the *Bacillus* amylase (Weickert et al., *J. Bacteriol.* 171:3656-3666 (1989)) or xylose (Kim et al. *Gene* 181:71-76 (1996)) promoters as well as the *Lactococcus* nisin promoter (Eichenbaum et al, *Appl. Environ. Microbiol.* 64:2763-2769 (1998)) can be used to drive inducible expression. In addition, acid or alkaline-induced promoters can be used. For example, promoters that are active under the relatively acidic conditions of the vagina can be used. Alternatively, promoters can be used that are induced upon changes in the vagina in response to semen. For example, alkaline-induced promoters are used to induce expression in response to the increased alkaline conditions of the vagina resulting from the introduction of semen.

A variety of signal sequences are known to direct expression of polypeptides to the membrane, extracellular space or the cell wall (e.g., by covalent attachment to peptidoglycan). Exemplary signal sequences include the signal sequence from α-Amylase of *L. amylovorus* (Giraud & Cuny, *Gene.* 198:149-157 (1997)) or the signal sequence from the S-layer gene (cbsA) of *L. crispatus* (e.g., MKKNLRIVSAAAAAL-LAVAPVAA (SEQ ID NO:25) or MKKNLRIVSAAAAAL-LAVATVSA (SEQ ID NO:26). Signal sequences are typically located at the amino-terminus of a polypeptide.

Correct localization and folding of a polypeptide can be determined using standard methods. For example, cell wall enriched fractions of *Lactobacillus* can be obtained by suspending the bacteria in a buffered, solution (e.g., 25% sucrose, 1 mM EDTA, 10 mM Tris-HCl, pH 8.0) followed by treatment with cell wall degrading enzymes (e.g., lysozyme and mutanolysin) and then separating out the resulting protoplasts by differential centrifugation. Fractions can then be screened by western blotting to confirm expression within the cell wall.

Folding and biological activity of an expressed polypeptide can also be determined using standard methods. For example, ELISA assays using antibodies specific for the natively folded polypeptide can be used to confirm folding and three-dimensional structure of the polypeptide. Biological activity assays will of course vary depending on the activity of the polypeptide. For example, for polypeptides that bind to viral proteins, the expressed polypeptide can be tested for its ability to bind a viral protein using standard binding assays. For anti-inflammatory molecules, the expressed polypeptide can be assayed for its ability to antagonize substances that promote inflammation.

When synthesizing a gene for improved expression in a host cell, it is desirable to design the gene such that its frequency of codon usage approaches the frequency of preferred codon usage of the host cell. The percent deviation of the frequency of preferred codon usage for synthetic gene from that employed by a host cell is calculated first by determining the percent deviation of the frequency of usage of a single codon from that of the host cell followed by obtaining the average deviation over all codons.

The polynucleotide sequence encoding a particular polypeptide can be altered to coincide with the codon usage of a particular host. For example, the codon usage of *Lactobacillus* be used to derive a polynucleotide that encodes a polypeptide of the invention and comprises preferred *Lactobacillus* codons. The frequency of preferred codon usage exhibited by a host cell can be calculated by averaging the frequency of preferred codon usage in a large number of genes expressed by the host cell. This analysis is preferably limited to genes that are highly expressed by the host cell. Pouwels et al. (*Nucleic Acids Res.* 36 (1994)), for example, provides the frequency of codon usage by highly expressed genes exhibited by various *Lactobacillus* species. Codon-usage tables are also available via the internet.

IV. Proteins of the Invention

The polypeptides of the invention, e.g., biologically active polypeptides fused to the cell wall targeting regions of the invention) can be any polypeptide. Typically, the polypeptides of the invention are expressed under conditions to allow for biological activity of the polypeptide. In some embodiments, a disulfide bond exists in the expressed polypeptide. In some embodiments, the disulfide bond is required for the poplypeptide's biological activity.

Polypeptides of the invention can be of any size molecular weight. For example, the polypeptides can be between about 100 and 200,000 daltons, between about 500 and 40,000 daltons, between about 500 and 10,000 daltons, between about 10,000 and 50,000 daltons, or about 50,000 and 200,000 daltons.

Examples of classes of polypeptides that can be used according to the methods of the invention to prevent or treat pathogen infection include, e.g., anti-viral polypeptides, anti-bacterial polypeptides, anti-fungal polypeptides, and polypeptides that bind to viruses, bacteria or fungi, including antibodies, antibody fragments, or single-chain antibodies.

In some cases, the polypeptides of the invention will be a receptor that viral or bacterial pathogens bind to infect a host. Alternatively, the polypeptides are agents that, e.g., inhibit pathogen replication, viability, entry or otherwise bind to the pathogen. In some embodiments, the polypeptides of the invention bind or inhibit sexually transmitted pathogens and other pathogens transmitted to or from the vagina. For example, since viruses require binding to a receptor on the target cell surface for infection, strategies directed at inhibiting the interaction of a virus with its host receptor are effective at preventing infection.

Exemplary anti-viral polypeptides include, e.g., CD4 or virus-binding fragments thereof (e.g., 2D-CD4) (e.g., Orloff et al., *J. Virol.* 67:1461-1471 (1993)), stable CD4 trimers formed via a trimeric motif (e.g., Yang et al., *J. Viol.* 76:4634-4642 (2002), a dodecameric CD4-Ig fusion protein (Arthos et al., *J. Biol. Chem.* 277:11456-11464 (2002)), α-defensins (e.g., Zhang et al., *Science* 298:995-1000 (2002), CD4 in fusion with a single chain variable region of the 17b mAb (Dey et al., *J. Virol.* 77: 2859-2865 (2003)), cyanovirin-N or variants (e.g., Bolmstedt et al., *Mol Pharmacol.* 59:949-954

(2001); Mori et al., *Protein Expr. Purif.* 26: 42-49. (2002)), herpes simplex virus entry mediator C (HveC) (e.g., Cocchi et al., *Proc. Natl. Acad. Sci. USA.* 95:15700-15705 (1998)), and ICAM-1. Other embodiments include, e.g., viral receptors or heparin or heparin-like molecules, mannose-binding lectin, including dendritic cell-specific ICAM-3 grabbing nonintegrin (e.g., Geijtenbeek et al., *Cell* 100:587-597 (2000); Feinberg et al., *Science* 294:2163-2166 (2001)), anti-HSV-1 gp120 single-chain antibody (e.g. Marasco et al., *Proc. Natl. Acad. Sci. USA.* 90:7889-7893 (1993); McHugh et al., *J. Biol. Chem.* 277: 34383-34390 (2002)), human mAb b12, recognizing the CD4-binding site of HIV-1 gp120 (e.g. Saphire et al., *Science* 293:1155-1159 (2001)) or other molecules with similar specificity, including neutralizing antibodies that bind to HSV (e.g., Burioni et al., *Proc. Natl. Acad. Sci. USA.* 91: 355-359 (1994)), and HIV-1 entry inhibitory protein (e.g., Root et al., *Science* 291: 884-888 (2001); Sia et al., *Proc. Natl. Acad. Sci. USA.* 99:14664-14669 (2002)).

Infection with human papillomaviruses (HPVs) is a factor that is associated with development of cervical cancer (e.g., zur Hausen, *Virology* 184:9-13 (1991); Stanley, *Best Prat. Res. Clin. Obstet. Gynaecol.* 15:663-676 (2001)). Therefore, the presence of molecules that inhibit or bind to HPV is useful for preventing both HPV infection and the development of cervical cancer. Exemplary anti-HPVs polypeptides include, e.g. neutralizing antibodies that bind human papillomavirus type 16 E6 or E7 protein (e.g. Mannhart et al., *Mol. Cell Biol.* 20:6483-6495 (2000)), HPV-binding proteins, or HPV proteins that can be used to elicit an immune response directed to the virus.

The capacity to bind a pathogen such as a virus or bacteria may be conferred onto the bacteria of the invention in at least several ways. The first is by making the bacteria express on its surface the normal host receptor for the virus, such as ICAM-1 for human rhinovirus HRV (major group) and CD4 for HIV. These are normal human proteins and the complete sequences of many of these genes have been determined and are stored in the database GenBank.

A second method is by expressing on the bacterial surface an antibody fragment or other polypeptide that binds to a conserved determinant on the viral surface, such as VP4 on poliovirus, or gp120 on HIV. Antibody fragments (and peptides) specific for essentially any antigen can be selected, e.g., from a phage-display library (Marks et al., *J. Biol. Chem.* 267:16007-16010 (1992)). Antibodies can be directed to any epitope on or associated with a pathogen as well as other epitopes such as those discussed below.

A third method involves the expression of carbohydrate-binding polypeptides on the surface of the bacteria. Examples of these molecules include heparin-binding polypeptides, or mannose-binding polypeptides.

Anti-bacterial polypeptides include those that bind to or inhibit growth or colonization by uropathogenic *E. coli*. Exemplary anti-bacterial polypeptides include, e.g., permeability-increasing protein against Gram-negative bacteria (Levy. *Expert Opin. Investig. Drugs* 11:159-167 (2002)), mammalian anti-microbial peptides, β-defensins (Ganz & Lehrer. *Pharmacol. Ther.* 66:191-205 (1995), bacteriocins (e.g., Loeffler et al., *Science* 294:2170-2172 (2001)) and antibodies that specifically bind to the bacteria.

Anti-fungal polypeptides include those that bind to or inhibit growth or colonization by fungi such as *Candida*.

Additional examples of biologically-active polypeptides useful according to the invention include therapeutic polypeptides or agents such as anti-inflammatory inflammatory molecules, growth factors, molecules that bind to, or antagonize, growth factors, therapeutic enzymes, antibodies (including, e.g., antibody fragments or single-chain antibodies) and molecules that inhibit or treat cancer including cervical cancer. These examples are not intended to be limiting as numerous other therapeutically active polypeptides can readily be cited.

Anti-inflammatory molecules include, e.g., antibodies or other molecules that specifically bind to TNF or IL-8. Other exemplary anti-inflammatory molecules include IL-10 and IL-11.

Growth factors useful in the invention include, e.g., those involved in local tissue repair such as KGF, HB-EGF, FGF and TGF-β, or antagonists of these molecules.

Therapeutic enzymes include, e.g., nitric oxide (NO) synthase.

Anti-cancer molecules include those that induce apoptosis, that regulate cell cycle such as p53, or that act as a vaccine to target cancer-specific epitopes.

Vaccine molecules useful in the invention include polypeptides that elicit an immune response to viruses, bacteria, or fungi. Exemplary viral vaccines elicit response to, e.g., HIV, HPV, HSV-2, or smallpox. Exemplary antigens include the glycoprotein D of HSV-2, the proteins E6 and E7 of human papilloma virus, the major outer membrane protein of *Chlamydia trachomatis* (Kim and DeMars. *Curr. Opin. Immunol.* 13: 429-436 (2001)), and aspartyl proteases of *Candida albicans* (De Bernardis et al., *Infect. Immun.* 70: 2725-2729 (2002)); FimH of uropathogenic *E. coli* (Langermann et al., *Science.* 276: 607-611 (1997)); IroN of extraintestinal pathogenic *E. coli* (Russo et al., *Infect. Immun.* 71: 7164-9 (2003)).

V. Delivery

Delivery of engineered bacteria to a desired mucosal surface depends on the accessibility of the area and the local conditions. For example, engineered bacteria may be placed in a saline solution or in a foam for delivery onto the vaginal mucosa. Foams can include, e.g., one or more hydrophobically modified polysaccharides such as cellulosics and chitosans. Cellulosics include, for example, hydroxyethyl cellulose, hydroxypropyl cellulose, methyl cellulose, hydroxypropylmethyl cellulose, hydroxyethyl methyl cellulose, and the like. Chitosans include, for example, the following chitosan salts; chitosan lactate, chitosan salicylate, chitosan pyrrolidone carboxylate, chitosan itaconate, chitosan niacinate, chitosan formate, chitosan acetate, chitosan gallate, chitosan glutamate, chitosan maleate, chitosan aspartate, chitosan glycolate and quaternary amine substituted chitosan and salts thereof, and the like. Foam can also include other components such as water, ethyl alcohol, isopropyl alcohol, glycerin, glycerol, propylene glycol, and sorbitol. Spermicides are optionally included in the bacterial composition. Further examples of foams and foam delivery vehicles are described in, e.g., U.S. Pat. Nos. 5,595,980 and 4,922,928.

Alternatively, the bacteria can be delivered as a suppository or pessary. See, e.g., U.S. Pat. No. 4,322,399. In some embodiments, the bacteria of the invention are delivered in a dissolvable element made of dissolvable polymer material and/or complex carbohydrate material selected for dissolving properties, such that it remains in substantially solid form before use, and dissolves due to human body temperatures and moisture during use to release the agent material in a desired timed release and dosage. See, e.g., U.S. Pat. No. 5,529,782. The bacteria can also be delivered in a sponge delivery vehicle such as described in U.S. Pat. No. 4,693,705.

In some embodiments, the bacteria are administered orally. For example, a daily dose of about $10^8$ lactobacilli can be used to restore the normal urogenital flora. See, e.g., Reid et al., *FEMS Immuno. Med. Microbiol.* 32:37-41 (2001).

In some embodiments, applications of engineered bacteria to a mucosal surface will need to be repeated on a regular basis; optimal dosing intervals are routine to determine, but will vary with different mucosal environments and bacterial strain. The dosing intervals can vary from once daily to once every 2-4 weeks.

In embodiments where bacteriophage are introduced to transform native *Lactobacillus*, the nucleic acid of the selected bacteriophage may be manipulated such that the heterologous gene(s) replaces the genes coding for bacteriophage coat proteins, rendering the bacteriophage replication-defective. Adding these recombinant DNA molecules into cell lysates containing functional bacteriophage proteins will lead to assembly of functional bacteriophage particles carrying the heterologous gene(s). These replication-defective bacteriophage particles can then be introduced onto a desired mucosal surface to infect selected floral bacteria. The typical dosage would be $10^8$ to $10^{12}$ PFU/ml applied to the mucosal surface. The proportion of solution to the treated surface should approximate 0.1 to 1.0 ml per square centimeter of mucosal surface. The vehicle would be similar to the vehicle described above for the bacteria.

Example

The following example is offered to illustrate, but not to limit, the claimed invention.

Most viruses are transmitted through mucous membranes—nose, mouth, intestines, or genital tract. These mucous membranes are naturally colonized by vast numbers of commensal bacteria, including *L. jensenii, L. gasseri,* and *L. crispatus,* within the vaginal cavity of healthy women. We envision that genetically modifying *L. jensenii* to express biologically active viral binding proteins that are anchored onto bacterial surface would trap viruses within the mucosa, thus impeding the access of viruses to underlying epithelial cells and lymphocytes. These trapped viruses may undergo an aborted infection process and/or be inactivated locally by antiviral compounds, such as lactic acid and hydrogen peroxide, secreted by the lactobacilli, thereby significantly reducing the numbers of infectious viral particles. Accordingly, we took a modular expression approach to genetically engineered *lactobacillus* for surface expression of high-density HIV-binding ligand, 2-domain CD4 and cyanovirin-N. We discovered that efficient cell wall anchored display of polypeptides from 10 to 600 amino acids could be achieved by fusion to protein domains derived from native proteins of *L. jensenii.*

The M6 proteins have a signature cell wall sorting signal, the LPXTG (SEQ ID NO:9) motif, followed by a stretch of hydrophobic amino acids and finally a sequence containing charged residues (KRKEEN; SEQ ID NO:10), which serves as a critical cell surface retention signal. We initially attempted a plasmid-based modular approach to express CD4 on the surface of *L. jensenii* by utilizing two well-characterized cell-wall anchor motifs, from either the M6 protein (emm6) of *S. pyogenes* or the PrtP protease of *L. paracasei*, or the anchor motif from the M6 protein of *S. pyrogenes* plus an N-terminal 100-amino acid extension (CWA100) derived from the native sequence of M6 protein. Unlike the M6 protein, the sorting signal for PrtP is LPKTA (SEQ ID NO:27). Western analysis of proteins in conditioned media and cell wall- or protoplast-associated protein pools in the modified *L. jensenii* harboring M6 or PrtP or CWA100 as cell wall anchors revealed no detectable cell wall associated 2D CD4, although abundant 2D CD4 was released into conditioned media. Flow cytometric analysis failed to identify positive surface-exposed 2D CD4.

Identification of Putative Cell Wall Anchor Sequences

Database search of genomic sequences of *L. jensenii* allowed identification of approximately 30 contigs with putative cell wall anchor motifs. Based on a more detailed sequence homology search in the non-redundant databases available at the web site of the National Center for the Biotechnology, we selected three of these sequences, designated as C14, C191, and C370. They shared a low sequence similarity (with 23~27% identities) with Rlp of *Lactobacillus fermentum* (Turner et al., *Appl. Environ. Microbiol.* 69:5855-5863 (2003)) or mucus binding protein in *L. reuteri* (Roos and Jonsson, *Microbiol.* 148:433-442 (2002)), a family of streptococcal surface proteins (Wastfelt et al., *J. Bio. Chem.* 271:18892-18897 (1996)), and a cell wall-anchored proteinase in *S. thermophilus* (Fernandez-Espla et al., *Appl. Environ. Microbiol.* 66:4772-4778 (2000)), respectively. All of the three sequences have LPQTG (SEQ ID NO:13) sorting signal preceding a hydrophobic region and a charged C-terminal tail (See FIG. 1). These features are common among sortase-recognized C-terminal cell wall anchor sequences in Gram-positive bacteria (Navarre and Schneewind, *Microbiol. Mol. Bio. Rev.* 63, 174-229 (1999)). Among the LPXTG (SEQ ID NO:9) cell anchor motifs found in Gram-positive bacteria, only seven percent match the LPQTG (SEQ ID NO:13) sequence found in these *L. jensenii* proteins. C14, C191, and C370 proteins all contain tandem repeat domains adjacent to the cell wall anchor region, a structural feature that is frequently present in known cell wall anchored proteins (Navarre and Schneewind, *Microbiol. Mol. Bio. Rev.* 63:174-229 (1999)). The sequences of C14, C191 and C370 are displayed in FIGS. 2A-C.

Epitope Tagging of Putative Cell Wall Anchor Sequences

To determine the efficiency of C14, C191, and C370 to anchor heterologous fusion proteins to the cell wall of *L. jensenii*, we selected approximately 200 amino acids directly N-terminal to LPQTG (SEQ ID NO:13) sorting signal. This region, often defined as cell wall associated (CWA) domain in cell wall anchored proteins, may facilitate retention or extension of substrate sequence and thus proper proteolytic cleavage by membrane-associated sortase. To facilitate immunodetection, c-Myc epitope (EQKLISEEDL; SEQ ID NO:15) was fused with the N-terminus of CWA200 regions of C14, C191, and C370 in pOSEL239, 240, and 241, respectively. Western and flow cytometric analyses were employed to investigate whether the c-Myc tagged proteins were produced and targeted to the cell wall. To perform Western analyses, the modified *L. jensenii* harboring pOSEL175, 239, 240, and 241 were grown in both MRS and Rogosa SL broth to logarithmic phase. Subsequently, the cell walls were digested with mutanolysin, an N-acetyl muramidase that cuts the β1-4 glycosidic bond between MurNAc-GlcNAc of the glycan strands in mature peptidoglycan. Cell wall anchored proteins typically migrate as a large spectrum of fragments, following SDS-PAGE chromatography (Perry et al., *J. Biol. Chem.* 277, 16241-16248 (2002)). Western analysis of proteins in cell wall enriched fractions in the bacterial cells harboring pOSEL239 (C14 anchor) and 241 (C370 anchor) revealed a ladder of c-Myc tagged proteins on reducing SDS-PAGE when the bacterial cells were cultured in both MRS and Rogosa broth (FIG. 3). These patterns were absent in the cell wall enriched fraction in the bacterial cells harboring pOSEL240 (C191 anchor), demonstrating different anchoring efficiencies among LPQTG (SEQ ID NO:13)-containing sequences tested.

To determine whether the Western blot positive c-Myc epitope is surface exposed in the *L. jensenii* cells harboring pOSEL239 and 241, flow cytometric analysis of the binding of anti-c-Myc antibody was performed, in reference to the bacterial cells harboring control plasmid pOSEL175. While mean fluorescence intensity in bacterial cells harboring pOSEL239 was not distinguishable from those harboring control plasmid pOSEL175, it increased 160 fold in the bacterial cell harboring pOSEL241. While it is unclear whether steric hindrance affects the surface accessibility of c-Myc tagged CWA200 region of C14 sequence, our analysis clearly demonstrated surface exposure of the extreme N-terminus of CWA200 region of C370 sequence. This result demonstrates that this particular region of C370 can be exploited to covalently anchor heterologous peptides and proteins to the bacterial cell surface.

Surface Expression of 2D CD4 on Bacterial Surface of *L. jensenii*

Figure 4:
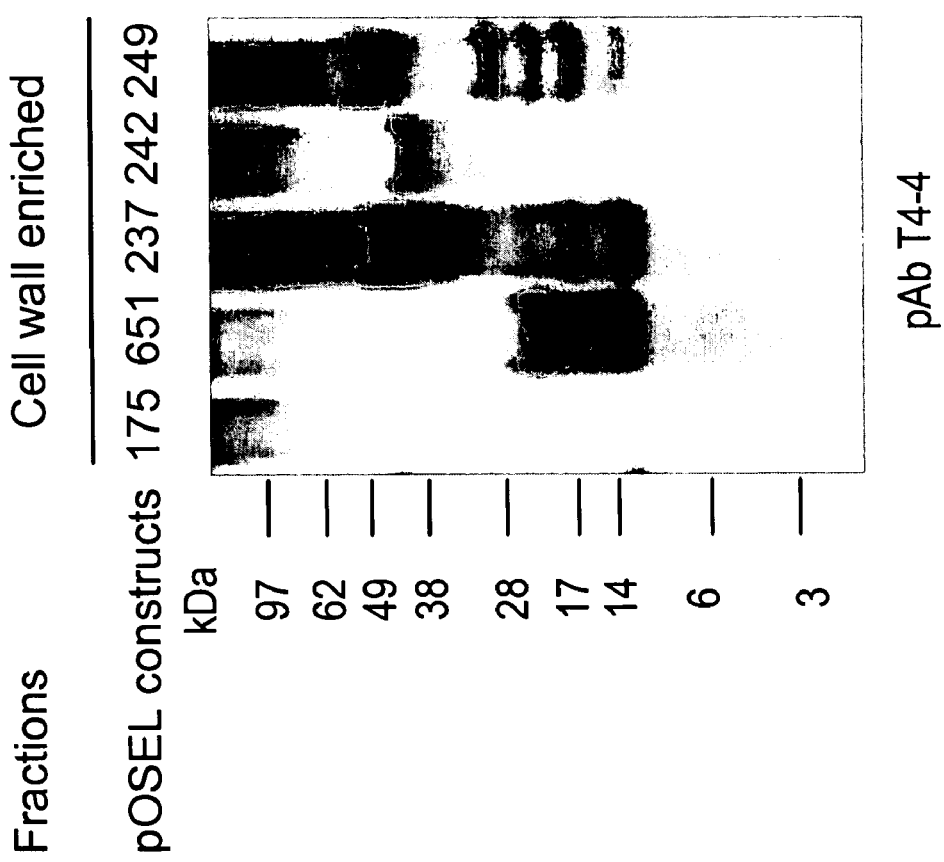
FIG. 4 illustrates results from western analysis of cell wall enriched fractions following mutanolysin digestion of transformed L. jensenii 1153 when cultured in Rogosa SL broth at 37° C. and 5% $CO_2$. After separation in reducing SDS-PAGE, the proteins were electroblotted to PVDF membrane for probing with polyclonal antibodies (pAb) against CD4 (T4-4). The expression constructs contained the following elements: $P_{23}$ promoter-CbsA signal sequence (CbsAss)-2D CD4 in pOSEL651; $P_{23}$ promoter-CbsAss-2D CD4-CWA200-anchor of C14 sequence in p237; $P_{23}$ promoter-CbsAss-2D CD4-CWA200-anchor of C191 sequence in pOSEL242; $P_{23}$ promoter-CbsAss-2D CD4-CWA200-anchor of C370 sequence in pOSEL249. CWA200 represents approximately 200 amino acids upstream of C-terminal anchor domain.

We performed Western blotting and flow cytometry analyses, to determine whether 2D CD4 can be surface expressed via the CWA200 region of C14 and C370 sequences. To perform Western analysis, proteins in *L. jensenii* cells harboring pOSEL175 (control plasmid), 651 (2D CD4 plasmid without a cell anchor) (Chang et al., *Proc. Natl. Acad. Sci. USA*. 100:11672-11677 (2003)), 237 (2D CD4 fused to C14 anchor), 242 (2D CD4 fused to C191 anchor), and 249 (2D CD4 fused to C370 anchor), were fractioned into cell wall enriched fractions upon cell wall digestion. In cell wall enriched protein fractions, a spectrum of higher molecular weight species were immunoreactive to pAb T4-4 in both bacterial cells harboring pOSEL237 and 249, but not in pOSEL651 (FIG. 4). Such observed ladder patterns on SDS-PAGE following mutanolysin digestion resemble the patterns of known cell wall anchor proteins from bacterial surface of other Gram-positive bacteria (Perry et al., *J. Biol. Chem.* 277:16241-16248 (2002)).

To determine whether 2D CD4 is expressed on cell surface, the *L. jensenii* strains harboring pOSEL175, 651, 237, and 249 were probed with pAb T4-4 and subsequently analyzed for antibody binding by flow cytometric analysis. As expected, this analysis revealed indistinguishable mean fluorescence intensity in bacterial cells harboring pOSEL175 and 651. In contrast, there was significant increase in mean fluorescence intensity in bacterial cells harboring pOSEL237 and 249 relative to pOSEL175 and 651, likely as a result of covalent attachment and surface exposure of 2D CD4 molecules (FIG. 5A). To further validate the above approach, a recoded cyanovirin-N (CV-N) gene, containing *Lactobacillus*-preferred codons, was fused to the same C-terminal anchor domains that were used for successful anchoring of 2D-CD4. Flow cytometry analysis of modified *L. jensenii* harboring CV-N expression plasmids detected a 30-50 fold increase in mean fluorescence intensity relative to bacteria harboring pOSEL175 (data not shown). To investigate the possibility that the antibody reactive CV-N molecules were surface associated via electrostatic interactions, the modified bacteria were extracted with 5 M LiCl. Flow cytometric analysis revealed indistinguishable mean fluorescence intensity in salt extracted *L. jensenii* harboring CV-N expression plasmids in reference to those washed with PBS and 2% FBS. Resistance of surface displayed CV-N molecules to extraction by 5 M LiCl reflects a behavior of covalently anchored proteins on bacterial surfaces.

To address whether surface expressed 2D CD4 molecules adopt correctly folded conformation for binding gp120, additional FACS analyses were performed after bacterial cells harboring pOSEL175, 237, and 249 were probed with anti-CD4 monoclonal antibody, Sim.4, which recognizes a conformational dependent epitope. There was a significant increase in mean fluorescence intensity in the bacterial cells harboring pOSEL237 and 249 relative to pOSEL175, demonstrating that 2D CD4 were expressed in a functional form on the surface of *L. jensenii* (FIG. 5B).

It was unclear whether surface expression of 2D CD4 in a modular expression approach would affect expression of native cell surface associated proteins in modified *L. jensenii*. To address this issue, bacterial cells harboring pOSEL175 and 237 were probed with sulfo-NHS-biotin, and subsequently cell surface associated proteins were extracted in a buffer containing 0.4% SDS and 10 mM DTT. Western analysis of SDS-extracted proteins after probing with alkaline phosphatase conjugated avidin detected spectrum of biotinylated proteins with apparent molecular masses from 10 to >200 kDa. The pattern of resolvable biotinylated protein species in the bacterial cells harboring pOSEL237 was similar to those in pOSEL175, indicating that native cell surface expression was not affected.

Surface Expression of Active 2D CD4 at Wide pH Range in *L. jensenii*

The human vaginal cavity, when naturally colonized with *lactobacillus*, has a pH that varies from 3.6 to 4.5 in most women (Boskey et al., *Infect. Immun.* 67: 5170-5175 (1999)), and transiently becomes neutral or weak alkaline when the male ejaculate is present. Experiments were performed to examine how pH changes would affect surface expression of an active 2D CD4 molecule in the modified *L. jensenii*. Bacterial cells were inoculated into Rogosa SL broth, either at its commonly used pH (5.4) or buffered with 100 mM HEPES, pH 7.4. The pH of the culture medium did not change substantially during active growth to $OD_{600}$ at ~0.4. Flow cytometric analysis of binding of mAb Sim.4 to bacterial cells harboring pOSEL237 and 249 detected significantly higher mean fluorescence intensity above control background in pOSEL175 at both pH 5.4 and 7.4. Furthermore, the level of surface-expressed CV-N remained elevated when the modified *L. jensenii* were cultured at acidic pH's that resemble those found within the human vaginal cavity (data not shown).

Lack of Surface Display of 2D CD4 when Expressed in Fusion Solely Via C-Terminal Anchor Motif of 36 Amino Acid in Length It is unclear whether a 36 amino acid C-terminal anchor motif, including LPQTG (SEQ ID NO:13) signal, a hydrophobic region, and a charged tail of C14 or C370 sequence would be sufficient to support efficient surface expression of 2D CD4 in the *L. jensenii*. To address this question, two constructs, designated as pOSEL238 harboring the C-terminal anchor motif of C14 and pOSEL262 harboring the C-terminal anchor motif of C370 were prepared and analyzed in reference to negative controls pOSEL175 and 651, and positive control, pOSEL237. Western analysis of cell wall enriched fraction in *L. jensenii* harboring pOSEL238 after probing with pAb T4-4 detected no ladder patterns resembling those in pOSEL237. Furthermore, flow cytometric analysis of mAb Sim.4 binding to bacterial cells harboring pOSEL238 failed to detect any increase in mean fluorescence intensity relative to background control in cells harboring pOSEL175 (FIG. 6). Similarly, FACS analysis of the bacterial cells harboring pOSEL262, in reference to those harboring pOSEL175 and positive control pOSEL249, yielded similar negative results. Consistent with these observations, surface expression of 2D CD4 was not achieved when similar length of C-terminal anchor motifs from S. pyogenes and L. paracasei were employed. This suggests that protein sequences upstream from the characteristic LPQTG (SEQ ID NO:13) motif contribute significantly to the cell wall anchoring process and are required to display biologically active proteins on the cell wall of L. jensenii.

Figure 7:
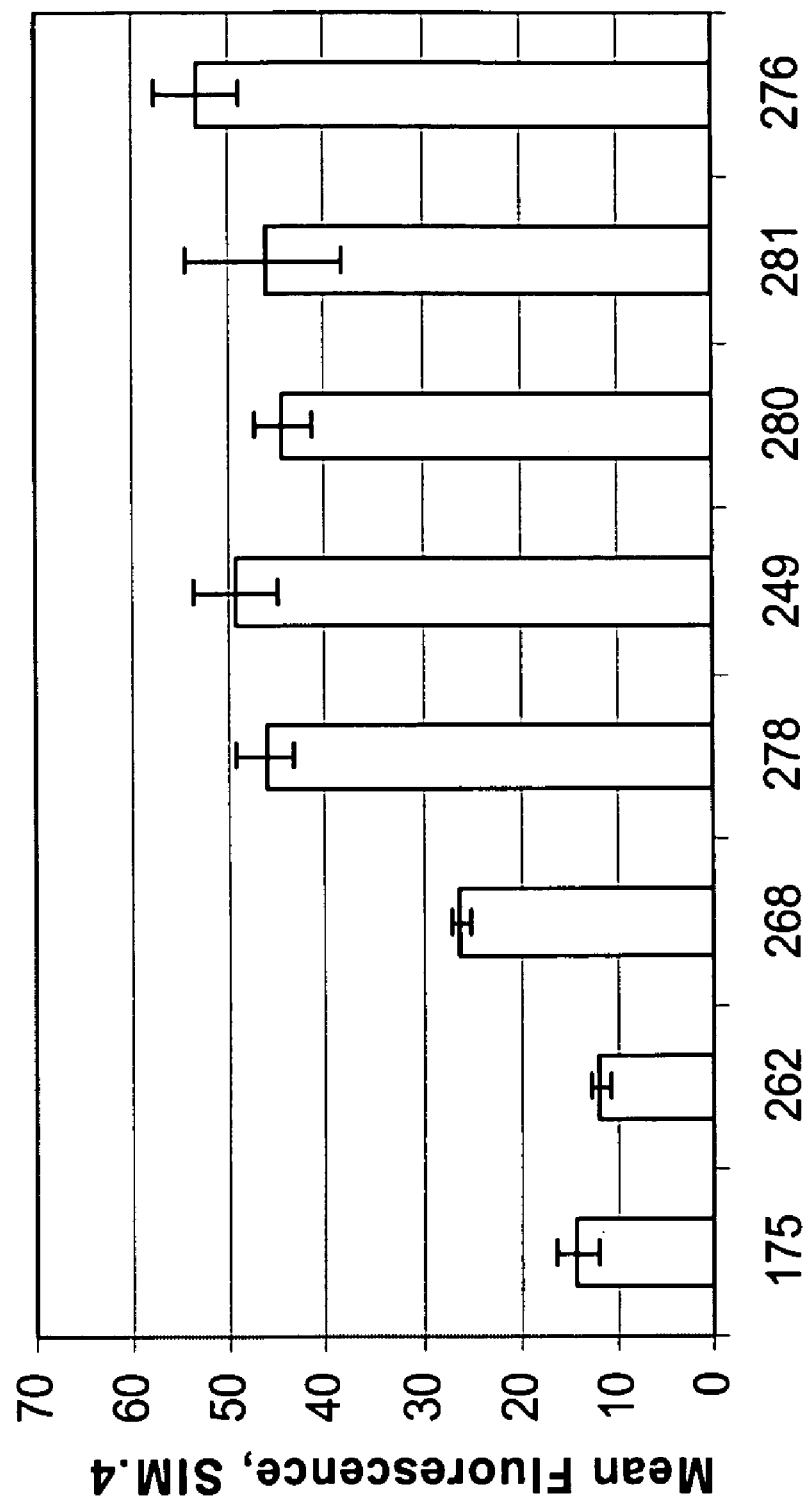
FIG. 7 illustrates the surface expression of 2D CD4 in L. jensenii 1153 as affected by different number of the repetitive cell wall spanning sequence upstream of the LPQTG (SEQ ID NO:13) sorting signal in C370 sequence. Surface exposed 2D CD4 molecules that adopt a correctly folded conformation were probed with mAb Sim.4 for flow cytometric analysis in the bacterial cells harboring the following plasmid: 175, a negative control; 249, two and a half repeats; 262, no repeat; 268, one repeat; 278, two repeats; 280, four repeats; 281, seven repeats; 276, eight repeats.

Requirement of a Defined Length of Repetitive Cell Wall Spanning Sequence Upstream of the LPQTG Motif for Optimal Surface Display of Biologically Proteins The native C370 sequence contains eight nearly identical tandem repeats, a characteristic of many cell wall anchor proteins in Gram-positive bacteria, in its C-terminal region upstream of the LPQTG (SEQ ID NO:13) motif (FIG. 1). While two and half repeat sequences were included in the anchoring sequence of pOSEL249, it remains to be determined whether a different length of upstream sequence could be used to maximize surface protein display. Accordingly, several constructs were prepared harboring 0, 1, 2, 4, 7, and 8 repeats of the C370 sequence. They were designated as pOSEL262, 268, 278, 280, 281, 276, respectively. To determine level of 2D CD4 molecules that adopt a correctly folded conformation, the transformed bacteria were probed with mAb Sim.4 for flow cytometry analysis (FIG. 7). There was non-distinguishable mean fluorescence intensity in bacterial harboring pOSEL262 (0 repeat) from that in negative control pOSEL175, suggesting the requirement of repetitive sequence for proper surface expression of heterologous proteins. In addition, there was a significant increase in fluorescence intensity when number of repeats increased from 0 in pOSEL262 up to 3 in pOSEL278. The fluorescence intensity remained steady with additional increase in number of repeats.

Figure 8:
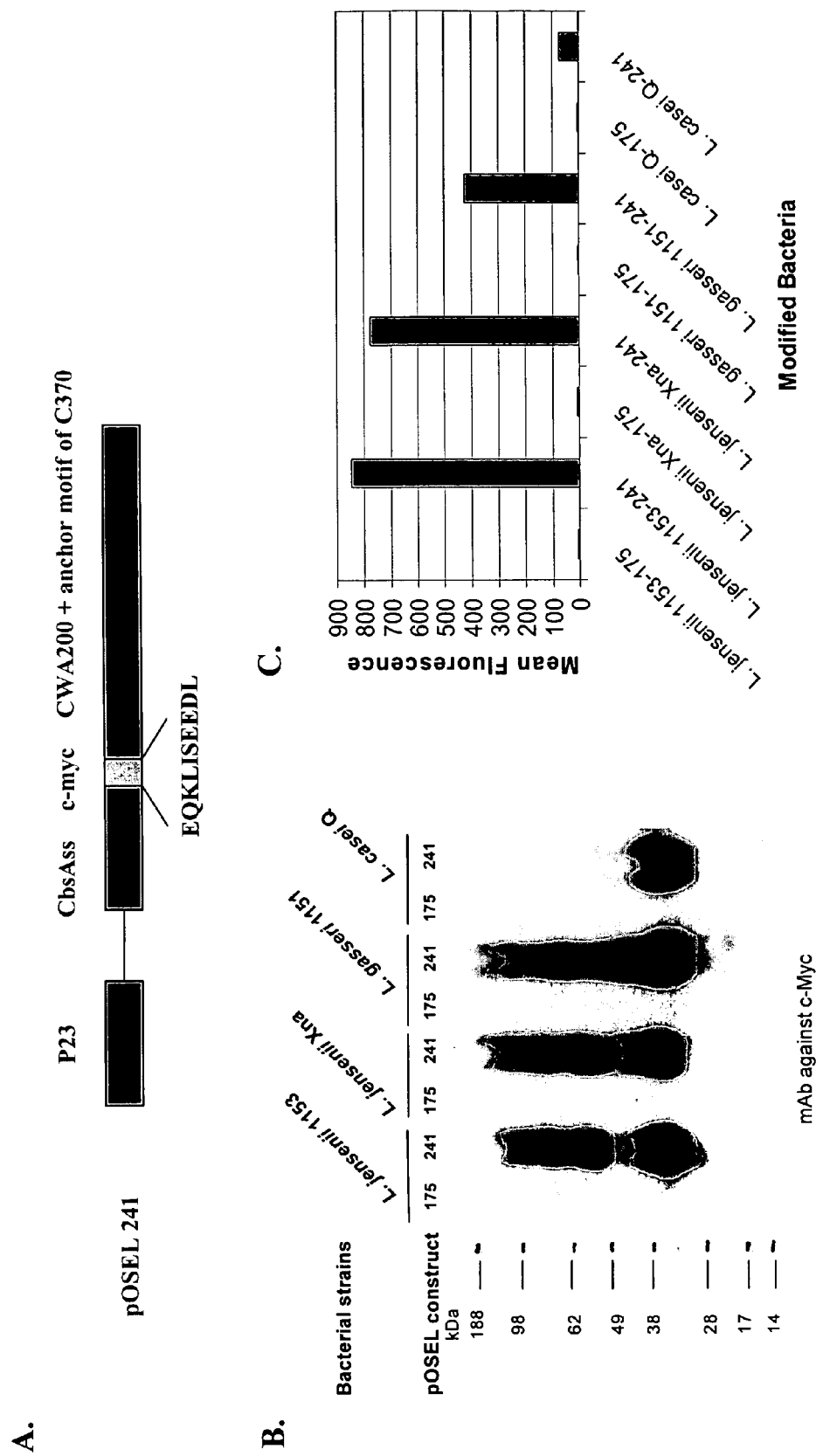
FIG. 8 illustrates the surface display of c-Myc tagged proteins in a variety of lactobacillus species of human origin. (A). Schematic of pOSEL241 designed for expression of c-Myc tagged CWA200 of C370 sequence under control of P23 promoter and CbsA signal sequence (CbsAss). cNyc epitope EOKLISEEDL=SEQ ID NO:15. (B). Western analysis of cell wall enriched fractions following mutanolysin digestion of transformed L. jensenii, L. gasseri, and L. casei. After separation in reducing SDS-PAGE, the proteins were electroblotted to PVDF membrane for probing with mAb against c-Myc. (C). Flow cytometric analysis of human vaginal lactobacillus isolates harboring pOSEL241. The bacterial cells were probed with mAb against c-Myc, and then phycoerythrin (PE)-conjugated anti-mouse antibodies. Controls consisted of unstained cells or cells probed with PE-conjugated secondary antibodies.

Utility of Native Anchor Sequences of L. jensenii in Supporting Surface Display of Proteins in a Variety of Lactobacillus Species To determine whether the anchor sequences of C370 native to L. jensenii 1153 could afford protein surface display in other L. jensenii strains or lactobacillus species of human origin, pOSEL175 or pOSEL241, that was designed to fuse c-Myc epitope to CWA200 of C370 sequence (FIG. 8A), were introduced into L. jensenii Xna, L. gasseri 1151, and L. casei Q by electroporation. The transformed bacteria were analyzed by Western and flow cytometric analyses, in reference to positive control L. jensenii 1153 harboring pOSEL241. Western analyses of cell wall digests following probing with mAb against c-Myc detected laddering patterns in transformed L. jensenii Xna and L. gasseri 1151 harboring pOSEL241 that were similar to those in L. jensenii 1153, and to a lesser extent in L. casei Q (FIG. 8B). Flow cytometric analyses following immunostaining of the bacterial cells with mAb against c-Myc detected a low level of fluorescence in all lactobacillus species harboring pOSEL175 (FIG. 8C), but an elevated increase in fluorescence intensity in L. jensenii Xna and L. gasseri 1151 harboring pOSEL241 as result of binding of the antibody binding to surface displayed c-Myc epitope. Additionally, there was still approximately 19 fold increase in fluorescence intensity of L. casei Q harboring 241 relative to that of L. casei harboring pOSEL175. Taking these data together, the anchor sequence native to L. jensenii 1153 clearly exhibit a broad utility in supporting surface display of proteins in a variety of lactobacillus species, including those of human origin.

Effect of Mutagenesis of LPXTG (SEQ ID NO:9) Motif on Surface Expression of 2D CD4 in L. jensenii When protein A of Staphylococcus aureus, a well studied cell wall anchor protein, was mutated on the LPETG (SEQ ID NO:28) cell wall sorting motif, it was found that replacing amino acid proline (P) in LPQTG (SEQ ID NO:13) with amino acid asparagine (N) decreased the efficiency of protein surface display, while replace threonine (T) with serine (S) had little effect on the efficiency of protein surface display (Navarre and Schneewind, Microbiol. Mol. Biol. Rev. 63:174-229 (1999)). This study indicated that the P residue is probably the most important residue in LPXTG (SEQ ID NO:9) motif, and the T residue can be replaced by a similar amino acid, S. To determine whether the LPQTG (SEQ ID NO:13) motif within the C14 and C370 is indeed the critical sorting signal, the importance of P and T within the LPQTG (SEQ ID NO:13) sequence was investigated. Point mutations were generated within the LPQTG (SEQ ID NO:13) motif by PCR on both C14 and C370 sequences. The P residue was mutated to alanine (A) or asparagine (N); the amino acid T was mutated to A, S or glycine (G); the amino acid G in the LPXTG (SEQ ID NO:9) motif was mutated to A. Plasmids with the altered LPQTG (SEQ ID NO:13) motif were designated as pOSEL237P(A), pOSEL237P(N), pOSEL237T(A), pOSEL237T(G), pOSEL237T(S), pOSEL237G(A), pOSEL249P(A), pOSEL249P(N), pOSEL249T(A), pOSEL249T(G), pOSEL249T(S), and pOSEL249G(A), respectively. Western and flow cytometric analyses of the L. jensenii 1153 harboring the mutated constructs were performed. Compared to the L. jensenii harboring parental pOSEL237 and pOSEL249, those harboring pOSEL237P(A), pOSEL237P(N), pOSEL249P(A), and pOSEL249P(N) did not exhibit the characteristic higher molecular weight species spectra, upon Western blotting of cell wall enriched protein fractions with pAb T4-4. Instead, there was a marked increase in secretion of 2D CD4-CWA200 fusion protein into the conditioned medium, indicating that the 2D CD4-CWA200 fusion proteins were not covalently linked to the cell wall. A characteristic spectra of higher molecular weight species, similar to those observed with wild type pOSEL237 and pOSEL249, was evident upon cell wall digestion of L. jensenii harboring pOSEL237T(S) and pOSEL249T(S), suggesting that the amino acid T within LPQTG (SEQ ID NO:13) from C14 and C370 can be effectively replaced by S (data not shown).

Figure 9:
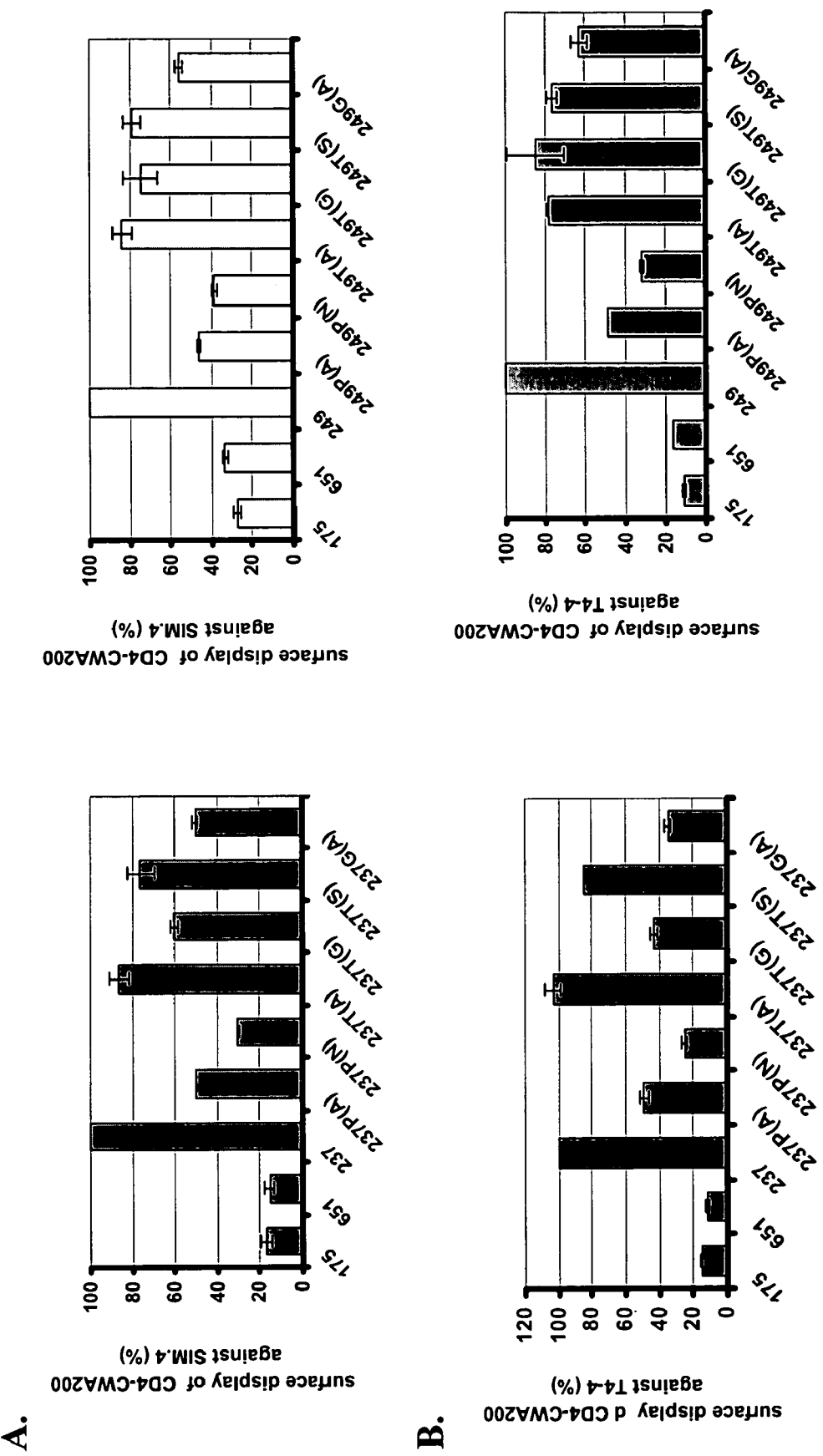
FIG. 9 illustrates the effect of point mutations in the LPQTG (SEQ ID NO:13) motif of C14 and C370 sequences on the surface display of 2D-CD4-CWA200 in L. jensenii 1153. Bacterial cells were surface-stained by using pre-titered mAb Sim.4 (A) or pAb T4-4 (B), followed by probing with PE-conjugated anti-mouse or FITC conjugated anti-rabbit antibodies. The flow cytometric analysis was performed in a FACScalibur system. The difference between the protein displayed on the cell surface of pOSEL237, pOSEL249, and those in bacterial cells harboring mutagenic constructs was expressed in mean fluorescence intensity. The surface display of 2D CD4 in the bacterial cells harboring pOSEL237 or pOSEL249 was arbitrarily set as 100%.

To further determine the effect of mutagenesis of LPXTG (SEQ ID NO:9) on L. jensenii surface protein display, the L. jensenii strains harboring pOSEL175, 651, 237, 249, along with the various mutant constructs, were probed with pAb T4-4 or mAb Sim.4, and subsequently analyzed for antibody binding by flow cytometry. There was a substantial decrease of mean fluorescence intensity in bacterial cells harboring pOSEL237P(A), pOSEL237P(N) compared to pOSEL237, and for pOSEL249P(A), pOSE1249P(N) comparing to those harboring pOSEL249, indicating that there was much less 2D CD4 protein displayed on the cell surface, if any. However, the mean fluorescence intensity in the bacterial cells harboring pOSEL237T(S), pOSEL 237 (T)A, pOSEL249T(S), and pOSEL249 (T)A was comparable to L. jensenii harboring pOSEL237 and 249, demonstrating that replacing T with S or A has little effect on the efficiency of cell wall anchoring (FIG. 9).

The data from Western blot and flow cytometric analysis indicate that the amino acid P contained within LPQTG (SEQ ID NO:13) motif of C14 and C370 can not be readily substituted. In contrast, the amino acid T can be replaced with S or A, yielding a protein that still anchors efficiently to the cell wall of Lactobacillus.

Figure 10:
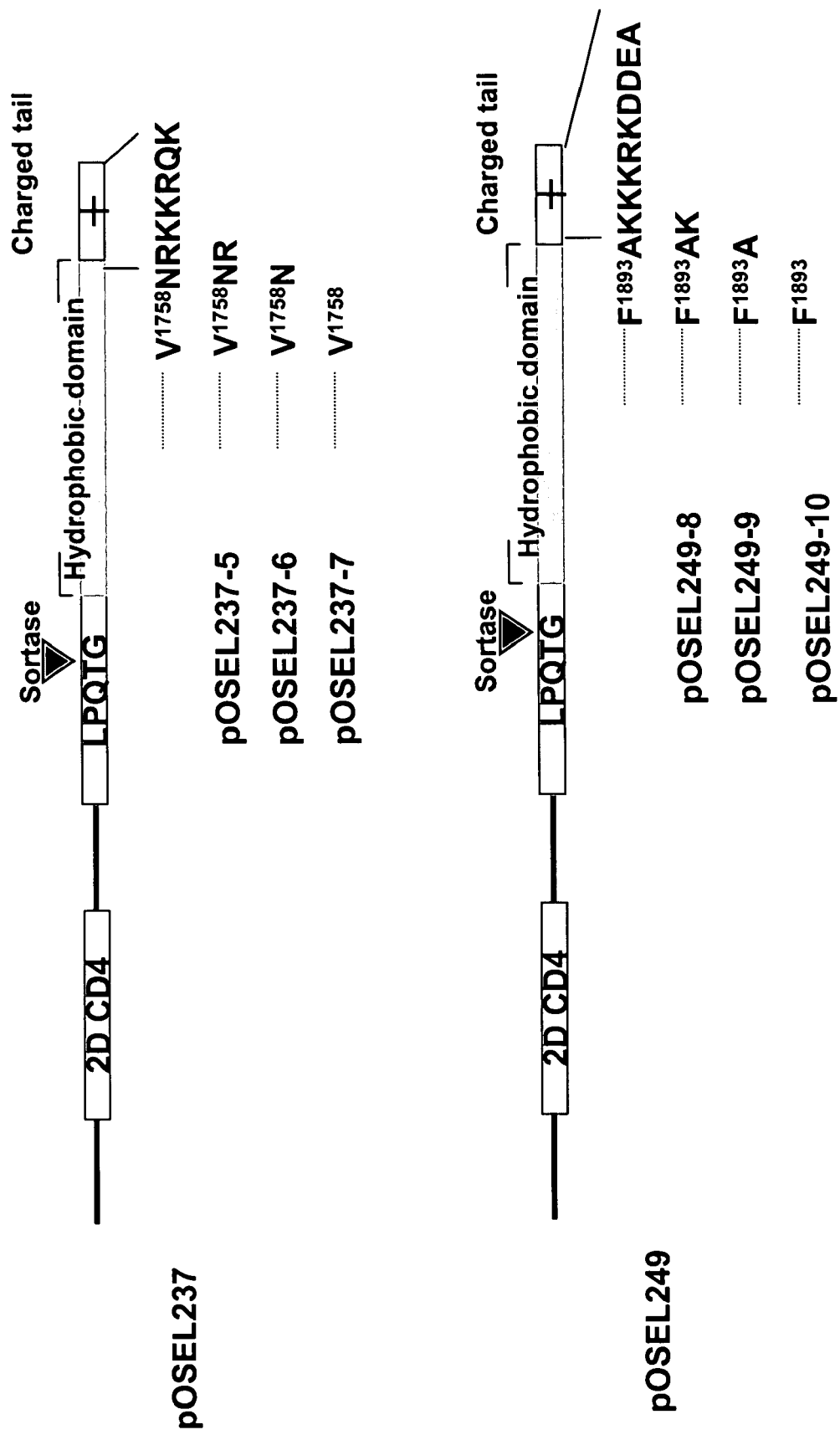
FIG. 10 illustrates schematic diagram of deletion constructs in C-terminal charged tails (SEQ ID NOS:16 and 17) of C14 and C370 sequences. LPQTG=(SEQ ID NO:13).

Effect of Deletion of C-terminal Positive Charged Tail on Surface Expression of 2D CD4 in L. jensenii One of the characteristics of gram-positive cell wall anchor domains is the stretch of positive charged amino acids at the extreme C-terminus of the protein. In the M6 proteins, this sequence (KRKEEN; SEQ ID NO:10) serves as a critical cell surface retention signal. These signature sequences have been found in other Gram-positive bacteria including *Staphlyococcus, Enterococcus, Listeria*, and *Lactobacillus* (Navarre and Schneewind, *Microbio. Mol. Biol. Rev.* 63:174-229 (1999)). Two sequences RKKRQK$^{1765}$ (SEQ ID NO:23) and KKKRKDDEA$^{1903}$ (SEQ ID NO:24) were identified as the positive charged tails in C14 and C370 putative anchor sequences respectively (FIG. 1). To determine whether theses two sequences serve as cell surface retention signal, a series of deletion constructs were created (FIG. 10). They were designated as pOSEL237-5, pOSEL237-6, pOSEL237-7, pOSEL249-8, pOSEL249-9, and pOSEL249-10, respectively.

Western and flow cytometric analyses of *L. jensenii* harboring these constructs were performed. Protein species migrating at 48 kDa, representing the 2D CD4 in fusion with CWA200, can be detected by the pAb T4-4 in all the *L. jensenii* harboring the charged-tail knockout constructs, following SDS-PAGE. The secreted proteins were more abundant in *L. jensenii* cells harboring pOSEL237-5, pOSEL237-6, pOSEL237-7, pOSEL249-8, pOSEL249-9, and pOSEL249-10 than the cells harboring the parental pOSEL237 and 249. Western analysis of the proteins in the cell wall enriched fractions from all of the deletion mutants failed to detect the characteristic ladder patterns that were observed in *L. jensenii* harboring pOSEL237 or 249 (data not shown). These data suggested that the 2D CD4-CWA200 fusion proteins were not covalently linked to the cell wall.

Figure 11:
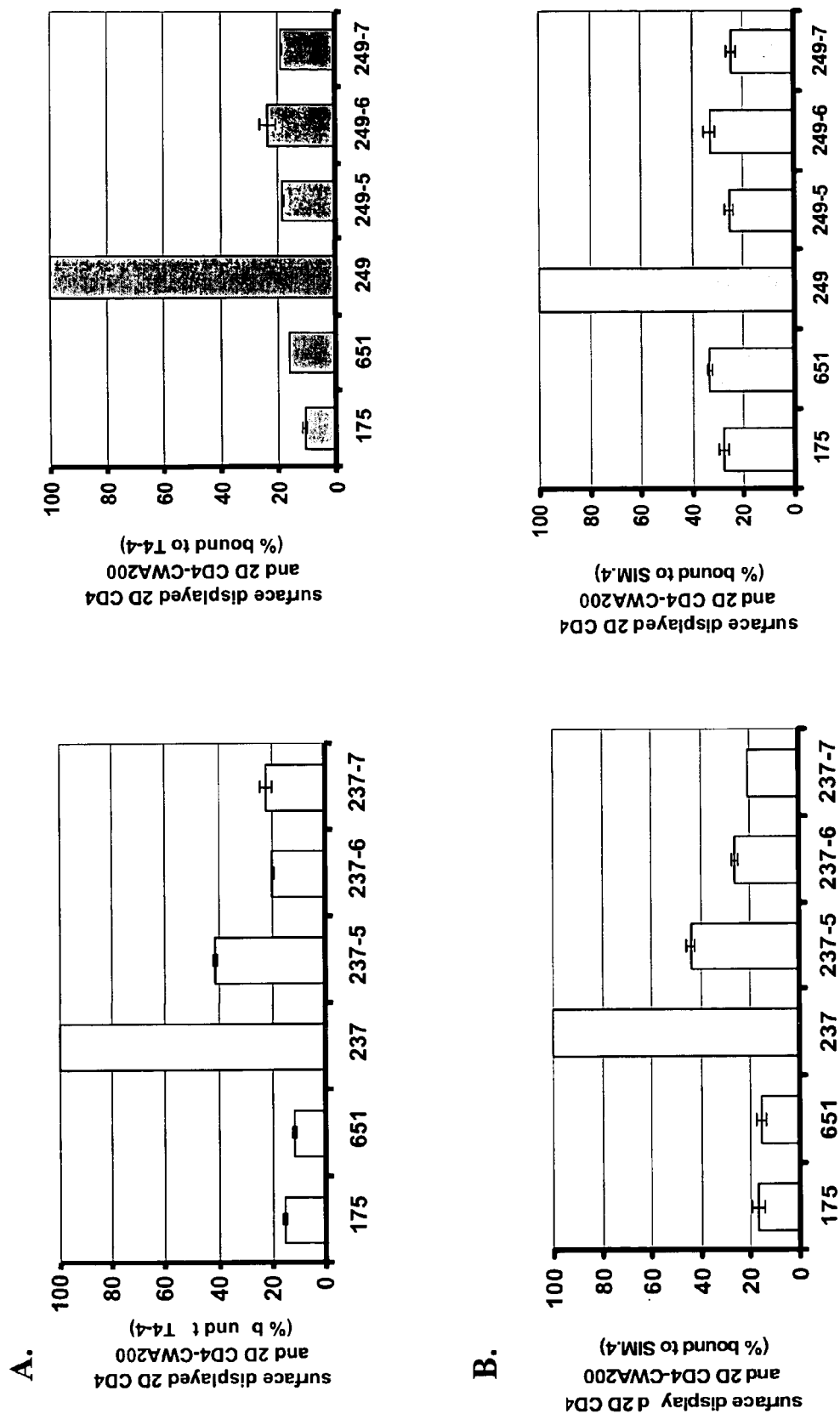
FIG. 11 illustrates the effect of sequence deletion in the C-terminal charged tails of C14 and C370 on the surface display of 2D CD4-CWA200. Bacterial cells were surface-stained by using pre-titered pAb T4-4 (A) or mAb Sim.4 (B), followed by probing with FITC conjugated anti-rabbit or PE-conjugated anti-mouse antibodies. The binding of antibody to cell wall anchored proteins was analyzed by flow cytometry using a FACScalibur system. The difference between the protein displayed on the cell surface of pOSEL237 or pOSEL249 and those in bacterial cells harboring mutagenic constructs was expressed as mean fluorescence intensity. The surface display of 2D CD4 in the bacterial cells harboring pOSEL237 or pOSEL249 was arbitrarily set as 100%.
Figure 12:
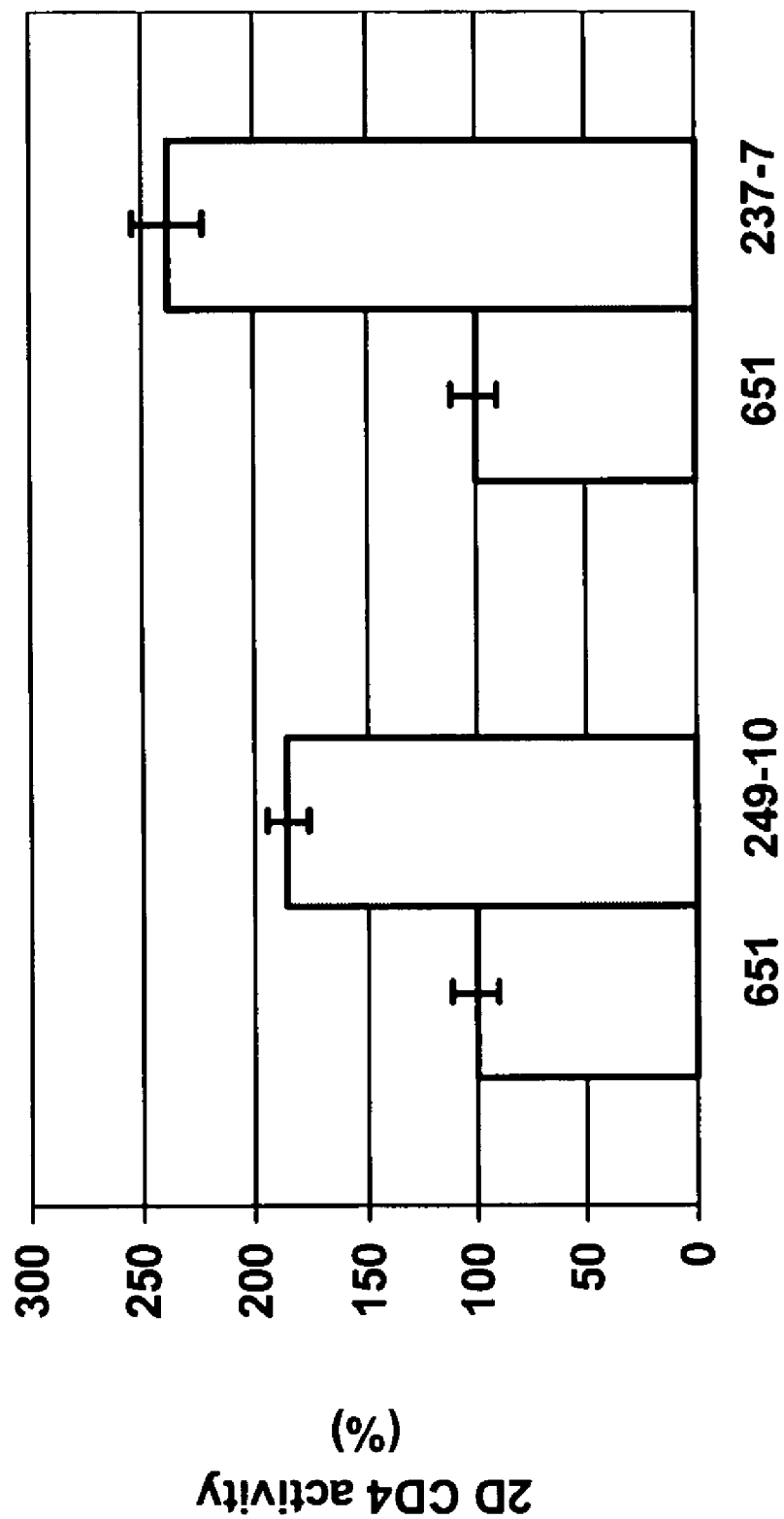
FIG. 12 illustrates a comparison of activities of secreted 2D CD4-CWA200 in L. jensenii 1153 harboring pOSEL237-7 and pOSEL249-10 relative to 2D CD4 from those harboring pOSEL651. CD4 ELISA was designed to recognize proteins that adopt a correct, properly-folded conformation in cell-free conditioned media. Amounts of proteins were normalized based on their immunoreactivity to pAb T4-4. The soluble 2D CD4 proteins released from the bacterial cells harboring pOSEL651 was arbitrarily set as 100%.

Flow cytometric analysis of modified *L. jensenii* following probing with anti-CD4 pAb T4-4 or mAb Sim.4 detected a marked decrease of mean fluorescence intensity in the bacterial cells harboring these mutant plasmids relative to those harboring parental pOSEL237 or 249 (FIG. 11). These data demonstrated conclusively that deletion of the positively charged C-termini of both C14 and C370 inhibited their ability to anchor to the cell wall and display heterologous proteins.

Flexibility of LPQTG Motif as a Cell Wall Anchor Signal

While most cell wall anchored proteins from Gram-positive bacteria share the same sorting signal LPXTG (SEQ ID NO:9), some of the proteins, however, have different motifs. The sorting signal for PrtP of *L. paracasei*, for example, is LPKTA (SEQ ID NO:27) (Holck and Naes. *J Gen. Microbiol.* 138:1353-1364 (1992)). Protein L and the human serum albumin binding protein of *Peptostreptococcus magnus* share a motif of LPXAG (SEQ ID NO:29) (de Château & L. Björck. *J. Biol. Chem.* 269:12147-12151 (1994); Keller et al., *EMBO J.* 11:863-874 (1992); Murphy et al. *DNA Seq.* 4: 259-265 (1994)). When LPQTG (SEQ ID NO:13) mutated to LPQAG (SEQ ID NO:12) or LPQSG (SEQ ID NO:11) in C14 or C370 anchor proteins, there was only a slight decrease in surface display of 2D CD4, as measured by flow cytometry or Western blotting following SDS-PAGE. However, these sequences alone are insufficient to anchor proteins to the cell wall of vaginally derived lactobacilli as based on the following evidence: 1) the 36-amino acid C-terminal anchoring domain alone did not anchor c-Myc epitope, or 2D CD4 to the cell surface, 2) the prototypical M6 cell wall anchor sequence (encoded by the emm6 gene of *S. pyogenes*) did not anchor heterologous proteins to the cell wall of vaginally derived lactobacilli, even when upstream sequences of up to 200 amino acids are included (we found a similar result when using the LPXTA (SEQ ID NO:30) motif from *L. paracasei*), and 3) the C191 protein was not an efficient anchor. These findings demonstrate that other upstream sequences contained within the CWA200 region of C14 and C370, also contribute significantly to the cell wall anchoring process.

Enhancement of 2D CD4 Biological Activity When Fused with CWA200 of C14 and C370

In order to assess biological activity, the 2D CD4-CWA200 of C14 and C370 proteins released from *L. jensenii* 1153 harboring pOSEL237-7 and pOSEL249-10 were analyzed by CD4 ELISA. The bacterial cells harboring pOSEL651, pOSEL237-7, and pOSEL249-10 were grown in Rogosa SL broth to different cell densities. Then, the cell-free conditioned media were harvested. At $OD_{600}=0.8$, there was similar amount of 2D CD4 from pOSEL651 and 2D CD4-CWA200 from pOSEL237-7 or 249-10 released into the medium as measured by Western blot. Nevertheless, the 2D CD4-CWA200 released from the bacterial cells harboring pOSEL237-7 and pOSEL249-10 exhibited about 2-3 fold of more activity when compared to the 2D CD4 protein from those harboring pOSEL651. The fusion of CWA200 region of C14 or C370 to 2D CD4 appeared to enhance the biological activity of the protein, probably by assisting the protein folding process. This same finding has been confirmed using a gp120 binding assay (data not shown). Western blot analysis of these proteins suggests that 2D CD4-CWA200 is significantly more stable than 2D CD4, perhaps contributing to its enhanced biological activity.

Materials and Methods

Bacterial Strains and Culture

Human vaginal strains of *L. jensenii, L. crispatus, L. gasseri* and *L. casei* were isolated by bacterial culture of vaginal samples obtained from healthy women. The bacterial strains were genotyped against DNA sequence of reference strains held in GenBank after amplification of 16S-23S intergenic spacer region using two primers specific to lactobacilli rRNA (Tannock et al. *Appl. Environ. Microbiol.* 65:4264-4267 (1999)). The strains were routinely grown in MRS or Rogosa SL broth (Difco, Detroit, Mich.) or on MRS agar plate at 37° C. and 5% $CO_2$.

Isolation of the Genomic DNA of *Lactobacillus jensenii* 1153

Chromosomal DNA of *L. jensenii* 1153 was isolated based on modifications of a protocol that previously used to isolate chromosomal DNA from *L. crispatus* JCM 5810 (Sillanpaa et al., *J. Bacteriol.* 182:6440-6450 (2000)). *L. jensenii* bacteria were grown in 200 ml of MRS medium at 37° C. and 5% CO2 to an optical density at 600 nm of 1.0 ($OD_{600}=1.0$). The cells were harvested by centrifugation at 6,600×g for 10 min, and washed once in 25 mM Tris-HCl, pH 8.0, 10 mM EDTA, 50 mM glucose, and suspended after additions of 2.5 ml of 20 mM Tris, pH 8.0, 5 ml of 24% polyethylene glycol 8000, and 2.5 ml of lysozyme (4 mg/ml, Sigma Chemical Co., St. Louis, Mo.) per 100 ml of bacterial culture. The resulting cell suspensions were incubated at 37° C. for 1 hr. Upon addition of 5 ml of 0.2 M EDTA, the cells were centrifuged at 1,000×g for 10 min at 4° C. and resuspended in 10 ml of 20 mM Tris, pH 8.0 containing 50 µl of mutanolysin (15,000 U/ml; Sigma Chemical Co.). After incubation at 37° C. for 1 hr, the cells were lysed by addition of 1.5 ml of 9% Sarkosyl (Sigma Chemical Co.) and 3 ml of 5 M NaCl. The cell lysate was then mixed with 2.9 ml of 5 M sodium perchlorate. Chromosomal DNA was extracted with 17.5 ml chloroform-isoamyl alcohol (24:1 v/v) and precipitated by ethanol, air dried, and resuspended in 100 mM Tris-HCl, pH 8.0, 1 mM EDTA at a concentration of 1.5 mg/ml. Finally, the genomic DNA preparations were treated with DNase-free RNase.

Construction of L. jensenii Genomic Libraries

Genomic DNA of L. jensenii 1153 was mechanically sheared to the desirable size range using HydroShear (GeneMachines, San Carlos, Cailf.). Sheared DNA fragments were blunt ended by T4 DNA polymerase and Klenow enzyme, and the DNA fragments at 3 and 8 Kb were then isolated after agarose gel electrophoresis and purified using a QIAquick Gel Extraction Kit (Qiagen, Valencia, Calif.). The resulting DNA fragments were ligated into pUC18 vector and transformed into E. coli DH10B cell (Invitrogen, Carlsbad, Calif.) to make 3- and 8-Kb genomic libraries. The bacterial transformants were selected on LB plates in the presence of X-gal and resulting colonies were arrayed into 96-well plates using a Q-pix robot (Genetix Ltd., UK). The quality of the libraries was determined by testing a plate consisting of 96 clones for uniformity of insert size and percentage of non-recombinants. Both libraries contained less than 5% of non-recombinants and over 90% of the insert were within 20% of the expected size.

L. jensenii Genome Sequencing and Assembly

The L. jensenii genome sequence was determined by using the whole-genome shotgun approach. Plasmid DNA of selected clones from genomic libraries was purified by either magnetic beads or the rolling circle method and sequenced from both ends using ABI BigDye terminator kits (Applied Biosystems, Foster City, Calif.). All sequencing reactions were run on an ABI PRISM 3700 automated DNA sequencer (Applied Biosystems). A total 15,360 sequence reads, or 160 sequence plates, were run to provide 3-fold coverage of the L. jensenii 153 genome. A sequencing read is only considered successful when it generates over 50 bases of Q20 (1 possible error in 100 bases) or meets higher accuracy. The sequence chromatographs were automatically transferred to a UNIX system for base calling and quality assessment using Phred (Ewing et al., *Genome Research* 8:175-185 (1998)). The pass rate is more than 80% and the average read length is in the range of 400-500 bases. The sequence assembly was performed using the Paracel GenomeAssembler or CAP4 (Paracel, Inc., Pasadena, Cailf.). A total 484 contigs were assembled.

Identification of Protein Sequences with Cell Wall Anchor Motif in L. jensenii 1153 Genome Cell wall anchored proteins of Gram-positive bacteria have a conserved C-terminal LPXTGX (SEQ ID NO:31) motif (Fischetti et al., *Mol. Microbiol.* 4:1603-1605 (1990)). This hexapeptide is followed by a hydrophobic stretch of amino acids and a short charged tail, also known as a stop transfer sequence. (Schneewind et al., *Cell* 70:267-281 (1992). In addition, another unique LPXTA (SEQ ID NO:30) sorting motif was identified in Lactobacillus paracasei (Holck and Naes., *J. Gen. Microbial.* 138:1353-1364 (1992)). To identify native cell wall anchor sequences, a computer script was written to identify motifs similar to LPXTG (SEQ ID NO:9) and LPXTA (SEQ ID NO:30) in all reading frames of the assembled contigs (resulting from estimated 75% complete genome sequence of L. jensenii 1153). The resulting contigs with putative cell wall anchor motifs were further verified by BLAST search for sequence homology to cell wall-anchored proteins in Gram-positive bacteria.

Construction of Shuttle Vector

The primary shuttle vector used in these studies was pOSEL175, a modified version of pLEM7 (Fons et al., *Plasmid* 37:199-203 (1997). The partial IS element was deleted by first cutting with Sma I, partially digesting with Nde I, blunting with Klenow fragment and then religating. Finally, the plasmid was subjected to site-directed mutagenesis to remove two Mfe I sites within the erm gene of pOSEL144 (Chang et al., *Proc. Natl. Acad. Sci. USA.* 100: 11672-11677 (2003)). The resulting pOSEL175 plasmid has both replication origins in E. coli (ColE1) and Lactobacillus (repA), and thus contains the backbone of shuttle vectors used for the expression of heterologous proteins in a variety of Lactobacillus species.

Construction of Expression Cassettes in L. jensenii

To conveniently surface anchor proteins in L. jensenii, an expression cassette was constructed and sub-cloned into the SacI and XbaI sites of pOSEL175. The cassette contains four components, including a lactobacillus-compatible $P_{23}$ promoter, CbsA signal sequence of L. crispatus, DNA encoding a heterologous protein, and covalent cell wall anchoring domains from known or putative cell surface proteins in Gram-positive bacteria. Our detailed analyses of constructs harboring a series of promoters and signal sequences indicated that a combination of the $P_{23}$ promoter from Lactococcus lactis (van der Vossenet et al., *Appl. Environ. Microbiol.* 53:2452-2457 (1987)) and the signal sequence from the CbsA of L. crispatus (CbsAss) drives the highest levels of protein expression of 2D CD4 in the construct designated as pOSEL651 (Chang et al., *Proc. Natl. Acad. Sci. USA.* 100: 11672-11677 (2003)). Unique restriction sites, including SacI, EcoRI, NheI, MfeI, and XbaI were placed between each component from 5' to 3' ends, respectively. Amplification of each component by PCR was performed using Pfu DNA polymerase. Oligonucleotide primers for PCR amplification of various portions of the fusion constructs detailed in this study include the following:

```
                                         (SEQ ID NO: 32)
P23.f    5'-GTGGAGCTCCCCGAAAAGCCCTGACAACCC-3'

(SEQ ID NO: 33)
P23.r    5'-GGAAACACGCTAGCACTAACTTCATT-3'

(SEQ ID NO: 34)
2DCD4.f  5'-GCGGCTAGCAAGAAAGTTGTTTTAGGTAAA-3'

(SEQ ID NO: 35)
2DCD4.r  5'-GCACAATTGTGATGCCTTTTGAAAAGCTAA-3'

(SEQ ID NO: 36)
CbsAss.f 5'-GCGAATTCAAGGAGGAAAAGACCACAT-3'

(SEQ ID NO: 37)
CbsAss.r 5'-CCAGCTAGCTGAAACAGTAGAAACGGC-3'
```

Proteins designed for surface expression include a 10-amino acid c-Myc peptide (EQKLISEEDL; SEQ ID NO:15) and the first 183 residues comprising the N-terminal two extracellular domains of human CD4 (2D CD4). The 2D CD4 protein was recoded to conform to a preferred lactobacillus codon usage. All expression constructs were confirmed by DNA sequence analysis prior to transformation into L. jensenii.

Construction of c-Myc Fusion to Putative Cell Wall Anchor Sequences of L. jensenii We chose initially epitope tagging to determine the level of protein expression and whether it is feasible to use a defined length of putative cell wall anchor sequence for surface display of biologically active proteins. In order to not disrupt functioning of C-terminal sorting motif, oligonucleotide primers containing the 10 amino acid c-Myc epitope (EQKLISEEDL; SEQ ID NO:15) in the 5' end were designed, allowing fusion of c-Myc epitope to the N-terminus of the putative cell wall anchor sequences, including C14, C191, and C370 from the genome of L. jensenii 1153. The c-Myc sequences were either fused directly to the cell wall anchor motif of these proteins (the C-terminal 30 amino acids of C14, C191, and C370) or to sequences containing the C-terminal cell wall anchor domain and various lengths of contiguous upstream amino acids. Most notably, c-Myc was fused to a 200 amino acid sequence containing the cell wall anchor domain and upstream amino acids (designated CWA 200).

Myc14nhe (5' primer) (SEQ ID NO: 38)
(GCGCTAGCGAACAGAAACTGATCTCCGAAGAGGACCTGGTAACTC

GTACTATCAATGTA)

Myc14mfe (3' primer) (SEQ ID NO: 39)
(CGCCAATTGCTACTTTTGACGTTTCTTTCT)

Myc191nhe (5' primer) (SEQ ID NO: 40)
(GCGCTAGCGAACAGAAACTGATCTCCGAAGAGGACCTGGACGTAG

TAATTCCAGGAA)

Myc191mfe (3' primer) (SEQ ID NO: 41)
(GCGCAATTGTTAATCTTCTTTTCTCTTCTT)

Myc370nhe (5' primer) (SEQ ID NO: 42)

(GCGCTAGCGAACAGAAA

CTGATCTCCGAAGAGGACCTGTTGAAGAAGGCAGAAGAAGT)

Myc370mfe (3' primer) (SEQ ID NO: 43)
(CCGCAATTGTTATGCTTCATCATCTTTTCT)

All of the PCR products with expected size were gel-purified and digested with both MfeI and NheI. The resulting fragments were ligated with MfeI/NheI double digested pOSEL651 to make c-Myc fusion in pOSEL239 (via CWA200 of C14 sequence), pOSEL240 (via CWA200 of C191 sequence), and pOSEL241 (via C370 sequence), respectively. The resulting plasmids were electroporated into L. jensenii 1153.

Subcloning of Cell Wall-Anchoring Sequences into Shuttle Vector

Three putative surface proteins containing C-terminal LPQTG (SEQ ID NO:13) anchoring motif were chosen to determine their ability to express foreign proteins on the cell wall of L. jensenii 1153. The DNA regions containing the C-terminal LPQTG (SEQ ID NO:13) domain and their upstream 200 amino acids of these surface proteins (tentatively designated as CWA200 region) were amplified by three sets of primers, as described below, (SEQ ID NO: 44)
C14:   5' primer (GCGCAATTGGTAACTCGTACTATCAATGTA;

(SEQ ID NO: 45)
3' primer (CGCTCTAGATACACAAACTATTTTACGGTC;

(SEQ ID NO: 46)
C191:  5' primer (GCGCAATTGGACGTAGTAATTCCAGGAACA;

(SEQ ID NO: 47)
3' primer (CGGTCTAGACCAAGCAATTTATATATTGCT;

(SEQ ID NO: 48)
C370:  5' primer (GCGCAATTGAAGAAGGCAGAAGAAGT;

(SEQ ID NO: 49)
3' primer (CCGTCTAGATTATGCTTCATCATCTTTTCT;

The internal MfeI site of C14 anchor domain and the internal XbaI site of the C370 domain were mutated by site-directed mutagenesis before enzymatic restriction. All the PCR products of predicted size were gel-purified and digested with both MfeI and XbaI. The resulting fragments were ligated with MfeI/XbaI double digested pOSEL651, which contains P23-regulated secreted 2D CD4, to make plasmid pOSEL237 (via CWA200 of C14 sequence), pOSEL242 (via CWA200 of C191 sequence) and pOSEL249 (via CWA300 of C370 sequence), respectively. Alternatively, the C-terminal 36-amino acid anchor motif of C14 sequence was similarly cloned into shuttle vector by using following two primers.

Mfec14up: (SEQ ID NO: 50)
5' GCGCAATTGCCACAAACTGGTTCTAAGACT

Xnac14lo: (SEQ ID NO: 51)
3' primer (CGCTCTAGATACACAAACTATTTTACGGTC;

All of the resulting plasmids after verification of DNA sequences were electroporated into L. jensenii, L. gasseri, and L. casei.

Subcloning of the Repetitive Cell Wall Spanning Regions of C370 Sequence

Different repetitive cell wall spanning regions upstream the C370 LPQTG (SEQ ID NO:13) motif were amplified from the genomic DNA of L. jensenii 1153. The same 3' primer (5'-CCG TCTAGATTATGCTTCATCATCTTTTCT-3'; SEQ ID NO:49) was used, in pair with the following 5' primers for each PCR reaction.

(SEQ ID NO: 52)
Zero repeat:  5'-CGGCAATTGCCTCAAACTGGTACTGA-3'

(SEQ ID NO: 53)
One repeat:   5'-CGGCAATTGGGTCAAACTACAAATAAAGAT-3'

(SEQ ID NO: 54)
Two repeats:  5'-CGCCAATTGGGTCAAACTACTGATAAGAGT-3'

(SEQ ID NO: 55)
Three repeats: 5'-GCGCAATTGGGTCAAACTACAAATAAAGAT-3'

(SEQ ID NO: 52)
Four-eight    5'-CGGCAATTGGGTCAAACTACTGACAAGAGC-3'
repeats:

Both MfeI and XbaI sites in these primers are underlined.

All the PCR products of predicted size were gel-purified and digested with both MfeI and XbaI. The resulting fragments were ligated with MfeI/XbaI double digested pOSEL237, which contains P23-regulated secreted 2D CD4, to make plasmid pOSEL262 (with no repeat), pOSEL268 (with one repeat), pOSEL278 (with two repeats), pOSEL284 (with three repeats) pOSEL280 (with four repeats), pOSEL275 (with six repeats), pOSEL281 (with seven repeats) and pOSEL276 (with eight repeats), respectively.

Bacterial Transformation

Plasmids were introduced by electroporation into *E. coli* DH12S (Invitrogen). For shuttle plasmid construction and maintenance, the transformed *E. coli* DH12S cells were grown in LB broth (Difco) at 37° C., supplemented with 100 μg/ml ampicillin or 300 μg/ml erythromycin. After DNA sequence verification, *E. coli*-derived plasmids were transformation into *L. jensenii*, *L. gasseri*, and *L. casei* according to Luchansky et al (*J. Dairy Sci.* 74, 3293-3302 (1991)) with modifications Briefly, freshly inoculated *L. jensenii* were cultured in MRS broth to 0.6-0.7 at $OD_{600}$ at 37° C. and 5% $CO_2$. The bacterial cells were harvested, washed and re-suspended in 952 mM sucrose and 3.5 mM $MgCl_2$ at 4° C. Using a pre-chilled 0.2 cm gap cuvette, competent cells were added with 1~2 μg of DNA and electroporated immediately at 2.5 kV/cm and 200 ohms using Gene Pulser II (Bio-Rad, Hercules, Calif.). Afterward, cells were allowed to recover in pre-warmed MRS broth for two hours at 37° C., prior to being plated on selective MRS agar plates containing 20 μg/ml erythromycin, a concentration also used for routine propagation of transformed *L. jensenii* in liquid media.

Site-Directed Mutagenesis of LPXTG Motif of Putative Cell Wall Anchor Sequences

Point mutations were generated using QuickChange® XL Site-Directed Mutagenesis Kit from Stratagene (La Jolla, Calif.). Plasmid pOSEL237 (expressing 2D CD4 anchored via CWA200 of C14 sequence) and plasmid pOSEL249 (expressing 2D CD4 anchored via CWA200 of C370 sequence) were used as templates. The mutagenic primers were designed based on the nucleotide sequences corresponding to LPQTG (SEQ ID NO:13) and its flanking sequences on C14 and C370:

(SEQ ID NO: 57)
C14-
GAAAGTAAGAAGACTTTACCACAAACTGGTTCTAAGACTGAA (SEQ ID NO: 58)
C370-
CATAAGCAAACTCTATTGCCTCAAACTGGTACTGAAACTAACCCAC

The replacement nucleotides were selected using *L. jensenii* 1153 preferred codons:

237P(A): Proline on LPQTG (SEQ ID NO:13) of C14 was replaced with Alanine (SEQ ID NO: 59)
5'-GAAAGTAAGAAGACTTTAGCACAAACTGGTTCTAAGA-3'

(SEQ ID NO: 60)
5'-GTCTTAGAaccAGTTTGTGCTAAAGTCTTCTTACTTTC-3'

237P(N): Proline on LPQTG (SEQ ID NO:13) of C14 was replaced with Asparagine (SEQ ID NO: 61)
5'-GAAAGTAAGAAGACTTTAAATCAAACTGGTTCTAAGAC-3'

(SEQ ID NO: 62)
5'-GTCTTAGAACCAGTTTGATTTAAAGTCTTCTTACTTTC-3'

237T(A): Threonine on LPQTG (SEQ ID NO: 13) of C14 was replaced with Alanine (SEQ ID NO: 63)
5'-AGAAGACTTTACCACAAGCTGGTTCTAAGACTGAAC-3'

(SEQ ID NO: 64)
5'-GTTCAGTCTTAGAACCAGCTTGTGGTAAAGTCTTCT-3'

237T(G): Threonine on LPQTG (SEQ ID NO: 13) of C14 was replaced with Glycine (SEQ ID NO: 65)
5'-AGAAGACTTTACCACAAGGTGGTTCTAAGACTGAAC-3'

(SEQ ID NO: 66)
5'-GTTCAGTCTTAGAACCACCTTGTGGTAAAGTCTTCT-3'

237T(S): Threonine on LPQTG (SEQ ID NO: 13) of C14 was replaced with Serine (SEQ ID NO: 67)
5'-AGAAGACTTTACCACAAAGTGGTTCTAAGACTGAAC-3'

(SEQ ID NO: 68)
5'-GTTAGTTTCAGTACCACTTTGAGGCAATAGAGTTTG-3'

237G(A): Glycine on LPQTG (SEQ ID NO: 13) of C14 was replaced with Alanine (SEQ ID NO: 69)
5'-GACTTTACCACAAACTGCTTCTAAGACTGAACAAG-3'

(SEQ ID NO: 70)
5'-CTTGTTCAGTCTTAGAAGCAGTTTGTGGTAAAGTC-3'

249P(A): Proline on LPQTG (SEQ ID NO: 13) of C370 was replaced with Alanine (SEQ ID NO: 71)
5'-CATAAGCAAACTCTATTGGCTCAAACTGGTACTGAAAC-3'

(SEQ ID NO: 72)
5'-GTTTCAGTACCAGTTTGAGCCAATAGAGTTTGCTTATG-3'

249P(N) Proline on LPQTG (SEQ ID NO: 13) of C370 was replaced with Asparagine (SEQ ID NO: 73)
5'-CATAAGCAAACTCTATTGAATCAAACTGGTACTGAAAC-3'

(SEQ ID NO: 74)
5'-GTTTCAGTACCAGTTTGATTCAATAGAGTTTGCTTATG-3'

249T(A) Threonine on LPQTG (SEQ ID NO: 13) of C370 was replaced with Alanine (SEQ ID NO: 75)
5'-CAAACTCTATTGCCTCAAAGTGGTACTGAAACTAA-3'

(SEQ ID NO: 76)
5'-GTTAGTTTCAGTACCAGTTTGAGGCAATAGAGTTTG-3'

249T(G) Threonine on LPQTG (SEQ ID NO: 13) of C370 was replaced with Glycine (SEQ ID NO: 77)
5'-CAAACTCTATTGCCTCAAGGTGGTACTGAAACTAAC-3'

(SEQ ID NO: 78)
5'-GTTAGTTTCAGTACCACCTTGAGGCAATAGAGTTTG-3'

249T(S) Threonine on LPQTG (SEQ ID NO: 13) of C370 was replaced with Serine (SEQ ID NO: 79)
5'-CAAACTCTATTGCCTCAAAGTGGTACTGAAACT-3'

(SEQ ID NO: 80)
5'-GTTAGTTTCAGTACCACTTTGAGGCAATAGAGTTTG-3'

249G(A) Glycine on LPQTG (SEQ ID NO: 13) of C370 was replaced with Alanine (SEQ ID NO: 81)
5'-CTCTATTGCCTCAAACTGCTACTGAAACTAACCCAC-3'

(SEQ ID NO: 82)
5'-GTGGGTTAGTTTCAGTAGCAGTTTGAGGCAATAGAG-3'

Polymerase chain reaction (PCR) cycling conditions were 95° C. for 50 sec, 60° C. for 50 sec, and 68° C. for 12 min for a total of 16 cycles.

Dpn I enzyme were added to the amplification mixture after the PCR reaction to degrade the parental plasmids. Newly synthesized plasmids were introduced into chemically competent *E. coli* Top10 cells (Invitrogen) following the manufacturer's recommendations. Plasmids were maintained and amplified in LB broth (Difco) supplemented with 200 µg/ml erythromycin. After DNA sequence verification, *E. coli*-derived plasmids were transformation into *L. jensenii* according to Luchansky et al (*J. Dairy Sci.* 74, 3293-3302 (1991)) with modifications. MRS containing 20 µg/ml erythromycin was used for selection and propagation of transformed *L. jensenii* containing the mutagenic plasmids.

Deletion Analysis of Positive Charged C-terminal Sequences of Putative Cell Wall Anchor Proteins A series of deletion mutants, in which positively charged amino acid located at the C-terminus of C14 and C370 were generated by PCR amplification. Plasmids pOSEL237 and pOSEL249 were used as template. An oligonucleotide complementary to 2D CD4 sequence on pOSEL237 and pOSEL249 (CD4F 5'-GATCGTGCTGATTCACGTCGT-3'; SEQ ID NO:83) was used as forward primer. The following oligonucleotides (with restriction sites underlined) were used as reverse primers for amplifying the C-terminal of 2D CD4 cDNA and complete C14 and C370 CWA200 sequences:

```
                                           (SEQ ID NO: 84)
C14-7    5'-GCGCTCTAGACTAAACACCTAAGCCTAATAAGC-3'

(SEQ ID NO: 85)
C14-6    5'-GCGCTCTAGACTAGTTAACACCTAAGCCTAATAAG-3'

(SEQ ID NO: 86)
C14-5    5'-GCGCTCTAGACTATCTGTTAACACCTAAGCC-3'

(SEQ ID NO: 87)
370-10   5'-GCGCTCTAGATTAAAAAATTCCTGCGCCTAATG-3'

(SEQ ID NO: 88)
370-9    5'-GCGCTCTAGATTATGCAAAAATTCCTGCGCCTAATG-3'

(SEQ ID NO: 89)
370-8    5'-GCGCTCTAGATTACTTTGCAAAAATTCCTGCGCC-3'
```

All reverse primers contained a XbaI restriction site. The cycling conditions were 94° C. for 45 sec, 60° C. for 45 sec, and 72° C. for 90 sec for a total of 18 cycles. The PCR products were gel-purified and digested with both MfeI and XbaI, and then sub-cloned into MfeI/XbaI double digested pOSEL237 and pOSEL249, respectively. The sequences were verified by nucleotide sequencing, and the constructs were electroporated into *L. jensenii* for protein analysis.

Western Analysis of Heterologous Protein Expression in *L. jensenii*

Genetically modified *L. jensenii* cells were grown in Rogosa SL broth buffered with 100 mM HEPES, pH 7.1 at 37° C. and 5% CO2. To determine level of soluble proteins, conditioned media were collected after centrifugation at 12,000×g and proteins were then precipitated with TCA at a final concentration of 20%. TCA precipitates were washed with ethanol, air dried and heat denatured in 50 mM Tris-HCl, pH 6.8, 0.4% SDS, 6% sucrose, 10 mM dithiothreitol, and 0.01% bromphenol blue (1× reducing SDS-PAGE buffer). To determine relative amounts of cell-associated proteins in *L. jensenii*, bacterial cells were extracted without inducing cell lysis in 100 µL per OD600 unit of 1× SDS-PAGE buffer at 37° C. for 30 min. Extracted proteins were harvested following centrifugation at 12,000×g for 5 min and subsequently heat denatured. Soluble proteins were separated from bacterial cells by centrifugation at 14,000×g and resolved by SDS-PAGE in a 4-12% NuPAGE system (Invitrogen) in the presence of antioxidant according to manufacture's recommendation. After electrophoretic separation, proteins were electroblotted on to polyvinylidine difluoride membranes (Millipore) in 20% methanol, 20 mM Tris, and 50 mM glycine. The blot was then probed with polyclonal rabbit anti-CD4 antibodies, T4-4 (the NIH AIDS Research and Reference Reagent Program) or rabbit anti-CV-N pAb, and monoclonal antibody against c-Myc (Invitrogen). The antigen-antibody reaction was visualized by using chromogenic detection reagents (Promega, Madison, Wis.) for alkaline phosphase conjugated anti-rabbit IgG (for CD4 detection) or enhanced chemilluminescent reagents (Amercham Biosciences, Piscataway, N.J.) for horseradish peroxidase (HRP) conjugated anti-mouse IgG (for c-Myc detection). Similarly, level of c-Myc tagged proteins were probed with mAb against c-Myc (Invitrogen) and bound antibodies were detected with HRP-conjugated anti-mouse secondary antibodies (Amersham Biosciences).

Enzymatic Digestion of *L. jensenii* Cell Wall by Muramidase

Bacterial cultures containing $10^9$ bacteria were centrifuged at 12,000×g for 5 min. The resulting cell pellets were washed once in 20 mM HEPES, pH 7.2 and suspended in 100 µL of 10 mM Tris-HCl, pH 8.0, 1 mM EDTA, 25% sucrose (Piard et al., *J. Bacteriol.* 179:3068-3072 (1997)). The bacterial cell walls were digested in the presence of muramidase, mutanolysin (Sigma Chemical Co.) at a final concentration of 15 units/ml for 1 hr at 37° C. Afterward, the cells were centrifuged at 2,500×g for 10 min to isolate cell wall enriched fraction from protoplast-enriched one. The resulting samples were heat denatured after addition of 25 µl of 4× or 125 µl of 1× reducing SDS-PAGE buffer to cell wall or protoplast enriched fractions, respectively. Alternatively, CD4 ELISA was used to analyze proteins in the cell wall enriched fractions without additional sample treatment.

Labeling of Surface Exposed Proteins in *L. jensenii* with Sulfo-NHS-biotin

Surface exposed lysyl residues of surface proteins in *L. jensenii* were probed by use of membrane impermeable sulfo-N-hydroxysuccinimido (NHS)-biotin. Surface labeling of Gram-negative bacteria *Helicobacter pylori* by NHS-biotin allows identification of genuine cell surface proteins (Sabarth et al., *J. Biol. Chem.* 70:27896-27902 (2002)). Approximately $10^9$ of *L. jensenii* bacteria at log phase were washed once and suspended in PBS. Sulfo-NHS-biotin was added to 1 ml of cell suspension at a final concentration of 1 mM and allowed to incubate for 30 min at room temperature, with a continuous rotation. Afterward, the biotinylation reaction was quenched with addition of 50 mM Tris, pH 8.0, and the cells were washed once with 20 mM HEPES, pH 7.2. The cell-associated proteins were extracted without inducing cell lysis in 125 µl of 0.4% SDS, 6% sucrose, 10 mM DTT, 50 mM Tris-HCl, pH 6.8 at 37° C. for 30 min. The extracted proteins were separated from bacterial cells by centrifugation at 14,000×g for 5 min. After heat denaturation, proteins were resolved in a 4-12% NuPAGE (Invitrogen). Biotinylated proteins and their mobility shift were determined, following probing with alkaline phosphatase conjugated strepavidin or other immunological probes.

Analysis of Surface Expression of 2D CD4 by Flow Cytometry

Transformed *L. jensenii* harboring plasmids for surface protein expression or protein secretion in pOSEL651 were in grown in MRS broth in the presence of 20 μg/ml erythromycin at 37° C. and 5% CO2 for overnight (with OD600>3). The overnight cultures were then sub-cultured at 1:50~100 dilutions in erythromycin-containing MRS or Rogosa SL Broth that is buffered with 100 mM HEPES, pH 7.1 except otherwise indicated. One ml of cell cultures at $OD_{600}$~=0.4 was centrifuged at 12,000×g for 5 min. The resulting cell pellets were washed twice and suspended in 1×PBS containing 2% FBS. Afterward, cells were surface-stained in 2% FBS in 1×PBS for 30 min by using specific antibodies (1:1000 dilution for rabbit polyclonal T4.4 or 50 μg/ml for monoclonal Sim.4 per $2×10^8$ cells), followed by FITC or phycoerythrin-conjugated anti-rabbit or mouse antibodies (Becton-Dickinson, Mountain View, Calif.). A similar protocol was developed for the detection of surface expressed CV-N. Controls consisted of isotype-matched monoclonal antibodies (Becton Dickinson). Labeled cells were fixed with 1% (v/v) paraformaldehyde and analyzed in a FACScalibur system (Becton-Dickinson) running with the CellQuest software. Density plot output (Side scatter or forward scatter vs fluorescence) in background control was obtained from *L. jensenii* harboring pOSEL175. The shift in mean fluorescence intensity between the plots was taken as a measure of antibody binding to bacterial surface and calculated using FLOWJO software.

Enzyme-Linked Immunosorbent Assay

The concentration of correctly folded 2D CD4 proteins was determined by CD4 capture enzyme-linked immunosorbent assay (ELISA) that was modified according to McCallus et al. (*Viral Immunol.* 5:209-219 (1992)). 2D CD4 proteins with correct conformation in bacteria-free conditioned media were captured on a MaxiSorp 96-well plate (Nalge Nunc International, Denmark) by monoclonal antibody Sim.4 at 2.5 μg/ml. After washes in 1× Tris-buffered saline containing 0.05% Tween 20, the bound CD4 molecules, in reference to *E. coli* derived and refolded 2D CD4 standards, were probed with rabbit polyclonal antibodies, T4-4, then detected by horseradish peroxidase-conjugated anti-rabbit IgG (Amersham Biosciences) in the presence of 3,3',5,5' tetramethylbenzidine (Neogen Corp., Lexington, Ky.) at room temperature and in the dark for 30 minutes. The reaction was stopped after addition of 100 μl of 0.5 M $H_2SO_4$ and absorbance at 450 nm was read using microplate reader (Molecular Devices, Sunnyvale, Calif.).

The above example is provided to illustrate the invention but not to limit its scope. Other variants of the invention will be readily apparent to one of ordinary skill in the art and are encompassed by the appended claims. All publications, databases, Genbank sequences, patents, and patent applications cited herein are hereby incorporated by reference.

What is claimed is:

1. An isolated *Lactobacillus jensenii* bacterium comprising an expression cassette, the expression cassette comprising a promoter operably linked to polynucleotide encoding a signal sequence and a biologically-active polypeptide, wherein the biologically active polypeptide is expressed, is anchored to the cell wall of the *Lactobaeillus* bacterium or is released from the *Lactobacillus* bacterium, and is linked to a heterologous carboxyl terminal cell wall targeting region and wherein the cell wall targeting region comprises sequence selected from group consisting of SEQ ID NO:7, SEQ ID NO:8, SEQ ID NO: 7 in which LPQTG (SEQ ID NO:13) is replaced with LPQSG, LPQAG or LPQTA (SEQ ID NO:11, 12, 14, respectively) and SEQ ID NO: 8 in which LPQTG (SEQ ID NO:13) is replaced with LPQSG, LPQAG, or LPQTA (SEQ ID NO:11, 12 or 14, respectively), and wherein the biologically active protein binds to a pathogen when the biologically active protein is contacted with the pathogen.

2. The *Lactobacillus jensenii* bacterium of claim 1, wherein the heterologous carboxyl terminal cell wall targeting region further comprises a charged sequence at the carboxyl terminus of the cell wall targeting region, wherein the charged sequence comprises a sequence selected from the group consisting of SEQ ID NO:22, SEQ ID NO:23, and SEQ ID NO:24.

3. The *Lactobacillus jensenii* bacterium of claim 1, wherein the *Lactobacillus jensenii* bacterium is a vagina-colonizing strain.

4. The *Lactobacillus* bacterium of claim 1, wherein the cell wall targeting region comprises the amino acid sequence LPQSG (SEQ ID NO:11).

5. The *Lactobacillus* bacterium of claim 1, wherein the cell wall targeting region comprises the amino acid sequence LPQAG (SEQ ID NO:12).

6. The *Lactobacillus* bacterium of claim 1, wherein the cell wall targeting region comprises the amino acid sequence LPQTG (SEQ ID NO:13).

7. The *Lactobacillus* bacterium of claim 1, wherein the cell wall targeting region comprises the amino acid sequence LPQTA (SEQ ID NO:14).

8. The *Lactobacillus jensenii* bacterium of claim 1, wherein the cell wall targeting region comprises SEQ ID NO:7.

9. The *Lactobacillus jensenii* bacterium of claim 1, wherein the cell wall targeting region comprises SEQ ID NO:8.

10. The *Lactobacillus jensenii* bacterium of claim 1, wherein the biologically active polypeptide is expressed in the cell wall of the bacterium.

11. The *Lactobacillus jensenii* bacterium of claim 1, wherein the pathogen is a bacterial pathogen.

12. The *Lactobacillus jensenii* bacterium of claim 1, wherein the pathogen is a fungal pathogen.

13. The *Lactobacillus jensenii* bacterium of claim 1, wherein the pathogen is a viral pathogen.

14. The *Lactobacillus jensenii* bacterium of claim 13, wherein the viral pathogen is HIV.

15. The *Lactobacillus jensenii* bacterium of claim 14, wherein the biologically active protein is CD4 or an HIV-binding fragment of CD4.

16. The *Lactobacillus jensenii* bacterium of claim 14, wherein the biologically active protein is 2D-CD4.

17. The *Lactobacillus jensenii* bacterium of claim 13, wherein the biologically active protein is cyanovirin-N or a virus-binding fragment of cyanovirin-N.

18. The *Lactobacillus jensenii* bacterium of claim 13, wherein the viral pathogen is herpes simplex virus.

19. The *Lactobacillus jensenii* bacterium of claim 13, wherein the biologically active protein is herpes simplex virus entry mediator C (HveC) or a virus-binding fragment of HveC.

20. The *Lactobacillus jensenii* bacterium of claim 1, wherein the biologically active polypeptide is released from the *Lactobacillus* bacterium.

21. The *Lactobacillus jensenii* bacterium of claim 2, wherein the biologically active polypeptide is anchored to the cell wall of the *Lactobacillus* bacterium.

* * * * *

```
                        SEQUENCE LISTING

<160> NUMBER OF SEQ ID NOS: 89

<210> SEQ ID NO 1
<211> LENGTH: 1765
<212> TYPE: PRT
<213> ORGANISM: Lactobacillus jensenii 1153
<220> FEATURE:
<223> OTHER INFORMATION: genomic C14 cell wall anchor sequence
<220> FEATURE:
<221> NAME/KEY: DOMAIN
<222> LOCATION: (1528)..(1765)
<223> OTHER INFORMATION: CWA200 cell wall associated region with anchor
      motif
<220> FEATURE:
<221> NAME/KEY: PEPTIDE
<222> LOCATION: (1730)..(1734)
<223> OTHER INFORMATION: anchor motif, sorting signal, cell wall
      targeting region

<400> SEQUENCE: 1

Met Asn Asp Ser Ser Ile Gly Thr Ile Asn Ile Thr Asn Asp Ile Thr
 1               5                  10                  15

Ile Thr Gly Lys Val Asn Gly Leu Thr Thr Ser Gly Ile Ser Asp Ile
             20                  25                  30

Asn Lys His Phe Leu Tyr Leu Gln Ser Glu Gly Ser Ala Arg Asp Leu
         35                  40                  45

Thr Ile Asn Gly Asn Gly His Arg Ile Asn Phe Ala Gly Tyr Ser Ile
     50                  55                  60

Ala Leu Gln Asn Lys Asn Tyr Thr Asn Ala Ala Asn Pro Trp Asn Ile
 65                  70                  75                  80

Thr Leu Lys Asp Met Thr Ile Glu Gly Ser Lys Tyr Asp Tyr Ser Pro
                 85                  90                  95

Ile Ser Phe Tyr Gly Arg Lys Ser Asn Thr Glu Asn Ser Lys Leu Thr
            100                 105                 110
```

```
Phe Asp Gly Val Thr Ala Asn Leu Asn Asp Arg Pro Leu Val Asp Lys
        115                 120                 125

Tyr Gly Glu Asn Leu Pro Val His Phe Ala Gly Glu Asn Asn Ile Thr
130                 135                 140

Leu Asn Asn Met Ser Ile Gly Tyr Asn Leu Val Thr Gly Lys Thr Val
145                 150                 155                 160

Lys Phe Asp Ser Gly Asn Thr Thr Phe Asn Val Asp Gly Lys Val Thr
                165                 170                 175

Gly Asn Ser Ile Asn Pro Asp Asn Trp Val Ile Arg Ser Thr Glu Asn
            180                 185                 190

Ala Ser Asn Ser Glu Asn Pro Ser Thr Leu Ile Asn Glu Gly Ala Thr
        195                 200                 205

Val Thr Ile Asn Ala Lys Ser Asp Asp Leu Arg Gly Ile Tyr Ala Gly
    210                 215                 220

Arg Gln Leu Thr Ala Gly Gln Pro Ile Tyr Gly Val Thr Val Ile Asn
225                 230                 235                 240

Gly Thr Leu Asn Ala Lys Met Ala Ala Gly His Ser Thr Ala Ile Trp
                245                 250                 255

Ser His Asp Leu Glu Ile Gly Lys Lys Gly Asn Val Thr Ile His Thr
            260                 265                 270

Lys Gln Thr Asn Gln Ala Asp Gly Val Glu Asn Gly Ser Asn Ser
        275                 280                 285

Val Thr Asn Tyr Asn Gly Thr His Tyr Ala Pro Ile Ser Leu Gly Val
    290                 295                 300

Gly Pro Ile Ser Ser Val Ala Ser Pro Leu Ser Lys Gln Thr Val Ser
305                 310                 315                 320

Leu Ile Asn Asn Gly Ser Leu Thr Ile Ile Arg Asp Thr Ala Lys Lys
                325                 330                 335

Thr Leu Val Pro Leu Ile Ser Met Gly Asp Gly Ser Leu Ser Ser Asn
            340                 345                 350

Thr Thr Leu Lys Phe Ser Val Gly Ala Gly Ala Thr Leu Asp Leu Gln
        355                 360                 365

Asp Lys Ala Gly Thr Phe Arg Tyr Gly Ile Glu Pro Ser Thr Pro Leu
    370                 375                 380

Asn Gly Leu Val Thr Leu Trp Gly Thr Ser Gly Thr Asp Leu Leu Glu
385                 390                 395                 400

Phe Leu Thr Pro Ala Tyr Val Asn Leu Gln Arg Thr Gly Asp Ile Arg
                405                 410                 415

Gly Thr Leu Ile Arg Met Glu Gly Val Tyr Asn Ser Thr Thr Val Asn
            420                 425                 430

Gly Pro Thr Pro Val Ala Gln Trp Asp Gln Gly Asn Lys Thr Thr Thr
        435                 440                 445

Pro Asn Asp Val Trp Tyr Val Arg Tyr Leu Ile Ser Ala Asn Gln Trp
    450                 455                 460

Gly Asn Asn Ser Gly Gln Phe Met Gly Lys Asp Gln His Pro Asn Thr
465                 470                 475                 480

Val Val Ala Lys Lys Gly Val Asp Thr Leu Tyr Asn Ser Asn Ala Thr
                485                 490                 495

Val Leu Met Ser Lys Asn Gln Gly Ala Asp Lys Tyr Glu Asn Gly Thr
            500                 505                 510

Met Pro Thr Glu Val Gln Gln Ala Leu His Leu Asn Ser Phe Leu Asn
        515                 520                 525
```

-continued

Asn Phe Asn Phe Trp Arg Pro Gln Arg Met Ala Met Gly Ser Lys Leu
530                 535                 540

Asn Asp Asn Pro Asp Val Lys Ile Asp Asp Phe Asp Lys Tyr His Ala
545                 550                 555                 560

Glu Ala Gln Thr Ile Asp Gly Thr Thr Arg Gln Thr Leu Ser Asp Leu
                565                 570                 575

Asp Ala Asn Lys Gly Leu Lys Asp Leu Ile Gly Pro Asp Glu Gln Pro
            580                 585                 590

Ile Thr Asp Phe Lys Asp Ile Val Lys His Val Thr Trp Tyr Asn Ser
        595                 600                 605

Ala Thr Asp Lys Asp Glu Trp Asn Lys Ile Met Ile Gln Pro Thr Asp
    610                 615                 620

Ser Lys Asp Pro Ser Ala Arg Val Pro Tyr Pro Glu Pro Gln Asn Pro
625                 630                 635                 640

Thr Gly Asn Leu Lys Thr Thr Asp Gly Phe Ala Trp Ala Lys Val Thr
                645                 650                 655

Tyr Ala Asp Gly Ser Val Asp Phe Val Lys Ile Pro Leu Lys Val Thr
            660                 665                 670

Glu Lys Lys Tyr Ser Glu Glu Leu Thr Pro Ser Tyr Pro Gly Val Ser
        675                 680                 685

Val Glu Gln Gly Lys Ser Asp Ser Val Asp Pro Ser Phe Lys Asp Glu
    690                 695                 700

Asn Asp Lys Ala Ala Asp Ala Pro Ala Gly Thr Lys Tyr Thr Ala Gly
705                 710                 715                 720

Glu Asn Thr Pro Asp Trp Ile Lys Val Asp Pro Asp Thr Gly Lys Val
                725                 730                 735

Thr Val Ser Pro Thr Asp Asp Thr Ser Val Gly Ser His Asp Ile Ser
            740                 745                 750

Val Thr Val Thr Tyr Pro Asp Ser Ser Thr Asp Gln Leu Thr Val Pro
        755                 760                 765

Val Thr Val Thr Glu Lys Ser Asn Leu Ala Glu Lys Tyr Pro Val Ser
    770                 775                 780

Tyr Asp Lys Leu Asn Val Glu Lys Pro Ser Gly Asp Thr Pro Ala Thr
785                 790                 795                 800

Gly Ala Val Asp Pro Lys Ala Ala Asp Met Pro Glu Gly Ala Ile
                805                 810                 815

Thr Gly Tyr Glu Lys Gly Asp Phe Asp Ala Pro Ala Gly Val Thr Ile
            820                 825                 830

Asp Val Asn His Asp Thr Gly Lys Val Thr Ala Ser Val Gly Lys Asn
        835                 840                 845

Ala Thr Leu Gly Ser Phe Glu Val Pro Val Lys Val Thr Tyr Ser Asp
    850                 855                 860

Gly Thr Tyr Ala Glu Val Lys Val Pro Val Ser Ile Thr Gly Asn Lys
865                 870                 875                 880

Val Asp Pro Gly Ser Gly Asp Val Val Tyr Tyr Gly Asp Gln Ser Met
                885                 890                 895

Val Val Phe Asn Gly Asn Leu Thr Thr Val His Lys Thr Thr Asp Ser
            900                 905                 910

His Glu Leu Ser Ala Lys Asp Ser Ala Phe Gln Thr Ile Thr Tyr Tyr
        915                 920                 925

Ser Asp Trp Asn Lys Lys Gly Asn Ile Val Ser Asp Tyr Asn Lys His
    930                 935                 940

Val Ile Tyr Lys Leu Ser Ala Asp Gly Thr Lys Tyr Val Asn Glu Ala

-continued

```
            945                 950                 955                 960

Asp Ala Thr Asp Ser Phe Asp Ala Ser Ala Ile Ser Phe Asn Trp Gln
                965                 970                 975

Lys Gly Tyr Glu Val Asn Thr Gly Val Asp Asn Phe Ser Asn Gly Ser
            980                 985                 990

Ala Asp Thr Leu Tyr Gln Leu Glu Lys Gly Ala Val Asn Ser Glu Glu
            995                 1000                1005

Gln Thr Asp Ala Asn Asp Pro Ser Gly Leu Ala Gly Asn Ser Lys Tyr
        1010                1015                1020

Arg Tyr Asp Phe Ser Ile Ser Asp Thr Asn Val Leu Gln Lys Leu Gly
1025                1030                1035                1040

Leu Ser Pro Ala Gly Tyr Asn Ala Trp Ala Asn Val Tyr Tyr Asn Phe
                1045                1050                1055

Leu Gly Ala Thr Gly Lys Ile Asn Ile Pro Val Asn Tyr Gly Ser Glu
            1060                1065                1070

Val Ser Thr Asp Glu Ala Gly Ile Lys Asn Tyr Leu Ala Thr Asn Ser
        1075                1080                1085

Ile Ser Gly Lys Thr Phe Val Asn Gly Asn Pro Thr Gly Ile Lys Trp
        1090                1095                1100

Ala Glu Asn Gly Met Pro Gly Lys Asp Gly Lys Phe Ala Ala Ser Asn
1105                1110                1115                1120

Met Thr Gly Ile Val Glu Phe Thr Phe Asp Asn Gly Thr Lys Leu Asn
                1125                1130                1135

Val Gln Val Thr Phe Lys Thr Gly Ser His Val Ser Thr Ser Gly Ser
            1140                1145                1150

Lys Val Asn Asp Asp Thr Asn Leu Tyr Val Glu Arg Thr Ile Glu Tyr
        1155                1160                1165

Asp Val Thr Gly Thr Gly His Ser Pro Ile Asn Ser Val Thr Gln Lys
        1170                1175                1180

Val His Tyr Val Arg Asp Gly Tyr His Lys Ile Asn Ala Asp Gly Thr
1185                1190                1195                1200

Asp Ala Gly Glu Ile Ile Trp Asn Glu Trp Lys Leu Ala Asp Gly Gln
                1205                1210                1215

Thr Ala Glu Phe Pro Glu Tyr Ser Val Asp Gln Ile Thr Gly Tyr Asp
            1220                1225                1230

Ala Tyr Ile Asn Gly Ala Lys Ala Thr Gln Val Asp Ala Ala Lys Val
        1235                1240                1245

Ala Glu Thr Asn Gly Thr Pro Gln Asn Gly Gln Asn Ile Thr Val Thr
        1250                1255                1260

Tyr Lys Lys Gln Asn Ser Thr Pro Val Pro Tyr Lys Pro Gly Lys Asp
1265                1270                1275                1280

Gly Val Asn Asp Ala Ile Asn Arg Tyr Val Thr Arg Thr Ile Ile Val
                1285                1290                1295

Lys Glu Pro Gly Lys Glu Pro Gln Thr Ile Thr Gln Thr Val His Phe
            1300                1305                1310

Thr Asn Glu Asp Lys Asp Gly Asn Ser Gly Tyr Lys Asp Pro Val Thr
        1315                1320                1325

Gly Glu Ile Lys Tyr Asn Thr Asp Trp His Val Ala Ser Asp Leu Asn
        1330                1335                1340

Ala Lys Thr Gly Ser Trp Glu Glu Tyr Thr Ala Pro Ser Val Thr Gly
1345                1350                1355                1360

Tyr Thr Pro Ser Gln Ala Lys Val Glu Ala Lys Thr Val Thr Ala Glu
            1365                1370                1375
```

```
Thr Glu Ala Ala Ser Val Thr Ile Ser Tyr Thr Lys Asn Ala Asp Ile
        1380                1385                1390

Pro Val Pro Tyr Lys Pro Gly Lys Asp Gly Val Asn Asp Ala Ile Asn
    1395                1400                1405

Arg Tyr Val Thr Arg Thr Ile Ile Val Lys Glu Pro Gly Lys Glu Pro
1410                1415                1420

Gln Thr Ile Thr Gln Thr Val His Phe Thr Asn Glu Asp Lys Asp Gly
1425                1430                1435                1440

Asn Ser Gly Tyr Lys Asp Pro Val Thr Gly Glu Ile Lys Tyr Asn Thr
            1445                1450                1455

Asp Trp His Val Ala Ser Asp Leu Asn Ala Lys Thr Gly Ser Trp Glu
        1460                1465                1470

Glu Tyr Thr Ala Pro Ser Val Thr Gly Tyr Thr Pro Ser Gln Ala Lys
    1475                1480                1485

Val Glu Ala Lys Thr Val Thr Ala Glu Thr Glu Ala Ala Ser Val Thr
1490                1495                1500

Ile Ser Tyr Thr Lys Asn Ala Asp Ile Pro Val Pro Phe Asp Pro Ser
1505                1510                1515                1520

Asn Lys Asp Met Tyr Arg Glu Val Thr Arg Thr Ile Asn Val Val Asp
            1525                1530                1535

Pro Ile Thr Gly Lys Ile Ser Thr Ser Val Gln Thr Ala Lys Phe Thr
        1540                1545                1550

Arg Glu Asp Lys Asn Ser Asn Ala Gly Tyr Thr Asp Pro Val Thr Gly
    1555                1560                1565

Lys Thr Thr Met Asn Pro Trp Thr Pro Ala Lys Gln Gly Leu Arg Ala
1570                1575                1580

Val Asn Val Glu Gln Ile Lys Gly Tyr Val Ala Lys Val Asp Gly Asn
1585                1590                1595                1600

Val Asp Ala Val Val Thr Pro Asp Ser Ala Asn Met Val Val Thr
            1605                1610                1615

Ile Thr Tyr Gln Ala Asn Lys Pro Glu Gly Gln Asn Ile Thr Val Lys
        1620                1625                1630

Lys Asp Thr Val Pro Asp Pro Ala Asp Gly Ile Lys Asn Lys Asp Asp
    1635                1640                1645

Leu Pro Asp Gly Thr Lys Tyr Thr Trp Lys Glu Val Pro Asp Val Asn
1650                1655                1660

Ser Val Gly Glu Lys Thr Gly Ile Val Thr Val Thr Phe Pro Asp Gly
1665                1670                1675                1680

Thr Ser Val Asp Val Lys Val Thr Val Tyr Val Asp Pro Val Val Glu
            1685                1690                1695

Ser Asn Arg Asp Thr Leu Ser Lys Glu Ala Asn Thr Gly Asn Thr Asn
        1700                1705                1710

Val Ala Lys Ala Ala Thr Val Thr Ser Ser Lys Val Glu Ser Lys Lys
    1715                1720                1725

Thr Leu Pro Gln Thr Gly Ser Lys Thr Glu Gln Val Gly Ile Leu Gly
1730                1735                1740

Leu Ala Ile Ala Thr Val Gly Ser Leu Leu Gly Leu Gly Val Asn Arg
1745                1750                1755                1760

Lys Lys Arg Gln Lys
            1765

<210> SEQ ID NO 2
<211> LENGTH: 974
```

```
<212> TYPE: PRT
<213> ORGANISM: Lactobacillus jensenii 1153
<220> FEATURE:
<223> OTHER INFORMATION: genomic C191 cell wall anchor sequence
<220> FEATURE:
<221> NAME/KEY: DOMAIN
<222> LOCATION: (740)..(974)
<223> OTHER INFORMATION: CWA200 cell wall associated region with anchor
      motif
<220> FEATURE:
<221> NAME/KEY: PEPTIDE
<222> LOCATION: (941)..(945)
<223> OTHER INFORMATION: anchor motif, sorting signal, cell wall
      targeting region

<400> SEQUENCE: 2

Met Pro Val Ala Asn Lys Pro Glu Gly Thr Val His Thr Thr Tyr Ser
 1               5                  10                  15

Trp Lys Asp Asn Ile Ile Pro Asp Thr Thr Lys Pro Gly Thr Lys Tyr
             20                  25                  30

Gly Ile Val Glu Val Asn Phe Pro Asp Gly Ser Thr Lys Asp Val Pro
         35                  40                  45

Val Glu Val Lys Val Thr Ser Leu Ala Ser Asp Tyr Gln Asn Lys Ile
     50                  55                  60

Asp Thr Lys Gln Ile Ile Ala Lys Tyr Lys Gly Asn Ile Pro Gln Ala
 65                  70                  75                  80

Ser Asp Gly Ile Ala Asn Lys Asp Gln Ala Thr Lys Glu Gly Asp Lys
                 85                  90                  95

Asp Phe Pro Ser Leu Ala Asp Val Leu Ala Pro Asn Gly Ile Gln Trp
            100                 105                 110

Lys Lys Asn Phe Glu Pro Asp Leu Ser Lys Pro Gly Leu Thr Ser Gly
        115                 120                 125

Glu Ala Ile Leu Thr Phe Lys Asp Gly Ser Thr Ala Glu Val Thr Ile
    130                 135                 140

Pro Val Leu Val Gln Thr Asp Ala Asp Arg Asn Thr Pro Glu Thr Gln
145                 150                 155                 160

Thr Ile Lys Thr Leu Pro Gly Gln Thr Val Asn Pro Glu Asp Gly Val
                165                 170                 175

Ile Asn Leu His Lys Pro Gly Glu Asn Asn Pro Gln Leu Pro Asp Gly
            180                 185                 190

Thr Lys Val Thr Phe Asp Asn Gln Ser Asp Val Asp Asp Phe Thr Lys
        195                 200                 205

His Gly Met Pro Gly Ser Asp Lys Ser Phe Asp Ala Thr Val Thr Tyr
    210                 215                 220

Pro Asp Gly Thr Thr Asp Lys Ile Lys Leu Pro Val His Ile Thr Ala
225                 230                 235                 240

Asp Asn Glu Val Asn Thr Pro Ile Thr Gln Gly Ile Ile Thr Pro Lys
                245                 250                 255

Asp Ser Val Pro Asp Ala Asn Lys Gly Ile Ala Asn Leu Lys Lys Ala
            260                 265                 270

Thr Thr Lys Glu Gly Lys Thr Tyr Pro Ala Leu Pro Glu Asn Thr Thr
        275                 280                 285

Val Glu Trp Val Asn Pro Gly Gln Met Lys Thr Glu Leu Glu Asn Ala
    290                 295                 300

Lys Gly Gly Thr Thr Lys Asn Tyr Asp Ala Val Val Ile Tyr Pro Asp
305                 310                 315                 320

Lys Ser Thr Glu Ile Val Ser Ile Pro Val Thr Val Ala Thr Asp Ala
                325                 330                 335
```

```
Asp Thr Tyr Lys Val Thr Gln Pro Ile Asp Leu Lys Asp Arg Asn
        340                 345                 350

Leu Pro Asp Asn Ala Asp Gly Ile Thr Asn Leu His Lys Pro Ala
            355                 360                 365

Asp Phe Lys Thr Pro Gln Leu Pro Asp Gly Thr His Ala Glu Trp Gln
        370                 375                 380

Asp Lys Asp Ala Ala Gln Glu Val Val Lys Asn Leu Lys Pro Gly Glu
385                 390                 395                 400

Thr Val Lys Leu Pro Ala Thr Val Phe Pro Asp Gly Ser Lys Lys
                405                 410                 415

Gly Glu Gly Ile Asp Val Ser Val His Leu His Gly Gln Ser Asp Asp
                420                 425                 430

Tyr Asn Ile Glu Thr Gln Pro Val Asn Thr Asp Lys Asp Gly Asn Leu
            435                 440                 445

Pro Glu Asn Ala Asp Ser Gly Ile Lys Asn Leu Gly Lys Leu Pro Glu
        450                 455                 460

Gly Thr His Ala Ser Trp Gly Asp Gly Ala Gln Asp Ile Ala Lys Asn
465                 470                 475                 480

Leu Lys Pro Gly Glu Thr Lys Asp Val Pro Ala Thr Val Phe Pro
                485                 490                 495

Asp Gly Ser Lys Lys Glu Ile Thr Ile Pro Val His Arg Glu Gly Gln
                500                 505                 510

Ser Asp Gly Tyr Asp Val Glu Pro Gln Leu Val Asn Thr Asp Lys Asn
            515                 520                 525

Gly Gln Leu Pro Asn Ala Lys Glu Gly Ile Lys Asn Leu Ala Asp Leu
        530                 535                 540

Pro Glu Gly Thr Asn Pro Thr Trp Ala Asp Arg Ala Gln Asp Lys Ile
545                 550                 555                 560

Asn Lys Thr Lys Pro Gly Thr Asp Thr Ala Gln Val Val Thr
                565                 570                 575

Phe Pro Asp Gly Ser Thr Lys Glu Val Thr Val Pro Val His Lys His
            580                 585                 590

Gly Gln Ser Asp Asp Tyr Gly Asp Lys Ile Val Thr Gln Arg Val Glu
        595                 600                 605

Thr Asp Ser His Gly Gln Leu Pro Glu Asn Ala Asp Ser Gly Ile Lys
        610                 615                 620

Asn Leu Gly Asp Leu Pro Glu Gly Thr His Ala Val Trp Gly Gln Gly
625                 630                 635                 640

Ala Gln Thr Ile Val Asp Gly Met Lys Pro Gly Glu Thr Lys Asp Val
                645                 650                 655

Pro Ala Thr Ile Glu Phe Pro Asp Gly Ser Thr Lys Asp Val Thr Ile
                660                 665                 670

Pro Val Tyr Lys Thr Ser Thr Arg Asp Gln Gly Thr Leu Asn Pro Pro
            675                 680                 685

Thr Asp Lys Val Ser Val Asp Asp Thr Lys His Ile Thr Asp Glu Asp
        690                 695                 700

Lys Gly Lys Val Ile Asp Asn Val Lys Lys Ser Asn Pro Lys Asp
705                 710                 715                 720

Ile Thr Asp Ala His Val Asp Asp Gly Thr Phe His Gly Lys Val
            725                 730                 735

Asp Gly Gln Asp Val Val Ile Pro Gly Thr Glu Thr Val Val Glu Lys
        740                 745                 750
```

-continued

```
Gln Lys Glu Ser Leu Asn Pro Pro Thr Asp Lys Val Pro Val Asp Asp
            755                 760                 765

Thr Lys His Ile Thr Asp Glu Asp Lys Gly Lys Val Ile Asp Asn Val
770                 775                 780

Lys Lys Ser Asn Pro Asp Lys Asp Ile Thr Asp Ala His Val Asp Asp
785                 790                 795                 800

Asp Gly Thr Phe His Gly Lys Val Asp Gly Gln Asp Val Val Ile Pro
                805                 810                 815

Gly Thr Glu Thr Val Val Glu Lys Gln Lys Glu Ser Leu Asn Pro Pro
            820                 825                 830

Thr Asp Lys Val Pro Val Asp Thr Lys His Ile Thr Asp Glu Asp
            835                 840                 845

Lys Gly Lys Val Ile Asp Asn Val Lys Lys Ser Asn Pro Asp Lys Asp
850                 855                 860

Ile Thr Asp Ala His Val Asp Asp Gly Thr Phe His Gly Lys Val
865                 870                 875                 880

Asp Gly Gln Asp Val Val Ile Pro Gly Ile Glu Thr Val Val Glu Lys
                885                 890                 895

Ser Thr Asn Asn Gln Lys Ser Asp Thr Asn Lys Gly Leu Ile Ser Asn
            900                 905                 910

Asp Asn Ser Glu Lys Asn Ser His Met Ile Asn Ala Asn Val Asn Thr
        915                 920                 925

Lys Ser Arg Asn Ser Leu Ser Ala Lys Gln Asn Arg Leu Pro Gln Thr
    930                 935                 940

Gly Ser Glu Thr Ser Gly Leu Ser Ala Leu Gly Leu Ala Met Leu Ser
945                 950                 955                 960

Leu Val Gly Leu Gly Phe Leu Ile Lys Lys Arg Lys Glu Asp
                965                 970

<210> SEQ ID NO 3
<211> LENGTH: 1903
<212> TYPE: PRT
<213> ORGANISM: Lactobacillus jensenii 1153
<220> FEATURE:
<223> OTHER INFORMATION: genomic C370 cell wall anchor sequence
<220> FEATURE:
<221> NAME/KEY: DOMAIN
<222> LOCATION: (1309)..(1903)
<223> OTHER INFORMATION: CWA200 cell wall associated region with anchor
      motif
<220> FEATURE:
<221> NAME/KEY: PEPTIDE
<222> LOCATION: (1868)..(1872)
<223> OTHER INFORMATION: anchor motif, sorting signal, cell wall
      targeting region

<400> SEQUENCE: 3

Met Phe Tyr Gln Ile Asp Pro Ala Leu Ala Pro Tyr Ile Asp Lys Ile
1               5                   10                  15

Val Phe Ser Arg Ala Leu Leu Ser Asp Gly Glu Ala Thr Lys Asp Thr
            20                  25                  30

Ser Asn Glu Val Pro Gly Ala Thr Asn Val Trp Thr Ser Gly Val Leu
        35                  40                  45

Thr Thr Gln Asn Gly Pro Ile Arg Ala Ala Leu Ala Gly Ser Thr Ser
    50                  55                  60

Ser Thr Tyr Lys Ile Tyr Leu Lys Ala Asp Thr Pro Asn Ser Ile Leu
65                  70                  75                  80

Ser Lys Pro Leu Ser Phe Thr Met Trp Ala Arg Tyr Ser Ser Gly His
                85                  90                  95
```

-continued

```
Asp Met Val Ser Asp Phe Ser Lys Asn Leu Ile Leu Asn Asp Asn Glu
            100                 105                 110

Thr Thr Thr Phe Ser Ser Asn Asn Phe Phe Lys Ser Leu Asp Ile Val
            115                 120                 125

Asn Asn Asp Gly Pro Ile Leu Asp Asn Met Ser Val Asp Tyr Ser Asn
130                 135                 140

Lys Thr Val Asn Thr Arg Tyr Arg Val Asn Gly Ser Leu Leu Gly Asp
145                 150                 155                 160

Lys Ser Asn Leu Thr Leu Arg Ile Arg Gly Asn Asp Asn Leu Leu Lys
                165                 170                 175

Leu Ile Asp Lys Val Lys Ile Ser Asn Lys Thr Tyr Thr Leu Ala Asn
            180                 185                 190

Asn Thr Leu Lys Tyr Arg Thr Gly Glu Leu Tyr Ile Asn Asp Ile Gly
            195                 200                 205

Gly Ser Leu Gly Phe Leu Ser Ser Leu Ser Asn Arg Gln Asp Phe Asn
210                 215                 220

Val Thr Phe Tyr Leu Lys Asn Gly Lys Ser Phe Ala Asp Ala Leu Thr
225                 230                 235                 240

Ser Glu Ser Gln Lys Phe Asp Phe Gln Phe Gly Ile Tyr Asp Thr Thr
                245                 250                 255

Asp Tyr Ala Thr Ala Phe His Ser Leu Asp Thr Val Thr Asn Ser Leu
            260                 265                 270

Ser Thr Lys Thr Tyr Thr Thr Gly Asp Lys Tyr Asn Asn Gln Thr Tyr
            275                 280                 285

Asp Leu Ser Thr Phe Lys Thr Ile Leu Asp Lys Leu Ile Lys Gln Lys
290                 295                 300

Gln Asp Asn Pro Thr Thr Tyr Leu Ser Phe Glu Asp Lys Lys Ile Ser
305                 310                 315                 320

Ala Thr Glu Asn Asn Pro Tyr Glu Ala Val Lys Leu Ala Leu Glu Ser
                325                 330                 335

Pro Thr Phe Thr Asn Ile Ser Ile Ala Lys Ser Leu Val Asn Ala Ala
            340                 345                 350

Asp Cys Lys Gln Leu Asp Asn Thr Ala Lys Trp Ala Trp Asp Asn Gly
            355                 360                 365

Ala Arg Asp Asp Leu Leu Lys Tyr Leu Asp Val Ala Thr Lys Val Ala
370                 375                 380

Ser Tyr Ile His Leu Glu Phe Pro Thr Lys Pro Thr Asp Phe Ser Gly
385                 390                 395                 400

Leu Leu Leu Arg Tyr Thr Arg Ala Gly Thr Phe Ile Ser Ala Val Asp
                405                 410                 415

Ser Asp Arg Asp Gly Val Leu Asp Ile Thr Glu Ile Asp Asn Ser Tyr
            420                 425                 430

Gly Met Asn Pro Ser Val Tyr Asp Thr Asp Gly Asp Gly Ile Ser Asp
            435                 440                 445

Gly Gln Glu Leu Arg Glu Gly Arg Asp Pro Gly Val Ala Pro Phe Asn
450                 455                 460

Trp Thr Asp Ala Asn Gly Asn Gln Leu Ser Ile Asp Val Asp Thr Thr
465                 470                 475                 480

Thr Ile Ser Gly Gln Leu Gly Asn His Asn Tyr His Asn Glu Val Met
                485                 490                 495

Gln Pro Arg Thr Val Asn Leu Tyr Lys Val Asp Asp Thr Gly Lys Lys
            500                 505                 510
```

```
Thr Leu Ile Ala Tyr Thr Thr Ser Ala Val Asp Gln Asn Gly Ser Phe
            515                 520                 525
Thr Leu Ser Lys Phe Thr Leu Asn Lys Gly Asp Lys Leu Val Ile Gly
        530                 535                 540
Tyr Val Thr Pro Arg Thr Asn Lys Ser Leu Thr Asp Lys Asp Thr Ile
545                 550                 555                 560
Leu Gln Gln Ala Phe Pro Thr Glu Gln Phe Ser Asn Glu Ile Ile Val
                565                 570                 575
Lys Gly Lys Gln Val Thr Val Thr Phe Asn Met Asn Gly Val Ser Asp
            580                 585                 590
Asp Glu Asn Gln Asp Ile Lys Val Glu Lys Asp Ser Ser Phe Asn Lys
        595                 600                 605
Asp Ser Leu Thr Leu Pro Thr Pro Thr Met Lys Thr Gly Tyr Ser Phe
    610                 615                 620
Lys Glu Trp Asn Thr Gln Ala Asp Gly Lys Gly Thr Val Val Thr Ala
625                 630                 635                 640
Asp Thr Ile Phe Asp Thr Asp Thr Thr Val Tyr Ala Ile Gly Glu Lys
                645                 650                 655
Ile Lys Leu Pro Asn Pro Thr Asn Ile Lys Ala Glu Thr Arg Thr Asp
            660                 665                 670
Asp Lys Thr Lys Ser Gln Glu Thr Ile Ile Thr Gly Lys Ala Thr Pro
        675                 680                 685
Gly Ala Thr Val Thr Ile Lys Asp Asn Leu Gly Asn Glu Ile Gly Thr
    690                 695                 700
Gly Val Ala Asn Asp Ala Gly Asn Phe Glu Ile Lys Thr Thr Ser Pro
705                 710                 715                 720
Leu Ala Glu Ala Thr Lys Val Ser Val Glu Ala Thr Lys Gly Gly Glu
                725                 730                 735
Ser Ser Asp Ala Val Glu Ala Thr Val Glu Gln Asn Asn Phe Gln Lys
            740                 745                 750
Gly Asn Pro Leu Ile Gln Pro Ala Ser Pro Thr Ala Val Thr Ala Val
        755                 760                 765
Thr Ile Lys Ala Ser Asp Gly Thr Asn Asn Ser Thr Thr Val Thr Gly
    770                 775                 780
Lys Ala Ala Ala Gly Glu Thr Val Thr Val Lys Asp Ser Ser Gly Asn
785                 790                 795                 800
Glu Ile Gly Thr Gly Val Val Gly Glu Asp Gly Thr Phe Thr Ile Thr
                805                 810                 815
Thr Asn Lys Pro Ile Ala Glu Asn Glu Arg Ile Gln Val Val Val Thr
            820                 825                 830
Lys Asp Asp Ala Glu Ser Glu Pro Thr Glu Ala Val Val Thr Ala Lys
        835                 840                 845
Thr Glu Pro Thr Asn Pro Thr Glu Val Thr Ala Lys Thr Leu Pro Asp
    850                 855                 860
Gly Asn Ser Asp Ser Thr Ile Val Ala Gly Lys Gly Lys Ala Gly Glu
865                 870                 875                 880
Val Val Thr Val Lys Asn Asp Ala Gly Lys Val Ile Gly Thr Gly Lys
                885                 890                 895
Val Ser Asp Asp Gly Thr Phe Ser Ile Lys Thr Asp Glu Val Ile Glu
            900                 905                 910
Pro Gly Lys Gln Val Ser Val Ile Thr Thr Asn Asp Gly Met Asp Ser
        915                 920                 925
Ile Pro Val Pro Val Thr Val Ser Gly Glu Thr Ile Thr Ser Ile Lys
```

```
                930              935               940
Gln Ser Ala Lys Ala Ala Val Asp Asn Leu Thr Tyr Leu Asn Asn Ala
945                 950                 955                 960

Gln Lys Gln Ser Ala Lys Asp Ala Ile Asp Ser Ala Asn Thr Val Asp
                965                 970                 975

Glu Ile Thr Thr Ala Lys Asn Asn Ala Val Ser Thr Asp Thr Asn Met
                    980                 985                 990

Lys Asp Leu Ser Glu Asp Thr Lys Leu Ala Ala Asp Lys Thr Gln Asp
                995                1000                1005

Pro Tyr Leu Asn Ala Asp Leu Asp Lys Lys Gln Ala Tyr Asp Lys Ala
       1010                1015                1020

Val Glu Glu Ala Gln Lys Leu Leu Asn Lys Glu Thr Gly Thr Ser Val
1025                1030                1035                1040

Gly Ala Asp Lys Asp Pro Ala Glu Val Ala Arg Ile Lys Gln Ala Val
            1045                1050                1055

Asp Asp Ala Tyr Asp Ala Leu Asn Gly Asn Ser Ser Leu Asp Asp Ala
                1060                1065                1070

Lys Gln Lys Ala Lys Asp Ala Val Asp Lys Asn Tyr Thr Asn Leu Asn
         1075                1080                1085

Asp Lys Gln Lys Glu Thr Ala Lys Lys Arg Ile Asp Ser Ala Lys Ser
      1090                1095                1100

Glu Asp Glu Val Asn Asn Ala Asp Lys Ile Asn Ser Gly Leu Asn Glu
1105                1110                1115                1120

Lys Met Gly Glu Leu Lys Glu Val Ser Asn Leu Ser Asp Lys Ile Glu
                1125                1130                1135

Thr Thr Ser Asn Tyr Ser Asn Ala Asp Ser Asp Lys Lys Gln Ala Tyr
            1140                1145                1150

Lys Glu Thr Ala Asp Lys Ile His Glu Thr Val Ala Pro Ser Gly Asp
         1155                1160                1165

Asp Leu Thr Thr Asp Asp Val Asn Asn Leu Ile Thr Asp Glu Ala Thr
      1170                1175                1180

Lys Arg Ala Ala Leu Asn Gly Asp Ala Arg Glu Lys Ala Arg Gln Glu
1185                1190                1195                1200

Leu Glu Asn Asn Tyr Asn Ser Gly Lys Ser Leu Gln Asp Gly Ser Thr
                1205                1210                1215

Leu Asp Pro Arg Tyr Tyr Asn Ala Ser Glu Glu Lys Lys Gln Ala Phe
            1220                1225                1230

Gln Lys Ala Leu Asp Asn Ala Lys Lys Ala Leu Asp Asn Ser Glu Thr
         1235                1240                1245

Thr Glu Ala Glu Tyr Lys Ser Ala Asn Asp Glu Leu Gln Lys Ala Lys
      1250                1255                1260

Ala Asp Leu Asp Gly Gln Thr Thr Asp Lys Ser Lys Leu Asp Asp Ala
1265                1270                1275                1280

Ile Lys Asp Ala Asn Asn Ala Lys Gly Thr Asp Lys Tyr Lys Asn Ala
            1285                1290                1295

Ser Asp Asp Thr Lys Ser Lys Phe Asp Glu Ala Leu Lys Lys Ala Glu
         1300                1305                1310

Glu Val Lys Asn Asn Ser Asn Ala Thr Gln Lys Glu Val Asp Asp Ala
      1315                1320                1325

Thr Asn Asn Leu Lys Gln Ala Gln Asn Leu Asn Gly Gln Thr Thr
1330                1335                1340

Asp Lys Ser Lys Leu Asp Asp Ala Ile Lys Asp Ala Asn Asn Ala Lys
1345                1350                1355                1360
```

```
Gly Thr Asp Lys Tyr Lys Asn Ala Ser Asp Asp Thr Lys Ser Lys Phe
            1365                1370                1375

Asp Asp Ala Leu Lys Lys Ala Glu Glu Val Lys Asn Asn Ser Asn Ala
        1380                1385                1390

Thr Gln Lys Glu Val Asp Asp Ala Thr Asn Asn Leu Lys Gln Ala Gln
        1395                1400                1405

Asn Asp Leu Asp Gly Gln Thr Thr Asp Lys Ser Lys Leu Asp Glu Ala
    1410                1415                1420

Ile Thr Asp Ala Asn Asn Thr Lys Leu Thr Asp Lys Tyr Asn Asn Ala
1425                1430                1435                1440

Ser Asp Asp Thr Lys Ser Lys Phe Asp Glu Ala Leu Lys Lys Ala Glu
            1445                1450                1455

Asn Val Lys Asn Asp Ser Asn Ala Thr Gln Lys Glu Val Asp Asp Ala
            1460                1465                1470

Thr Asn Asn Leu Lys Gln Ala Gln Asn Asp Leu Asp Gly Gln Thr Thr
        1475                1480                1485

Asp Lys Ser Lys Leu Asp Glu Ala Ile Thr Asp Ala Asn Asn Thr Lys
    1490                1495                1500

Ser Thr Asp Lys Tyr Asn Asn Ala Ser Asp Asp Thr Lys Ser Lys Phe
1505                1510                1515                1520

Asp Glu Ala Leu Lys Lys Ala Glu Glu Val Lys Asn Asn Ser Asn Ala
            1525                1530                1535

Thr Gln Lys Glu Val Asp Asp Ala Thr Asn Asn Leu Lys Gln Ala Gln
        1540                1545                1550

Asn Asn Leu Asp Gly Gln Thr Thr Asp Lys Ser Lys Leu Asp Glu Ala
    1555                1560                1565

Ile Thr Asp Ala Asn Asn Thr Lys Ser Thr Asp Lys Tyr Lys Asn Ala
1570                1575                1580

Ser Asp Asp Thr Lys Ser Lys Phe Asp Asp Ala Leu Lys Lys Ala Glu
1585                1590                1595                1600

Glu Val Lys Asn Asn Ser Asn Ala Thr Gln Lys Glu Val Asp Asp Ala
            1605                1610                1615

Thr Asn Asn Leu Lys Gln Ala Gln Asn Asp Leu Asp Gly Gln Thr Thr
            1620                1625                1630

Asn Lys Asp Thr Leu Asn Asp Ala Ile Lys Asp Ala Asn Asp Ala Lys
        1635                1640                1645

Gly Thr Asp Lys Tyr Lys Asn Ala Ser Asp Asp Thr Lys Ser Lys Leu
        1650                1655                1660

Asp Glu Thr Leu Lys Lys Ala Glu Glu Val Lys Asn Asn Ser Asn Ala
1665                1670                1675                1680

Thr Gln Lys Glu Val Asp Asp Ala Thr Asn Asn Leu Lys Gln Ala Gln
        1685                1690                1695

Asn Asp Leu Asp Gly Gln Thr Thr Asp Lys Ser Lys Leu Asp Glu Ala
    1700                1705                1710

Ile Lys Ser Ala Asp Asp Thr Lys Ser Thr Asp Lys Tyr Asn Asn Ala
    1715                1720                1725

Ser Asp Asp Thr Lys Ser Lys Phe Asp Glu Ala Leu Lys Lys Ala Glu
        1730                1735                1740

Glu Val Lys Asn Asn Ser Asn Ala Thr Gln Lys Glu Val Asp Asp Ala
1745                1750                1755                1760

Thr Lys Asn Leu Lys Gln Ala Gln Asn Asp Leu Asp Gly Gln Thr Thr
            1765                1770                1775
```

```
Asn Lys Asp Ala Ile Asn Asp Ala Ile Lys Asp Ala Asn Asn Ala Lys
        1780                1785                1790

Gly Thr Asp Lys Tyr Asn Asn Ala Ser Asp Asp Thr Lys Ser Lys Phe
        1795                1800                1805

Asp Asp Ala Leu Lys Lys Ala Glu Asp Val Lys Asn Asp Ser Asn Ala
        1810                1815                1820

Asn Gln Lys Glu Val Asp Asp Ala Thr Lys Asn Leu Lys Asn Thr Leu
1825                1830                1835                1840

Asn Asn Leu Lys Gly Gln Pro Ala Lys Lys Ala Asn Leu Ile Ala Ser
            1845                1850                1855

Lys Asp Asn Ala Lys Ile His Lys Gln Thr Leu Leu Pro Gln Thr Gly
        1860                1865                1870

Thr Glu Thr Asn Pro Leu Thr Ala Ile Gly Ile Gly Leu Met Ala Leu
        1875                1880                1885

Gly Ala Gly Ile Phe Ala Lys Lys Lys Arg Lys Asp Asp Glu Ala
    1890                1895                1900

<210> SEQ ID NO 4
<211> LENGTH: 199
<212> TYPE: PRT
<213> ORGANISM: Artificial Sequence
<220> FEATURE:
<223> OTHER INFORMATION: Description of Artificial Sequence:C370 cell
      wall associated (CWA) region

<400> SEQUENCE: 4

Lys Lys Ala Glu Glu Val Lys Asn Asn Ser Asn Ala Thr Gln Lys Glu
 1               5                  10                  15

Val Asp Asp Ala Thr Asn Asn Leu Lys Gln Ala Gln Asn Asp Leu Asp
             20                  25                  30

Gly Gln Thr Thr Asp Lys Ser Lys Leu Asp Glu Ala Ile Lys Ser Ala
         35                  40                  45

Asp Asp Thr Lys Ser Thr Asp Lys Tyr Asn Asn Ala Ser Asp Asp Thr
     50                  55                  60

Lys Ser Lys Phe Asp Glu Ala Leu Lys Lys Ala Glu Glu Val Lys Asn
 65                  70                  75                  80

Asn Ser Asn Ala Thr Gln Lys Glu Val Asp Asp Ala Thr Lys Asn Leu
                 85                  90                  95

Lys Gln Ala Gln Asn Asp Leu Asp Gly Gln Thr Thr Asn Lys Asp Ala
            100                 105                 110

Ile Asn Asp Ala Ile Lys Asp Ala Asn Asn Ala Lys Gly Thr Asp Lys
        115                 120                 125

Tyr Asn Asn Ala Ser Asp Asp Thr Lys Ser Lys Phe Asp Asp Ala Leu
    130                 135                 140

Lys Lys Ala Glu Asp Val Lys Asn Asp Ser Asn Ala Asn Gln Lys Glu
145                 150                 155                 160

Val Asp Asp Ala Thr Lys Asn Leu Lys Asn Thr Leu Asn Asn Leu Lys
                165                 170                 175

Gly Gln Pro Ala Lys Lys Ala Asn Leu Ile Ala Ser Lys Asp Asn Ala
            180                 185                 190

Lys Ile His Lys Gln Thr Leu
        195

<210> SEQ ID NO 5
<211> LENGTH: 95
<212> TYPE: PRT
<213> ORGANISM: Artificial Sequence
```

```
<220> FEATURE:
<223> OTHER INFORMATION: Description of Artificial Sequence:C370 cell
      wall associated fragment

<400> SEQUENCE: 5

Gly Gln Thr Thr Asn Lys Asp Ala Ile Asn Asp Ala Ile Lys Asp Ala
 1               5                  10                  15

Asn Asn Ala Lys Gly Thr Asp Lys Tyr Asn Asn Ala Ser Asp Asp Thr
            20                  25                  30

Lys Ser Lys Phe Asp Asp Ala Leu Lys Lys Ala Glu Asp Val Lys Asn
        35                  40                  45

Asp Ser Asn Ala Asn Gln Lys Glu Val Asp Asp Ala Thr Lys Asn Leu
    50                  55                  60

Lys Asn Thr Leu Asn Asn Leu Lys Gly Gln Pro Ala Lys Lys Ala Asn
65                  70                  75                  80

Leu Ile Ala Ser Lys Asp Asn Ala Lys Ile His Lys Gln Thr Leu
                85                  90                  95

<210> SEQ ID NO 6
<211> LENGTH: 202
<212> TYPE: PRT
<213> ORGANISM: Artificial Sequence
<220> FEATURE:
<223> OTHER INFORMATION: Description of Artificial Sequence:C14 cell
      wall associated (CWA) region

<400> SEQUENCE: 6

Val Thr Arg Thr Ile Asn Val Val Asp Pro Ile Thr Gly Lys Ile Ser
 1               5                  10                  15

Thr Ser Val Gln Thr Ala Lys Phe Thr Arg Glu Asp Lys Asn Ser Asn
            20                  25                  30

Ala Gly Tyr Thr Asp Pro Val Thr Gly Lys Thr Thr Met Asn Pro Trp
        35                  40                  45

Thr Pro Ala Lys Gln Gly Leu Arg Ala Val Asn Val Glu Gln Ile Lys
    50                  55                  60

Gly Tyr Val Ala Lys Val Asp Gly Asn Val Asp Ala Val Val Val Thr
65                  70                  75                  80

Pro Asp Ser Ala Asn Met Val Val Thr Ile Thr Tyr Gln Ala Asn Lys
                85                  90                  95

Pro Glu Gly Gln Asn Ile Thr Val Lys Lys Asp Thr Val Pro Asp Pro
            100                 105                 110

Ala Asp Gly Ile Lys Asn Lys Asp Asp Leu Pro Asp Gly Thr Lys Tyr
        115                 120                 125

Thr Trp Lys Glu Val Pro Asp Val Asn Ser Val Gly Glu Lys Thr Gly
    130                 135                 140

Ile Val Thr Val Thr Phe Pro Asp Gly Thr Ser Val Asp Val Lys Val
145                 150                 155                 160

Thr Val Tyr Val Asp Pro Val Val Glu Ser Asn Arg Asp Thr Leu Ser
                165                 170                 175

Lys Glu Ala Asn Thr Gly Asn Thr Asn Val Ala Lys Ala Ala Thr Val
            180                 185                 190

Thr Ser Ser Lys Val Glu Ser Lys Lys Thr
        195                 200

<210> SEQ ID NO 7
<211> LENGTH: 232
<212> TYPE: PRT
<213> ORGANISM: Artificial Sequence
```

```
<220> FEATURE:
<223> OTHER INFORMATION: Description of Artificial Sequence:C14 cell
      wall targeting region

<400> SEQUENCE: 7

Val Thr Arg Thr Ile Asn Val Val Asp Pro Ile Thr Gly Lys Ile Ser
 1               5                  10                  15

Thr Ser Val Gln Thr Ala Lys Phe Thr Arg Glu Asp Lys Asn Ser Asn
                20                  25                  30

Ala Gly Tyr Thr Asp Pro Val Thr Gly Lys Thr Thr Met Asn Pro Trp
            35                  40                  45

Thr Pro Ala Lys Gln Gly Leu Arg Ala Val Asn Val Glu Gln Ile Lys
        50                  55                  60

Gly Tyr Val Ala Lys Val Asp Gly Asn Val Asp Ala Val Val Val Thr
 65                  70                  75                  80

Pro Asp Ser Ala Asn Met Val Val Thr Ile Thr Tyr Gln Ala Asn Lys
                85                  90                  95

Pro Glu Gly Gln Asn Ile Thr Val Lys Lys Asp Thr Val Pro Asp Pro
            100                 105                 110

Ala Asp Gly Ile Lys Asn Lys Asp Asp Leu Pro Asp Gly Thr Lys Tyr
        115                 120                 125

Thr Trp Lys Glu Val Pro Asp Val Asn Ser Val Gly Glu Lys Thr Gly
    130                 135                 140

Ile Val Thr Val Thr Phe Pro Asp Gly Thr Ser Val Asp Val Lys Val
145                 150                 155                 160

Thr Val Tyr Val Asp Pro Val Val Glu Ser Asn Arg Asp Thr Leu Ser
                165                 170                 175

Lys Glu Ala Asn Thr Gly Asn Thr Asn Val Ala Lys Ala Ala Thr Val
            180                 185                 190

Thr Ser Ser Lys Val Glu Ser Lys Lys Thr Leu Pro Gln Thr Gly Ser
        195                 200                 205

Lys Thr Glu Gln Val Gly Ile Leu Gly Leu Ala Ile Ala Thr Val Gly
    210                 215                 220

Ser Leu Leu Gly Leu Gly Val Asn
225                 230

<210> SEQ ID NO 8
<211> LENGTH: 226
<212> TYPE: PRT
<213> ORGANISM: Artificial Sequence
<220> FEATURE:
<223> OTHER INFORMATION: Description of Artificial Sequence:C370 cell
      wall targeting region

<400> SEQUENCE: 8

Lys Lys Ala Glu Glu Val Lys Asn Asn Ser Asn Ala Thr Gln Lys Glu
 1               5                  10                  15

Val Asp Asp Ala Thr Asn Asn Leu Lys Gln Ala Gln Asn Asp Leu Asp
                20                  25                  30

Gly Gln Thr Thr Asp Lys Ser Lys Leu Asp Glu Ala Ile Lys Ser Ala
            35                  40                  45

Asp Asp Thr Lys Ser Thr Asp Lys Tyr Asn Asn Ala Ser Asp Asp Thr
        50                  55                  60

Lys Ser Lys Phe Asp Glu Ala Leu Lys Lys Ala Glu Glu Val Lys Asn
 65                  70                  75                  80

Asn Ser Asn Ala Thr Gln Lys Glu Val Asp Asp Ala Thr Lys Asn Leu
                85                  90                  95
```

Lys Gln Ala Gln Asn Asp Leu Asp Gly Gln Thr Thr Asn Lys Asp Ala
                100                 105                 110

Ile Asn Asp Ala Ile Lys Asp Ala Asn Asn Ala Lys Gly Thr Asp Lys
            115                 120                 125

Tyr Asn Asn Ala Ser Asp Asp Thr Lys Ser Lys Phe Asp Asp Ala Leu
    130                 135                 140

Lys Lys Ala Glu Asp Val Lys Asn Asp Ser Asn Ala Asn Gln Lys Glu
145                 150                 155                 160

Val Asp Asp Ala Thr Lys Asn Leu Lys Asn Thr Leu Asn Asn Leu Lys
                165                 170                 175

Gly Gln Pro Ala Lys Lys Ala Asn Leu Ile Ala Ser Lys Asp Asn Ala
            180                 185                 190

Lys Ile His Lys Gln Thr Leu Leu Pro Gln Thr Gly Thr Glu Thr Asn
        195                 200                 205

Pro Leu Thr Ala Ile Gly Ile Gly Leu Met Ala Leu Gly Ala Gly Ile
    210                 215                 220

Phe Ala
225

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence:
      Streptococcus pyogenes M6 (emm6) protein signature cell wall
      sorting signal motif, substrate for sortase-like
      proteins, cell wall anchor motif
<220> FEATURE:
<221> NAME/KEY: MOD_RES
<222> LOCATION: (3)
<223> OTHER INFORMATION: Xaa = any amino acid

<400> SEQUENCE: 9

Leu Pro Xaa Thr Gly
 1               5

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence:C-terminus
      positive charged residues cell surface retention
      signal

<400> SEQUENCE: 10

Lys Arg Lys Glu Glu Asn
 1               5

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence:cell wall
      targeting region

<400> SEQUENCE: 11

Leu Pro Gln Ser Gly
 1               5

<210> SEQ ID NO 12

```
<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence:cell wall
      targeting region

<400> SEQUENCE: 12

Leu Pro Gln Ala Gly
  1               5

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence:cell wall
      targeting region, cell wall sorting signal, cell
      wall associated (CWA) domain

<400> SEQUENCE: 13

Leu Pro Gln Thr Gly
  1               5

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence:cell wall
      targeting region

<400> SEQUENCE: 14

Leu Pro Gln Thr Ala
  1               5

<210> SEQ ID NO 15
<211> LENGTH: 10
<212> TYPE: PRT
<213> ORGANISM: Artificial Sequence
<220> FEATURE:
<223> OTHER INFORMATION: Description of Artificial Sequence:c-Myc
      epitope, c-Myc tag

<400> SEQUENCE: 15

Glu Gln Lys Leu Ile Ser Glu Glu Asp Leu
  1               5                  10

<210> SEQ ID NO 16
<211> LENGTH: 8
<212> TYPE: PRT
<213> ORGANISM: Artificial Sequence
<220> FEATURE:
<223> OTHER INFORMATION: Description of Artificial Sequence:C14
      C-terminal charged tail

<400> SEQUENCE: 16

Val Asn Arg Lys Lys Arg Gln Lys
  1               5

<210> SEQ ID NO 17
<211> LENGTH: 11
<212> TYPE: PRT
<213> ORGANISM: Artificial Sequence
<220> FEATURE:
<223> OTHER INFORMATION: Description of Artificial Sequence:C370
      C-terminal charged tail

<400> SEQUENCE: 17
```

```
Phe Ala Lys Lys Lys Arg Lys Asp Asp Glu Ala
  1               5                  10

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence:cell wall
      sorting signal, cell wall targeting region

<400> SEQUENCE: 18

Leu Pro Gln Ser Ala
  1               5

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence:cell wall
      sorting signal, cell wall targeting region

<400> SEQUENCE: 19

Leu Pro Gln Ala Ala
  1               5

<210> SEQ ID NO 20
<211> LENGTH: 19
<212> TYPE: PRT
<213> ORGANISM: Artificial Sequence
<220> FEATURE:
<223> OTHER INFORMATION: Description of Artificial Sequence:C14 carboxyl
      terminus hydrophobic region spanning bacterial
      membrane

<400> SEQUENCE: 20

Val Gly Ile Leu Gly Leu Ala Ile Ala Thr Val Gly Ser Leu Leu Gly
  1               5                  10                  15

Leu Gly Val

<210> SEQ ID NO 21
<211> LENGTH: 18
<212> TYPE: PRT
<213> ORGANISM: Artificial Sequence
<220> FEATURE:
<223> OTHER INFORMATION: Description of Artificial Sequence:C370
      carboxyl terminus hydrophobic region spanning bacterial
      membrane

<400> SEQUENCE: 21

Pro Leu Thr Ala Ile Gly Ile Gly Leu Met Ala Leu Gly Ala Gly Ile
  1               5                  10                  15

Phe Ala

<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence:C191
      exemplary carboxyl terminal positive charged region,
      positive charged tails

<400> SEQUENCE: 22

Lys Lys Arg Lys Glu Asp
```

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence:C14
      exemplary carboxyl terminal positive charged region,
      positive charged tails

<400> SEQUENCE: 23

Arg Lys Lys Arg Gln Lys
 1               5

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence:C370
      exemplary carboxyl terminal positive charged region,
      positive charged tails

<400> SEQUENCE: 24

Lys Lys Lys Arg Lys Asp Asp Glu Ala
 1               5

<210> SEQ ID NO 25
<211> LENGTH: 23
<212> TYPE: PRT
<213> ORGANISM: Artificial Sequence
<220> FEATURE:
<223> OTHER INFORMATION: Description of Artificial Sequence:exemplary
      signal sequence from amino terminus of
      alpha-amylase of Lactobacillus amylovorus

<400> SEQUENCE: 25

Met Lys Lys Asn Leu Arg Ile Val Ser Ala Ala Ala Ala Leu Leu
 1               5                  10                  15

Ala Val Ala Pro Val Ala Ala
            20

<210> SEQ ID NO 26
<211> LENGTH: 23
<212> TYPE: PRT
<213> ORGANISM: Artificial Sequence
<220> FEATURE:
<223> OTHER INFORMATION: Description of Artificial Sequence:exemplary
      signal sequence from amino terminus of S-layer
      gene (cbsA) of Lactobacillus crispatus

<400> SEQUENCE: 26

Met Lys Lys Asn Leu Arg Ile Val Ser Ala Ala Ala Ala Leu Leu
 1               5                  10                  15

Ala Val Ala Thr Val Ser Ala
            20

<210> SEQ ID NO 27
<211> LENGTH: 5
<212> TYPE: PRT
<213> ORGANISM: Artificial Sequence
<220> FEATURE:
<223> OTHER INFORMATION: Description of Artificial Sequence:
      Lactobacillus paracasei PrtP protease sorting signal

<400> SEQUENCE: 27

-continued

Leu Pro Lys Thr Ala
 1               5

<210> SEQ ID NO 28
<211> LENGTH: 5
<212> TYPE: PRT
<213> ORGANISM: Artificial Sequence
<220> FEATURE:
<223> OTHER INFORMATION: Description of Artificial Sequence:
      Staphylococcus aureus protein A cell wall sorting motif

<400> SEQUENCE: 28

Leu Pro Glu Thr Gly
 1               5

<210> SEQ ID NO 29
<211> LENGTH: 5
<212> TYPE: PRT
<213> ORGANISM: Artificial Sequence
<220> FEATURE:
<223> OTHER INFORMATION: Description of Artificial
      Sequence:Peptostreptococcus magnus protein L and
      human serum albumin binding protein sorting signal
      motif
<220> FEATURE:
<221> NAME/KEY: MOD_RES
<222> LOCATION: (3)
<223> OTHER INFORMATION: Xaa = any amino acid

<400> SEQUENCE: 29

Leu Pro Xaa Ala Gly
 1               5

<210> SEQ ID NO 30
<211> LENGTH: 5
<212> TYPE: PRT
<213> ORGANISM: Artificial Sequence
<220> FEATURE:
<223> OTHER INFORMATION: Description of Artificial Sequence:
      Lactobacillus paracasei sorting signal motif
<220> FEATURE:
<221> NAME/KEY: MOD_RES
<222> LOCATION: (3)
<223> OTHER INFORMATION: Xaa = any amino acid

<400> SEQUENCE: 30

Leu Pro Xaa Thr Ala
 1               5

<210> SEQ ID NO 31
<211> LENGTH: 6
<212> TYPE: PRT
<213> ORGANISM: Artificial Sequence
<220> FEATURE:
<223> OTHER INFORMATION: Description of Artificial Sequence:
      Gram-positive bacterial cell wall anchored protein conserved
      C-terminal motif
<220> FEATURE:
<221> NAME/KEY: MOD_RES
<222> LOCATION: (1)..(6)
<223> OTHER INFORMATION: Xaa = any amino acid

<400> SEQUENCE: 31

Leu Pro Xaa Thr Gly Xaa
 1               5

<210> SEQ ID NO 32
<211> LENGTH: 30
<212> TYPE: DNA
<213> ORGANISM: Artificial Sequence

```
<220> FEATURE:
<223> OTHER INFORMATION: Description of Artificial Sequence:PCR
      amplification oligonucleotide primer P23.f

<400> SEQUENCE: 32
gtggagctcc ccgaaaagcc ctgacaaccc                                       30

<210> SEQ ID NO 33
<211> LENGTH: 26
<212> TYPE: DNA
<213> ORGANISM: Artificial Sequence
<220> FEATURE:
<223> OTHER INFORMATION: Description of Artificial Sequence:PCR
      amplification oligonucleotide primer P23.r

<400> SEQUENCE: 33
ggaaacacgc tagcactaac ttcatt                                           26

<210> SEQ ID NO 34
<211> LENGTH: 30
<212> TYPE: DNA
<213> ORGANISM: Artificial Sequence
<220> FEATURE:
<223> OTHER INFORMATION: Description of Artificial Sequence:PCR
      amplification oligonucleotide primer 2DCD4.f

<400> SEQUENCE: 34
gcggctagca agaaagttgt tttaggtaaa                                       30

<210> SEQ ID NO 35
<211> LENGTH: 30
<212> TYPE: DNA
<213> ORGANISM: Artificial Sequence
<220> FEATURE:
<223> OTHER INFORMATION: Description of Artificial Sequence:PCR
      amplification oligonucleotide primer 2DCD4.r

<400> SEQUENCE: 35
gcacaattgt gatgcctttt gaaaagctaa                                       30

<210> SEQ ID NO 36
<211> LENGTH: 27
<212> TYPE: DNA
<213> ORGANISM: Artificial Sequence
<220> FEATURE:
<223> OTHER INFORMATION: Description of Artificial Sequence:PCR
      amplification oligonucleotide primer CbsAss.f

<400> SEQUENCE: 36
gcgaattcaa ggaggaaaag accacat                                          27

<210> SEQ ID NO 37
<211> LENGTH: 27
<212> TYPE: DNA
<213> ORGANISM: Artificial Sequence
<220> FEATURE:
<223> OTHER INFORMATION: Description of Artificial Sequence:PCR
      amplification oligonucleotide primer CbsAss.r

<400> SEQUENCE: 37
ccagctagct gaaacagtag aaacggc                                          27

<210> SEQ ID NO 38
<211> LENGTH: 59
<212> TYPE: DNA
<213> ORGANISM: Artificial Sequence
<220> FEATURE:
```

-continued

<223> OTHER INFORMATION: Description of Artificial Sequence:5'
      oligonucleotide primer Myc14nhe

<400> SEQUENCE: 38
gcgctagcga acagaaactg atctccgaag aggacctggt aactcgtact atcaatgta    59

<210> SEQ ID NO 39
<211> LENGTH: 30
<212> TYPE: DNA
<213> ORGANISM: Artificial Sequence
<220> FEATURE:
<223> OTHER INFORMATION: Description of Artificial Sequence:3'
      oligonucleotide primer Myc14mfe

<400> SEQUENCE: 39
cgccaattgc tacttttgac gtttctttct    30

<210> SEQ ID NO 40
<211> LENGTH: 57
<212> TYPE: DNA
<213> ORGANISM: Artificial Sequence
<220> FEATURE:
<223> OTHER INFORMATION: Description of Artificial Sequence:5'
      oligonucleotide primer Myc191nhe

<400> SEQUENCE: 40
gcgctagcga acagaaactg atctccgaag aggacctgga cgtagtaatt ccaggaa    57

<210> SEQ ID NO 41
<211> LENGTH: 30
<212> TYPE: DNA
<213> ORGANISM: Artificial Sequence
<220> FEATURE:
<223> OTHER INFORMATION: Description of Artificial Sequence:3'
      oligonucleotide primer Myc191mfe

<400> SEQUENCE: 41
gcgcaattgt taatcttctt ttctcttctt    30

<210> SEQ ID NO 42
<211> LENGTH: 58
<212> TYPE: DNA
<213> ORGANISM: Artificial Sequence
<220> FEATURE:
<223> OTHER INFORMATION: Description of Artificial Sequence:5'
      oligonucleotide primer Myc370nhe

<400> SEQUENCE: 42
gcgctagcga acagaaactg atctccgaag aggacctgtt gaagaaggca gaagaagt    58

<210> SEQ ID NO 43
<211> LENGTH: 30
<212> TYPE: DNA
<213> ORGANISM: Artificial Sequence
<220> FEATURE:
<223> OTHER INFORMATION: Description of Artificial Sequence:3'
      oligonucleotide primer Myc370mfe

<400> SEQUENCE: 43
ccgcaattgt tatgcttcat catctttct    30

<210> SEQ ID NO 44
<211> LENGTH: 30
<212> TYPE: DNA
<213> ORGANISM: Artificial Sequence
<220> FEATURE:
<223> OTHER INFORMATION: Description of Artificial Sequence:C14 PCR amplification 5' primer

<400> SEQUENCE: 44
gcgcaattgg taactcgtac tatcaatgta                                30

<210> SEQ ID NO 45
<211> LENGTH: 30
<212> TYPE: DNA
<213> ORGANISM: Artificial Sequence
<220> FEATURE:
<223> OTHER INFORMATION: Description of Artificial Sequence:C14 PCR
      amplification 3' primer

<400> SEQUENCE: 45
cgctctagat acacaaacta ttttacggtc                                30

<210> SEQ ID NO 46
<211> LENGTH: 30
<212> TYPE: DNA
<213> ORGANISM: Artificial Sequence
<220> FEATURE:
<223> OTHER INFORMATION: Description of Artificial Sequence:C191 PCR
      amplification 5' primer

<400> SEQUENCE: 46
gcgcaattgg acgtagtaat tccaggaaca                                30

<210> SEQ ID NO 47
<211> LENGTH: 30
<212> TYPE: DNA
<213> ORGANISM: Artificial Sequence
<220> FEATURE:
<223> OTHER INFORMATION: Description of Artificial Sequence:C191 PCR
      amplification 3' primer

<400> SEQUENCE: 47
cggtctagac caagcaattt atatattgct                                30

<210> SEQ ID NO 48
<211> LENGTH: 26
<212> TYPE: DNA
<213> ORGANISM: Artificial Sequence
<220> FEATURE:
<223> OTHER INFORMATION: Description of Artificial Sequence:C370 PCR
      amplification 5' primer

<400> SEQUENCE: 48
gcgcaattga agaaggcaga agaagt                                    26

<210> SEQ ID NO 49
<211> LENGTH: 30
<212> TYPE: DNA
<213> ORGANISM: Artificial Sequence
<220> FEATURE:
<223> OTHER INFORMATION: Description of Artificial Sequence:C370 PCR
      amplification 3' primer

<400> SEQUENCE: 49
ccgtctagat tatgcttcat catcttttct                                30

<210> SEQ ID NO 50
<211> LENGTH: 30
<212> TYPE: DNA
<213> ORGANISM: Artificial Sequence
<220> FEATURE:
<223> OTHER INFORMATION: Description of Artificial Sequence:shuttle
      vector cloning primer Mfec14up

```
<400> SEQUENCE: 50
gcgcaattgc cacaaactgg ttctaagact                                      30

<210> SEQ ID NO 51
<211> LENGTH: 30
<212> TYPE: DNA
<213> ORGANISM: Artificial Sequence
<220> FEATURE:
<223> OTHER INFORMATION: Description of Artificial Sequence:shuttle
      vector cloning 3' primer Xnac14lo

<400> SEQUENCE: 51
cgctctagat acacaaacta ttttacggtc                                      30

<210> SEQ ID NO 52
<211> LENGTH: 26
<212> TYPE: DNA
<213> ORGANISM: Artificial Sequence
<220> FEATURE:
<223> OTHER INFORMATION: Description of Artificial Sequence:C370
      repetitive cell wall spanning region zero repeat PCR
      amplification 5' primer

<400> SEQUENCE: 52
cggcaattgc ctcaaactgg tactga                                          26

<210> SEQ ID NO 53
<211> LENGTH: 30
<212> TYPE: DNA
<213> ORGANISM: Artificial Sequence
<220> FEATURE:
<223> OTHER INFORMATION: Description of Artificial Sequence:C370
      repetitive cell wall spanning region one repeat PCR
      amplification 5' primer

<400> SEQUENCE: 53
cggcaattgg gtcaaactac aaataaagat                                      30

<210> SEQ ID NO 54
<211> LENGTH: 30
<212> TYPE: DNA
<213> ORGANISM: Artificial Sequence
<220> FEATURE:
<223> OTHER INFORMATION: Description of Artificial Sequence:C370
      repetitive cell wall spanning region two repeat PCR
      amplification 5' primer

<400> SEQUENCE: 54
cgccaattgg gtcaaactac tgataagagt                                      30

<210> SEQ ID NO 55
<211> LENGTH: 30
<212> TYPE: DNA
<213> ORGANISM: Artificial Sequence
<220> FEATURE:
<223> OTHER INFORMATION: Description of Artificial Sequence:C370
      repetitive cell wall spanning region three repeat PCR
      amplification 5' primer

<400> SEQUENCE: 55
gcgcaattgg gtcaaactac aaataaagat                                      30

<210> SEQ ID NO 56
<211> LENGTH: 30
<212> TYPE: DNA
<213> ORGANISM: Artificial Sequence
```

```
<220> FEATURE:
<223> OTHER INFORMATION: Description of Artificial Sequence:C370
      repetitive cell wall spanning region four-eight repeat PCR
      amplification 5' primer

<400> SEQUENCE: 56
cggcaattgg gtcaaactac tgacaagagc                                        30

<210> SEQ ID NO 57
<211> LENGTH: 42
<212> TYPE: DNA
<213> ORGANISM: Artificial Sequence
<220> FEATURE:
<223> OTHER INFORMATION: Description of Artificial Sequence:C14
      nucleotide sequence corresponding to LPQTG and flanking
      sequences

<400> SEQUENCE: 57
gaaagtaaga agactttacc acaaactggt tctaagactg aa                          42

<210> SEQ ID NO 58
<211> LENGTH: 46
<212> TYPE: DNA
<213> ORGANISM: Artificial Sequence
<220> FEATURE:
<223> OTHER INFORMATION: Description of Artificial Sequence:C370
      nucleotide sequence corresponding to LPQTG and flanking
      sequences

<400> SEQUENCE: 58
cataagcaaa ctctattgcc tcaaactggt actgaaacta acccac                      46

<210> SEQ ID NO 59
<211> LENGTH: 37
<212> TYPE: DNA
<213> ORGANISM: Artificial Sequence
<220> FEATURE:
<223> OTHER INFORMATION: Description of Artificial Sequence:C14
      site-directed mutagenic primer 237P(A)

<400> SEQUENCE: 59
gaaagtaaga agactttagc acaaactggt tctaaga                                37

<210> SEQ ID NO 60
<211> LENGTH: 38
<212> TYPE: DNA
<213> ORGANISM: Artificial Sequence
<220> FEATURE:
<223> OTHER INFORMATION: Description of Artificial Sequence:C14
      site-directed mutagenic primer 237P(A)

<400> SEQUENCE: 60
gtcttagaac cagtttgtgc taaagtcttc ttactttc                               38

<210> SEQ ID NO 61
<211> LENGTH: 38
<212> TYPE: DNA
<213> ORGANISM: Artificial Sequence
<220> FEATURE:
<223> OTHER INFORMATION: Description of Artificial Sequence:C14
      site-directed mutagenic primer 237P(N)

<400> SEQUENCE: 61
gaaagtaaga agactttaaa tcaaactggt tctaagac                               38

<210> SEQ ID NO 62
<211> LENGTH: 38
```

-continued

<210> SEQ ID NO 62
<211> LENGTH: 38
<212> TYPE: DNA
<213> ORGANISM: Artificial Sequence
<220> FEATURE:
<223> OTHER INFORMATION: Description of Artificial Sequence:C14
site-directed mutagenic primer 237P(N)

<400> SEQUENCE: 62
gtcttagaac cagtttgatt taaagtcttc ttactttc                              38

<210> SEQ ID NO 63
<211> LENGTH: 36
<212> TYPE: DNA
<213> ORGANISM: Artificial Sequence
<220> FEATURE:
<223> OTHER INFORMATION: Description of Artificial Sequence:C14
site-directed mutagenic primer 237T(A)

<400> SEQUENCE: 63
agaagacttt accacaagct ggttctaaga ctgaac                                36

<210> SEQ ID NO 64
<211> LENGTH: 36
<212> TYPE: DNA
<213> ORGANISM: Artificial Sequence
<220> FEATURE:
<223> OTHER INFORMATION: Description of Artificial Sequence:C14
site-directed mutagenic primer 237T(A)

<400> SEQUENCE: 64
gttcagtctt agaaccagct tgtggtaaag tcttct                                36

<210> SEQ ID NO 65
<211> LENGTH: 36
<212> TYPE: DNA
<213> ORGANISM: Artificial Sequence
<220> FEATURE:
<223> OTHER INFORMATION: Description of Artificial Sequence:C14
site-directed mutagenic primer 237T(G)

<400> SEQUENCE: 65
agaagacttt accacaaggt ggttctaaga ctgaac                                36

<210> SEQ ID NO 66
<211> LENGTH: 36
<212> TYPE: DNA
<213> ORGANISM: Artificial Sequence
<220> FEATURE:
<223> OTHER INFORMATION: Description of Artificial Sequence:C14
site-directed mutagenic primer 237T(G)

<400> SEQUENCE: 66
gttcagtctt agaaccacct tgtggtaaag tcttct                                36

<210> SEQ ID NO 67
<211> LENGTH: 36
<212> TYPE: DNA
<213> ORGANISM: Artificial Sequence
<220> FEATURE:
<223> OTHER INFORMATION: Description of Artificial Sequence:C14
site-directed mutagenic primer 237T(S)

<400> SEQUENCE: 67
agaagacttt accacaaagt ggttctaaga ctgaac                                36

<210> SEQ ID NO 68
<211> LENGTH: 36
<212> TYPE: DNA

<213> ORGANISM: Artificial Sequence
<220> FEATURE:
<223> OTHER INFORMATION: Description of Artificial Sequence:C14
      site-directed mutagenic primer 237T(S)

<400> SEQUENCE: 68
gttagtttca gtaccacttt gaggcaatag agtttg                                   36

<210> SEQ ID NO 69
<211> LENGTH: 35
<212> TYPE: DNA
<213> ORGANISM: Artificial Sequence
<220> FEATURE:
<223> OTHER INFORMATION: Description of Artificial Sequence:C14
      site-directed mutagenic primer 237G(A)

<400> SEQUENCE: 69
gactttacca caaactgctt ctaagactga acaag                                    35

<210> SEQ ID NO 70
<211> LENGTH: 35
<212> TYPE: DNA
<213> ORGANISM: Artificial Sequence
<220> FEATURE:
<223> OTHER INFORMATION: Description of Artificial Sequence:C14
      site-directed mutagenic primer 237G(A)

<400> SEQUENCE: 70
cttgttcagt cttagaagca gtttgtggta aagtc                                    35

<210> SEQ ID NO 71
<211> LENGTH: 38
<212> TYPE: DNA
<213> ORGANISM: Artificial Sequence
<220> FEATURE:
<223> OTHER INFORMATION: Description of Artificial Sequence:C370
      site-directed mutagenic primer 249P(A)

<400> SEQUENCE: 71
cataagcaaa ctctattggc tcaaactggt actgaaac                                 38

<210> SEQ ID NO 72
<211> LENGTH: 38
<212> TYPE: DNA
<213> ORGANISM: Artificial Sequence
<220> FEATURE:
<223> OTHER INFORMATION: Description of Artificial Sequence:C370
      site-directed mutagenic primer 249P(A)

<400> SEQUENCE: 72
gtttcagtac cagtttgagc caatagagtt tgcttatg                                 38

<210> SEQ ID NO 73
<211> LENGTH: 38
<212> TYPE: DNA
<213> ORGANISM: Artificial Sequence
<220> FEATURE:
<223> OTHER INFORMATION: Description of Artificial Sequence:C370
      site-directed mutagenic primer 249P(N)

<400> SEQUENCE: 73
cataagcaaa ctctattgaa tcaaactggt actgaaac                                 38

<210> SEQ ID NO 74
<211> LENGTH: 38
<212> TYPE: DNA
<213> ORGANISM: Artificial Sequence

```
<220> FEATURE:
<223> OTHER INFORMATION: Description of Artificial Sequence:C370
      site-directed mutagenic primer 249P(N)

<400> SEQUENCE: 74
gtttcagtac cagtttgatt caatagagtt tgcttatg                            38

<210> SEQ ID NO 75
<211> LENGTH: 35
<212> TYPE: DNA
<213> ORGANISM: Artificial Sequence
<220> FEATURE:
<223> OTHER INFORMATION: Description of Artificial Sequence:C370
      site-directed mutagenic primer 249T(A)

<400> SEQUENCE: 75
caaactctat tgcctcaaag tggtactgaa actaa                               35

<210> SEQ ID NO 76
<211> LENGTH: 36
<212> TYPE: DNA
<213> ORGANISM: Artificial Sequence
<220> FEATURE:
<223> OTHER INFORMATION: Description of Artificial Sequence:C370
      site-directed mutagenic primer 249T(A)

<400> SEQUENCE: 76
gttagtttca gtaccagttt gaggcaatag agtttg                              36

<210> SEQ ID NO 77
<211> LENGTH: 36
<212> TYPE: DNA
<213> ORGANISM: Artificial Sequence
<220> FEATURE:
<223> OTHER INFORMATION: Description of Artificial Sequence:C370
      site-directed mutagenic primer 249T(G)

<400> SEQUENCE: 77
caaactctat tgcctcaagg tggtactgaa actaac                              36

<210> SEQ ID NO 78
<211> LENGTH: 36
<212> TYPE: DNA
<213> ORGANISM: Artificial Sequence
<220> FEATURE:
<223> OTHER INFORMATION: Description of Artificial Sequence:C370
      site-directed mutagenic primer 249T(G)

<400> SEQUENCE: 78
gttagtttca gtaccacctt gaggcaatag agtttg                              36

<210> SEQ ID NO 79
<211> LENGTH: 33
<212> TYPE: DNA
<213> ORGANISM: Artificial Sequence
<220> FEATURE:
<223> OTHER INFORMATION: Description of Artificial Sequence:C370
      site-directed mutagenic primer 249T(S)

<400> SEQUENCE: 79
caaactctat tgcctcaaag tggtactgaa act                                 33

<210> SEQ ID NO 80
<211> LENGTH: 36
<212> TYPE: DNA
<213> ORGANISM: Artificial Sequence
<220> FEATURE:
```

```
<223> OTHER INFORMATION: Description of Artificial Sequence:C370
      site-directed mutagenic primer 249T(S)

<400> SEQUENCE: 80
gttagtttca gtaccacttt gaggcaatag agtttg                              36

<210> SEQ ID NO 81
<211> LENGTH: 36
<212> TYPE: DNA
<213> ORGANISM: Artificial Sequence
<220> FEATURE:
<223> OTHER INFORMATION: Description of Artificial Sequence:C370
      site-directed mutagenic primer 249G(A)

<400> SEQUENCE: 81
ctctattgcc tcaaactgct actgaaacta acccac                              36

<210> SEQ ID NO 82
<211> LENGTH: 36
<212> TYPE: DNA
<213> ORGANISM: Artificial Sequence
<220> FEATURE:
<223> OTHER INFORMATION: Description of Artificial Sequence:C370
      site-directed mutagenic primer 249G(A)

<400> SEQUENCE: 82
gtgggttagt ttcagtagca gtttgaggca atagag                              36

<210> SEQ ID NO 83
<211> LENGTH: 21
<212> TYPE: DNA
<213> ORGANISM: Artificial Sequence
<220> FEATURE:
<223> OTHER INFORMATION: Description of Artificial Sequence:CD4F forward
      amplification primer oligonucleotide

<400> SEQUENCE: 83
gatcgtgctg attcacgtcg t                                              21

<210> SEQ ID NO 84
<211> LENGTH: 33
<212> TYPE: DNA
<213> ORGANISM: Artificial Sequence
<220> FEATURE:
<223> OTHER INFORMATION: Description of Artificial Sequence:C14-7
      reverse amplification primer oligonucleotide

<400> SEQUENCE: 84
gcgctctaga ctaaacacct aagcctaata agc                                 33

<210> SEQ ID NO 85
<211> LENGTH: 35
<212> TYPE: DNA
<213> ORGANISM: Artificial Sequence
<220> FEATURE:
<223> OTHER INFORMATION: Description of Artificial Sequence:C14-6
      reverse amplification primer oligonucleotide

<400> SEQUENCE: 85
gcgctctaga ctagttaaca cctaagccta ataag                               35

<210> SEQ ID NO 86
<211> LENGTH: 31
<212> TYPE: DNA
<213> ORGANISM: Artificial Sequence
<220> FEATURE:
<223> OTHER INFORMATION: Description of Artificial Sequence:C14-5
```

```
      reverse amplification primer oligonucleotide

<400> SEQUENCE: 86
gcgctctaga ctatctgtta acacctaagc c                              31

<210> SEQ ID NO 87
<211> LENGTH: 33
<212> TYPE: DNA
<213> ORGANISM: Artificial Sequence
<220> FEATURE:
<223> OTHER INFORMATION: Description of Artificial Sequence:370-10
      reverse amplification primer oligonucleotide

<400> SEQUENCE: 87
gcgctctaga ttaaaaaatt cctgcgccta atg                            33

<210> SEQ ID NO 88
<211> LENGTH: 36
<212> TYPE: DNA
<213> ORGANISM: Artificial Sequence
<220> FEATURE:
<223> OTHER INFORMATION: Description of Artificial Sequence:370-9
      reverse amplification primer oligonucleotide

<400> SEQUENCE: 88
gcgctctaga ttatgcaaaa attcctgcgc ctaatg                         36

<210> SEQ ID NO 89
<211> LENGTH: 34
<212> TYPE: DNA
<213> ORGANISM: Artificial Sequence
<220> FEATURE:
<223> OTHER INFORMATION: Description of Artificial Sequence:370-8
      reverse amplification primer oligonucleotide

<400> SEQUENCE: 89
gcgctctaga ttactttgca aaaattcctg cgcc                           34
```